US008815251B2

(12) United States Patent  (10) Patent No.: US 8,815,251 B2
Caplan et al.  (45) Date of Patent: Aug. 26, 2014

(54) MICROBIAL DELIVERY SYSTEM

(71) Applicant: Allertein Therapeutics, LLC, Fairfield, CT (US)

(72) Inventors: Michael J. Caplan, Woodbridge, CT (US); Howard B. Sosin, Fairfield, CT (US); H. Kim Bottomly, Wellesley, MA (US); A. Wesley Burks, Jr., Chapel Hill, NC (US); Hugh A. Sampson, Larchmont, NY (US)

(73) Assignee: Allertein Therapeutics, LLC, Fairfield, CT (US)

( * ) Notice: Subject to any disclaimer, the term of this patent is extended or adjusted under 35 U.S.C. 154(b) by 0 days.

(21) Appl. No.: 13/742,828

(22) Filed: Jan. 16, 2013

(65) Prior Publication Data

US 2013/0243814 A1  Sep. 19, 2013

Related U.S. Application Data

(60) Continuation of application No. 10/728,323, filed on Dec. 4, 2003, now abandoned, which is a division of application No. 09/731,375, filed on Dec. 6, 2000, now Pat. No. 8,153,414.

(60) Provisional application No. 60/195,035, filed on Apr. 6, 2000.

(51) Int. Cl.
*A61K 39/35* (2006.01)
*C07K 14/245* (2006.01)

(52) U.S. Cl.
USPC .................. 424/200.1; 424/275.1; 424/93.4; 424/241.1; 435/252.8

(58) Field of Classification Search
None
See application file for complete search history.

(56) References Cited

U.S. PATENT DOCUMENTS

| | | |
|---|---|---|
| 3,097,141 A | 7/1963 | Kidwell |
| 3,645,852 A | 2/1972 | Axen et al. ........... 195/68 |
| 3,720,760 A | 3/1973 | Bennich et al. ........... 436/51.3 |
| 4,171,299 A | 10/1979 | Hamburger ........... 260/112.5 |
| 4,338,297 A | 7/1982 | Michael et al. ........... 424/91 |
| 4,469,677 A | 9/1984 | Michael et al. ........... 424/91 |
| 4,535,010 A | 8/1985 | Axen et al. ........... 427/246 |
| 4,579,840 A | 4/1986 | Hahn et al. ........... 514/14 |
| 4,658,022 A | 4/1987 | Knowles et al. ........... 530/402 |
| 4,659,678 A | 4/1987 | Forrest et al. ........... 436/512 |
| 4,696,915 A | 9/1987 | Horecker |
| 4,816,449 A | 3/1989 | Hahn et al. ........... 514/17 |
| 4,849,337 A | 7/1989 | Calenoff et al. ........... 435/7 |
| 4,849,404 A | 7/1989 | Iwai et al. ........... 514/2 |
| 4,900,556 A | 2/1990 | Wheatley et al. ........... 424/450 |
| 4,959,314 A | 9/1990 | Mark et al. ........... 435/69.1 |
| 5,026,545 A | 6/1991 | Saint-Remy et al. |
| 5,049,390 A | 9/1991 | Wojdani ........... 424/450 |
| 5,061,790 A | 10/1991 | Elting et al. ........... 530/402 |
| 5,091,318 A | 2/1992 | Anawis et al. ........... 436/513 |
| 5,169,933 A | 12/1992 | Anderson et al. ........... 531/391.3 |
| 5,314,991 A | 5/1994 | Oka et al. ........... 530/350 |
| 5,328,991 A | 7/1994 | Kuo ........... 530/403 |
| 5,389,368 A | 2/1995 | Curtiss, III |
| 5,449,669 A | 9/1995 | Metcalfe et al. ........... 514/13 |
| 5,480,972 A | 1/1996 | Avjioglu et al. ........... 530/379 |
| 5,486,452 A | 1/1996 | Gordon et al. ........... 435/5 |
| 5,496,554 A | 3/1996 | Oka et al. ........... 424/276.1 |
| 5,543,144 A | 8/1996 | Chang ........... 424/133.1 |
| 5,547,669 A | 8/1996 | Rogers et al. ........... 424/185.1 |
| 5,558,869 A | 9/1996 | Burks, Jr. et al. ........... 424/276.1 |
| 5,583,046 A | 12/1996 | Valenta et al. ........... 435/320.1 |
| 5,591,433 A | 1/1997 | Michael et al. ........... 424/184.1 |
| 5,597,895 A | 1/1997 | Gaynor et al. ........... 530/324 |
| 5,616,559 A | 4/1997 | Androphy et al. ........... 514/12 |
| 5,625,039 A | 4/1997 | Washida et al. ........... 530/388.25 |
| 5,637,454 A | 6/1997 | Harley ........... 435/5 |
| 5,648,242 A | 7/1997 | Valenta et al. ........... 435/69.3 |
| 5,652,122 A | 7/1997 | Frankel et al. ........... 435/69.7 |
| 5,667,965 A | 9/1997 | Androphy et al. ........... 435/5 |
| 5,670,617 A | 9/1997 | Frankel et al. ........... 563/300 |
| 5,674,980 A | 10/1997 | Frankel et al. ........... 530/350 |

(Continued)

FOREIGN PATENT DOCUMENTS

CA  2 157 596  9/1994
CA  2 158 047  9/1994

(Continued)

OTHER PUBLICATIONS

Finkelman et al., J Allergy Clin Immunol 120(3): 506-515, 2007.*
Li et al., J Allergy & Clinical Immunology 112(1): 159-167, 2003.*
Wood et al., Allergy 68(6): 803-808, Jun. 2013, abstract only.*
Dearman et al., Clin Exp Allergy 39: 458-468, 2009.*
Aalberse et al. J. Allergy Clin. Immunol. 106:228-238 (2000).
Blumental et al. Allergens and Allergen Immunotherapy, $3^{rd}$ Edition (2004).
Burk et al. Eur. J. Biochem. 245(2):334-339 (1997).
Chatel et al. Allergy 58:641-647 (2003).
Evans et al. FEMS Microbil. Immnol. 1(3):117-125 (1988).

(Continued)

*Primary Examiner* — Phuong Huynh
(74) *Attorney, Agent, or Firm* — Choate Hall & Stewart LLP

(57) ABSTRACT

The present invention provides methods and compositions for treating or preventing allergic responses, particularly anaphylactic allergic responses, in subjects who are allergic to allergens or susceptible to allergies. Methods of the present invention utilize administration of microorganisms to subjects, where the microorganisms produce allergens and protect the subjects from exposure to the allergens until phagocytosed by antigen-presenting cells. Particularly preferred microorganisms are gram-negative bacteria, gram-positive bacteria, and yeast. Particularly preferred allergens are proteins found in foods, venoms, drugs and latex that elicit allergic reactions and anaphylactic allergic reactions in individuals who are allergic to the proteins or are susceptible to allergies to the proteins. The proteins may also be modified to reduce the ability of the proteins to bind and crosslink IgE antibodies and thereby reduce the risk of eliciting anaphylaxis without affecting T-cell mediated Th1-type immunity.

2 Claims, 7 Drawing Sheets

(56) References Cited

U.S. PATENT DOCUMENTS

| | | | |
|---|---|---|---|
| 5,693,495 A | 12/1997 | Breiteneder et al. | 435/69.3 |
| 5,710,126 A | 1/1998 | Griffith et al. | 514/12 |
| 5,731,157 A | 3/1998 | Miller et al. | 435/7.4 |
| 5,736,149 A | 4/1998 | Avjioglu et al. | 424/275.1 |
| 5,747,641 A | 5/1998 | Frankel et al. | 530/300 |
| 5,759,572 A | 6/1998 | Sugimoto et al. | 424/450 |
| 5,773,003 A | 6/1998 | Swain et al. | 424/193.1 |
| 5,786,466 A | 7/1998 | Breiteneder et al. | 536/23.6 |
| 5,804,604 A | 9/1998 | Frankel et al. | 530/324 |
| 5,807,746 A | 9/1998 | Lin et al. | 435/375 |
| 5,811,128 A | 9/1998 | Tice et al. | |
| 5,820,862 A | 10/1998 | Garman et al. | 424/184.1 |
| 5,820,880 A | 10/1998 | Alving et al. | 424/450 |
| 5,830,463 A | 11/1998 | Duke et al. | 424/93.51 |
| 5,834,246 A | 11/1998 | Holmgren et al. | 435/69.7 |
| 5,837,550 A | 11/1998 | Breitenbach et al. | 436/513 |
| 5,843,672 A | 12/1998 | Morgenstern et al. | 435/7.1 |
| 5,843,710 A | 12/1998 | Cobon et al. | 435/69.1 |
| 5,869,040 A | 2/1999 | Oin | 424/93.21 |
| 5,888,762 A | 3/1999 | Joliot et al. | 435/69.1 |
| 5,888,799 A | 3/1999 | Curtiss, III | 435/252.3 |
| 5,891,432 A | 4/1999 | Hoo | 424/93.21 |
| 5,891,716 A | 4/1999 | Morgenstern et al. | 435/325 |
| 5,939,283 A | 8/1999 | Morgensterm et al. | 435/69.1 |
| 5,973,121 A | 10/1999 | Burks, Jr. et al. | 530/370 |
| 5,989,814 A | 11/1999 | Frankel et al. | 435/6 |
| 5,998,583 A | 12/1999 | Korsmeyer | 530/350 |
| 6,004,815 A | 12/1999 | Portnoy et al. | |
| 6,008,340 A | 12/1999 | Ball et al. | 536/23.6 |
| 6,025,162 A | 2/2000 | Rogers et al. | |
| 6,060,082 A | 5/2000 | Chen et al. | 424/450 |
| 6,086,898 A | 7/2000 | DeKruyff et al. | |
| 6,187,311 B1 | 2/2001 | Nishiyama et al. | |
| 6,218,371 B1 | 4/2001 | Krieg et al. | 514/44 |
| 6,221,648 B1 | 4/2001 | Le Page et al. | 435/252.3 |
| 6,239,116 B1 | 5/2001 | Krieg et al. | |
| 6,270,723 B1 | 8/2001 | Laugharn, Jr. et al. | |
| 6,486,681 B1 | 11/2002 | Burks, Jr. et al. | 536/23.6 |
| 6,506,388 B1 | 1/2003 | Shionoya et al. | |
| 6,902,743 B1 | 6/2005 | Setterstrom et al. | |
| 2002/0187158 A1 | 12/2002 | Mahler et al. | |
| 2003/0082190 A1 | 5/2003 | Saxon et al. | |
| 2005/0175630 A1 | 8/2005 | Raz | |

FOREIGN PATENT DOCUMENTS

| | | |
|---|---|---|
| EP | 0 080 806 | 6/1983 |
| EP | 0080806 A1 | 6/1983 |
| EP | 0 819 763 | 1/1998 |
| EP | 0684812 | 1/1998 |
| EP | 0877033 | 11/1998 |
| JP | 072 85875 | 4/1994 |
| JP | 06253851 | 9/1994 |
| JP | 07095887 | 4/1995 |
| WO | WO-8809669 | 12/1988 |
| WO | WO 90/04025 | 4/1990 |
| WO | WO 91/06571 | 5/1991 |
| WO | WO 91/11718 | 8/1991 |
| WO | WO 92/02621 | 2/1992 |
| WO | WO 92/03551 | 3/1992 |
| WO | WO 92/11859 | 7/1992 |
| WO | WO-9214487 | 9/1992 |
| WO | WO 93/21223 | 10/1993 |
| WO | WO 94/05303 | 3/1994 |
| WO | WO 94/10194 | 5/1994 |
| WO | WO 94/20614 | 9/1994 |
| WO | WO 94/23035 | 10/1994 |
| WO | WO 94/24281 | 10/1994 |
| WO | WO 95/07933 | 3/1995 |
| WO | WO 95/34578 | 12/1995 |
| WO | WO 96/14876 | 5/1996 |
| WO | WO-9614876 | 5/1996 |
| WO | WO 96/36880 | 11/1996 |
| WO | WO 97/05265 | 2/1997 |
| WO | WO 97/24139 | 7/1997 |
| WO | WO-9724139 | 7/1997 |
| WO | WO 98/23763 | 6/1998 |
| WO | WO-9823763 | 6/1998 |
| WO | WO 09/32866 | 7/1998 |
| WO | WO 98/43657 | 8/1998 |
| WO | WO 98/39029 | 9/1998 |
| WO | WO 98/44096 | 10/1998 |
| WO | WO-9844096 | 10/1998 |
| WO | WO 99/16467 | 4/1999 |
| WO | WO 99/25387 | 5/1999 |
| WO | WO 99/38978 | 5/1999 |
| WO | WO-9925387 | 5/1999 |
| WO | WO 99/34826 | 7/1999 |
| WO | WO 99/38978 | 8/1999 |
| WO | WO-9938978 | 8/1999 |
| WO | WO 99/49879 | 10/1999 |
| WO | WO 00/54803 | 9/2000 |
| WO | WO 01/36621 | 5/2001 |

OTHER PUBLICATIONS

Fenton et al. J. National Cancer Institute 87(24):1853-1861 (1995).
Gottieb et al. BMJ 318:894 (1999).
Ingram et al. J. Bacteriology 144(2):481-488 (1980).
Kleber-Janke et al. Protein Expression and Purification 19:419-424 (2000).
Komanapalli et al. Appl. Microbil. Biotechnol. 49:766-769 (1998).
Leclerc et al. J. Immunology 144(8):3174-3182 (1990).
Aalberse et al, 2000, J Allerg Clin Immunol, 106:228-38.
Andrews et al, 1996, Gene, 182:101-9.
Blumental et al, 2004, Allergens and Allergen Immunotherapy, 3rd Ed, 37-50.
Burks et al, 1995, J. Clin. Invest., 96:1715-21.
Burks et al, 1997, Eur J Biochem, 245:334-39.
Burks et al, 1999, Int Arch Allerg Immunol, 118:313-14.
Chatel et al, 2003, Allergy, 58:641-47.
Chong et al, 1997, Transgenic Res, 289-296.
Colman et al, 1994, Res Immunol, 145:33-36.
Dizier et al, 1999, Gen Epidemiol, 16:305-15.
Eidelman et al, 1988, Am Rev Respir Dis, 137:1033-37.
Eko et al, 1999, Vaccine, 17:1643-49.
Evans et al, 1998, FEMS Microbiol Immunol, 47:117-25.
Fasler et al, 1998, J Aller Clin Immunol, 101:521-30.
Fenton et al, 1995, J Natl Canc Inst, 87:1853-61.
Ferreira et al, 1996, J. Exp. Med., 183:599-609.
Ferreira et al, 1998, FASEB J, 12:231-42.
Gentschev et al, 1996, Gene, 179:133-40.
Gottlieb et al, 1999, BMJ, 318:894.
Greenspan et al, 1999, Nat Biotechnol, 17:936-37.
Hansen et al, 2000, J. Immunol., 164:223-30.
Harvey et al, 1990, Remington's Pharmaceutical Sciences, 18th Ed., Chapter 35, p. 711.
Hess et al, 1996, Proc Natl Acad Sci, USA, 93:1458-63.
Higgins et al, 1999, Mol Microbiol, 31:1631-41.
Hoffman et al, 1975, Immunochemistry, 12:535-38.
Ingram et al, 1980, J Bact, 144:481-88.
James et al, 1997, J Allerg Clin Immunol, 99(1):239-44 part 2.
Kleber-Janke et al, 2000, Prot Exp Purificat, 19:419-24.
Komanapalli et al, 1998, Appl Microbiol Biotechnol, 49:766-69.
Kraft et al, 1999, Intl Arch Allerg Immunol, 118:171-76.
Leclerc et al, 1990, J Immunol, 144:3174-82.
Li et al, 2003, J. Allergy Clin. Immunol., 112(1):160-167.
Li, 1999, J. Immunol., 162:3045-52.
Mekalanos, 1992, Gen Eng Vaccines, 327:43.
Rabjohn et al, 1999, J Clin Invest, 103:535-42.
Reese et al, 2005, J Immunol, 175:8354-64.
Skolnick et al, 2000, Trend Biotech, 18:34-39.
Stanley et al, 1997, Arch Biochem Biophys, 342:244-53.
Till, 2004, Allergens and Allergen Immunotherapy, 3rd Ed, 85-104.
Vrtala et al, 1995, Int Arch Allerg Immunol, 107:290-94.
Vrtala et al, 1997, J Clin Invest, 99(7):1673-81.
Walker et al, 1994, Vaccine, 12:387-400.
Yeung et al, 1998, J Immunol, 161:4146-52.

(56) References Cited

OTHER PUBLICATIONS

Chatel, et al., "Various Factors (Allergen Nature, Mouse Strain, CpG/Recombinant Protein Expressed) Influence the Immune Response Elicited by Genetic Immunization", *Allergy*, 58: 641-647, 2003.
Evans, et al., "Non-Replicating Oral Whole Cell Vaccine Protective Against Enterotoxigenic *Escherichia coli* (ETEC) Diarrhea: Stimuation of Anti-CFA (CFA/I) and Anti-Enterotoxin (Anti-LT) Intestinal IgA and Protection Against Challenge with ETEC Belonging to Heterologous Serotypes", *FEMS Microbiology Immunology*, 47: 117-126, 1988.
Gotlieb, "Scientists Develop Vaccine Strategy for Peanut Allergy", *BMJ*, 318: 894, 1999.
Vrtala, et al., "Conversion of the Major Birch Pollen Allergen, Bet v 1, into Two Nonanaphylactic T Cell Epitope-Containing Fragments", *J. Clin. Invest*. 99(7): 1673-1681, 1997.
Banks, et al., "Chemistry and Pharmacology of Honey-Bee Venom", *Venoms of the Hymenoptera*, 329-416, 1986.
Eko, et al., "New Strategies for Combination Vaccines Based on the Extended Recombinant Bacterial Ghost System", *Vaccine*, 17: 1643-1649, 1999.
Gentschev, et al., "Development of Antigen-Delivery Systems, Based on the *Escherichia coli* Hemolysin Secretion Pathway", Gene, 179: 133-140, 1996.
Hess, et al., "Superior Efficacy of Secreted Over Somatic Antigen Display in Recombinant *Salmonella* Vaccine Induced Protection Against Listeriosis", *Proc. Natl. Acad. Sci. USA*, 93: 1458-1463, 1996.
Koppelman, et al., "Peanut Allergen Ara h 3: Isolation from peanuts and biochemical characterization", *Allergy*, 58: 1144-1151, 2003.
Triozzi, et al., "Effects of a β-Human Chorionic Gonadotropin Subunit Immunogen Administered in Aqueous Solution with a Novel Nonionic Block Copolymer Adjuvant in Patients with Advanced Cancer", *Clinical Cancer Research*, 3: 2355-2362, 1997.
Amorim, et al., "Suppression of Airway Eosinophilia by Killed *Mycobacterium* Vaccae-Induced Allergen-Specific Regulatory T-Cells", *Nature Medicine*, 8(6): 625-629, 2002.
Asturias, et al., "Is Tropomyosin an Allergen in Anisakis?", *Allergy*, 55: 898-890, 2000.
Asturias, et al., "Cloning, Isolation, and IgE-Binding Properties of Helixaspersa (Brown Garden Snail) Tropomyosin", *Int. Arch Allergy Immunol*. 128: 90-96, 2002.
Asturias, et al., "Molecular Characterization of American Cockroach Tropomyosin (*Periplaneta americana* Allergen 7), a Cross-Reactive Allergen", *The Journal of Immunology*, 162: 4342-4348, 1999.
Bannon, et al., "Engineering, Characterization and in Vitro Efficacy of the Major Peanut Allergens for Use in Immunotherapy", *Int. Arch. Allergy Immunol*, 124: 70-72, 2001.
Barderas, et al., "Identification and Characterization of Che a 1 Allergen from *Chenopodium album* Pollen", *Int. Arch. Allergy Immunol*. 127: 47-54, 2002.
Barnes, P.J., "IL-10: A Key Regulator of Allergic Disease", *Clinical and Experimental Allergy*, 31: 667-669, 2001.
Bashir, et al., "An Enteric Helminth Infection Protects Against an Allergic Response to Dietary Antigen", *The Journal of Immunology*, 169: 3284-3292, 2002.
Batanero, et al., "Purification, Amino Acid Sequence and Immunological Characterization of Ole e 6, a Cysteine-Enriched Allergen from Olive Tree Pollen", *FEBS Letters*, 410: 293-296, 1997.
Beck, et al., "The Polyclonal and Antigen-Specific IgE and IgG Subclass Response of Mice Injected with Ovalbumin in Alum or Complete Freund's Adjuvant", *Cellular Immunology*, 123: 1-8, 1989.
Bissonnette, et al., "Inhibition of Mast Cell-Mediated Cytotoxicity by IFN-α/β and -γ$^1$", *The Journal of Immunology*, 145: 3385-3390, 1990.
Bock, et al., "The Natural History of Food Sensitivity", *J.Allergy Clin. Immunol*. 69: 173-177, 1982.
Bock, et al., "Fatalities Due to Anaphylactic Reactions to Foods", *J. Allergy Clin. Immunol*. 107: 191-193, 2001.

Brandtzaeg, et al., "Current Understanding of Gastrointestinal Immunoregulation and Its Relation to Food Allergy", *Ann. N.Y. Acad. Sci*., 964: 13-45, 2002.
Burks, et al., "Modification of a Major Peanut Allergen Leads to Loss of IgE Binding", *Int. Arch. Allergy Immunol*. 118: 313-314, 1999.
Bush, et al., "Molecular Cloning of a Major Alternaria Alternata Allergen, rAlt a 2", *J. Allergy Clin. Immunol*. 104: 665-671, 1999.
Chang, et al., "Characterization of Enolase Allergen from *Rhodotorula mucilaginosa*", *J. Biomed. Sci*. 9: 645-655, 2002.
Dandeu, et al., "Hydrophobic Interaction Chromatography for Isolation and Purification of Equ.cl, the Horse Major Allergen", *Journal of Chromatography*, 621: 23-31, 1993.
De Jong, et al., "Identification and Partial Characterization of Multiple Major Allergens in Peanut Proteins", *Clinical and Experimental Allergy*, 28: 743-751, 1998.
Diaz-Perales, et al., "Lipid-Transfer Proteins as Potential Plant Panallergens: Cross-Reactivity Among Proteins of *Artemisia* Pollen, *Castanea* Nut and *Rosaceae* Fruits, with Different IgE-Binding Capacities", *Clinical and Experimental Allergy*, 30: 1403-1410, 2000.
Diaz-Perales, et al., "Characterization of *Asparagus* Allergens: A Relevant Role of Lipid Transfer Proteins", *J. Allergy Clin. Immunol*. 110: 790-796, 2002.
Dorion, et al., "The Production of Interferon-γ in Response to a Major Peanut Allergy, Ara h II, Correlates with Serum Levels of IgE Anti-Ara h II", *J. Allergy Clin. Immunol*. 93: 93-99, 1994.
Durham, et al., "Immunologic Changes Associated with Allergen Immunotherapy", *The Journal of Allergy and Clinical Immunology*, 102(2): 157-164, 1998.
Erb, et al., "Atopic Disorders: A Default Pathway in the Absence of Infection?", *Immunol. Today*, 20: 317-322, 1999.
Eriksson, et al., "Cloning and Characterisation of a Group II Allergen from the Dust Mite *Tyrophagus putrescentiae*", *Eur. J Biochem*. 251: 443-447, 1998.
Eriksson, et al., "Cloning of Three New Allergens from the Dust Mite *Lepidoglyphus destructor* Using Phage Surface Display Technology", *Eur. J. Biochem*. 268: 287-294, 2001.
Fahlbusch, et al., "Purification and Partial Characterization of the Major Allergen, Cav p 1, from Guinea Pig *Cavia porcellus*", *Allergy*, 57: 417-422, 2002.
Fiorentino, et al., "Two Types of Mouse T Helper Cell", *J. Exp. Med*. 170: 2081-2095, 1989.
Francis, et al., "Induction of IL-10$^+$CD4$^+$CD25$^+$ T Cells by Grass Pollen Immunotherapy", *J. Allergy Clin. Immunol*. 111: 1255-1261, 2003.
Gafvelin, et al., "Cross-Reactivity Studies of a New Group 2 Allergen from the Dust Mite *Glycyphagus domesticus*, Gly d 2, and Group 2 Allergens from *Dermatophagoides pteronyssinus*, *Lepidoglyphus destructor*, and *Tyrophagus putrescentiae* with Recombinant Allergens", *J. Allergy Clin. Immunol*. 107: 511-518, 2001.
Giuliani, et al., "Isolation and Purification of a Major Allergen from *Parietaria officinalis* Pollen", *Allergy*, 42: 434-440, 1987.
Hansen, et al., "Vaccination with Heat-Killed *Listeria* as Adjuvant Reverses Established Allergen-Induced Airway Hyperreactivity and Inflammation: Role of CD8$^+$ T Cells and IL-18", *The Journal of Immunology*, 164: 223-230, 2000.
Helm, et al., "Isolation and Characterization of a Clone Encoding a Major Allergen (Bla g Bd9OK) Involved in IgE-Mediated Cockroach Hypersensitivity", *J. Allergy Clin. Immunol*. 98: 172-180, 1996.
Hilger, et al., "Sequence of the Gene Encoding cat (*Felis domesticus*) Serum Albumin", *Gene*, 169: 295-296, 1996.
Himly, et al., "Art v 1, the Major Allergen of Mugwort Pollen, is a Modular Glycoprotein with a Defensin-Like and a Hydroxyproline-Rich Domain", *FASEB J*., 17: 106-108, 2003.
Hoffman, et al., "Occupational Allergy to Bumblebees: Allergens of *Bombus terrestris*", *J. Allergy Clin. Immunol*. 108: 855-860, 2001.
Hoffman, et al., "Allergens in Hymenoptera Venom XXVII: Bumblebee Venom Allergy and Allergens", *J. Allergy Clin. Immunol*. 97: 812-821, 1996.
Hoffman, et al., "Allergens in Bee Venom, III. Identification of Allergen B of Bee Venom as an Acid Phosphatase", *J. Allergy Clin. Immunol*. 59(5): 364-366, 1977.

(56) References Cited

OTHER PUBLICATIONS

Horiuti, et al., "Variable Expression of Pathogenesis-Related Protein Allergen in Mountain Cedar (*Juniperus ashei*) Pollen", *The Journal of Immunology*, 164: 2188-2192, 2000.
Horner, et al., "Identfiication of the Allergen Psi c 2 from the Basidiomycete *Psilocybe cubensis* as a Fungal Cyclophilin". *Int. Arch Allergy Immuno*l. 107: 298-300, 1995.
Howard, et al., "Regulation of B-Cell Growth and Differentiation by Soluble Factors", *Ann. Rev. Immunol.* 1: 307-333, 1983.
Hsu, et al., "Differential Effects of IL-4 and IL-4 and IL-10 on IL-2-Induced IFN-$\gamma$ Synthesis and Lymphokine-Activated Killer Activity", *International Immunology*, 4(5): 563-569, 1992.
Ichikawa, et al., "Molecular Cloning, Expression and Modelling of Cat Allergen, Cystatin (Fel d 3), A Cysteine Protease Inhibitor", *Clinical and Experimental Allergy*, 31: 1279-1286, 2001.
Jankulovic, et al.. "Isolation and Biochemical Characterization of a Thaumatin-Like Kiwi Allergen", *J. Allergy Clin. Immunol.* 110: 805-810, 2002.
Kalliomaki, et al., "Transforming Growth Factor-$\beta$ in Breast Milk: A Potential Regular of Atopic Disease at an Early Age", *J. Allergy Clin. Immunol.* 104(6): 1251-1257, 1999.
Kleine-Tebbe, et al., "Severe Oral Allergy Syndrome and Anaphylactic Reactions Caused by a Bet v 1-Related PR-10 Protein in Soybean, SAM22", *J. Allergy Clin. Immunol.* 110: 797-804, 2002.
Kowalski, et al., "Mechanisms of Specific Immunotherapy of Allergic Diseases", *Allergy*, 53: 485-492, 1998.
Ledesman, et al., "Cloning, Expression and Characterization of a Novel Four EF-Hand $Ca^{2+}$—Binding Protein from Olive Pollen with Allergenic Activity", *FEBS Letter*, 466: 192-196, 2000.
Lee, et al., "Oral Administration of Il-12 Suppresses Anaphylactic Reactions in a Murine Model of Peanut Hypersensitivity", *Clinical Immunology*, 101(2): 220-228, 2001.
Leung, et al., "Effect of Anti-IgE Therapy in Patients with Peanut Allergy", *N. Engl. J. Med.* 348: 986-993, 2003.
Li, et al., "A Murine Model of Peanut Anaphylaxis: T- and B-Cell Responses to a Major Peanut Allergen Mimic Human Responses", *J. Allergy Clin. Immunol.* 106: 150-158, 2000.
Li, et al., "Novel Approaches for the Treatment of Food Allergy", *Current Opinion in Allergy and Clinical Immunology*, 2: 273-278, 2002.
Li, et al., "Engineered Recombinant Peanut Protein and Heat-Killed *Listeria* Monocytogenes Coadministration Protects Against Peanut-Induced Anaphylaxis in a Murine Model", *The Journal of Immunology*, 170: 3289-3295, 2003.
Li, et al., "Strain-Dependent Induction of Allergic Sensitization Caused by Peanut Allergen DNA Immunization in Mice", *The Journal of Immunology*, 162: 3045-3052, 1999.
Lombardero, et al., "cDNA Sequence Analysis of the Main Olive Allergen, Ole e I", *Clinical and Experimental Allergy*, 24: 765-770, 1994.
Lopata, et al., "Characteristics of Hypersensitivity Reactions and Identification of a Unique 49 kd IgE-Binding Protein (Hal-m-1) in Abalone (*Haliotis midae*)", *J. Allergy Clin. Immunol.* 100: 642-648, 1997.
Lorentz, et al., "Human Intestinal Mast Cells Produce IL-5 in Vitro Upon IgE Receptor Cross-Linking and In Vivo in the Course of Intestinal Inflammatory Disease" *Eur. J. Immunol.* 29: 1496-1503, 1999.
Melen, et al., "Molecular Cloning of Per a 1 and Definition of the Cross-Reactive Group 1 Cockroach Allergens", *J. Allergy Clin. Immunol.* 103: 859-864, 1999.
Moneo, et al., "Isolation and Characterization of Tha p 1, A Major Allergen from the Pine Processionary Caterpillar *Thaumetopoea pityocampa*", *Allergy*, 58: 34-37, 2003.
Moneo, et al., "Isolation and Characterization of a Major Allergen from the Fish Parasite *Anisakis simplex*", *J Allergy Clin. Immunol.* 106: 177-182, 2000.
Monsalve, et al.. "Detection, Isolation and Complete Amino Acid Sequence of an Aeroallergenic Protein from Rapeseed Flour", *Clinical and Experimental Allergy*, 27: 833-841, 1997.

Morafo, et al., "Genetic Susceptibility to Food Allergy is Linked to Differential $T_H^2$-$T_H^1$ Responses in C3H/HeJ and BALB/c Mice", *J Allergy Clin. Immunol.* 111: 1122-1128, 2003.
Mosmann, et al., "Thi and Th2 Cells: Different Patterns of Lymphokine Secretion Lead to Different Functional Properties", *Ann. Rev. Immunol.* 7: 145-173, 1989.
Mutius, et al., "The Environmental Predictors of Allergic Disease", *J. Allergy Clin. Immunol.* 105: 9-19, 2000.
Onishi, et al., "Two-Dimensional Electrophoresis of Malassezia Allergens for Atopic Dermatitis and Isolation of Mal f 4 Homologs with Mitochondrial Malate Dehydrogenase", *Eur. J. Biochem.* 261: 148-154, 1999.
Onizuka, et al., "Purification of the Major Allergen of Red Soft Coral (*Dendronephthya nipponica*)", *Int. Arch. Allergy Immunol*, 125: 135-143, 2001.
Oppenheimer, et al., "Treatment of Peanut Allergy with Rush Immunotherapy", *J. Allergy Clin. Immunol.* 90: 256-262, 1992.
Paddock, et al., "Identification, Cloning, and Recombinant Expression of Procalin, a Major Triatomine Allergen", *The Journal of Immunology*, 167: 2694-2699, 2001.
Palosuo, et al., "Wheat $\omega$-5 Gliadin is a Major Allergen in Children with Immediate Allergy to Ingested Wheat", *J. Allergy Clin. Immunol.* 108: 634-638, 2001.
Pastorello, et al., "The Major Allergen of Sesame Seeds (*Sesamum indicum*) is a 2S Albumin", *Journal of Chromatography B*, 756: 85-93, 2001.
Pastorello, et al., "Allergenic Cross-Reactivity Among Peach, Apricot, Plum, and Cherry in Patients with Oral Allergy Syndrome: An In Vivo and in Vitro Study", *J. Allergy Clin. Immunol.* 94: 699-707, 1994.
Pierkes, et al., "Decreased Release of Histamine and Sulfidoleukotrienes by Human Peripheral Blood Leukocytes After Wasp Venom Immunotherapy is Partially Due to Induction of IL-10 and IFN-$\gamma$ Production of T Cells", *J. Allergy Clin. Immunol.* 103: 326-332, 1999.
Pomes, et al., "Novel Allergen Structures with Tandem Amino Acid Repeats Derived from German and American Cockroach", *The Journal of Biological Chemistry*, 273(46): 30801-30807, 1998.
Ramos, et al., "cDNA Cloning and Expression of Blo t 11, the *Blomia tropicalis* Allergen Homologous to Paramyosin", *Int. Arch. Allergy Immunol.* 126: 286-293, 2001.
Rasool, et al., "Cloning, Characterization and Expression of Complete Coding Sequences of Three IgE Binding *Malassezia furfur* Allergens, Mal f 7, Mal f 8 and Mal f 9", *Eur. J. Biochem.* 267: 4355-4361, 2000.
Romagnani, et al., "The Role of Lymphocytes in Allergic Disease", *J. Allergy Clin. Immunol.* 105: 399-408, 2000.
Rook, et al., "Give us this Day our Daily Germs", *Immunology Today*, 19: 113-116, 1998.
Saarinen, et al., "Transforming Growth Factor-$\beta$1 in Mothers' Colostrum and Immune Responses to Cows' Milk Proteins in Infants with Cows' Milk Allergy", *J. Allergy Clin. Immunol.* 104: 1093-1098, 1999.
Saarne, et al., "Cloning and Characterisation of Two IgE-Binding Proteins, Homologous to Tropomyosin and $\alpha$-Tubulin, from the *Lepidoglyphus destructor*", *Int. Arch Allergy Immunol.* 130: 258-265, 2003.
Sampson, et al., "Fatal and Near-Fatal Anaphylactic Reactions to Food in Children and Adolescents", *N. Engl. J. Med.* 327: 380-384, 1992.
Sampson, Hugh., "Food Allergy. Part 1: Immunopathogenesis and Clinical Disorders", *The Journal of Allergy and Clinical Immunology*, 103(5): 717-728, 1999.
Sanchez-Monge, et al., "Isolation and Characterization of Relevant Allergens from Boiled Lentils", *J. Allergy Clin. Immunol.* 106: 955-961, 2000.
Santos, et al., "Cockroach Allergens and Asthma in Brazil: Identification of Tropomyosin as a Major Allergen with Potential Cross-Reactivity with Mite and Shrimp Allergens", *J. Allergy Clin. Immunol.* 104: 329-337, 1999.
Saxena, et al., "cDNA Cloning, Expression and Characterization of an Allergenic L3 Ribosomal Protein of *Aspergillus fumigatus*" *Clin. Exp. Immunol*, 134: 86-91, 2003.

(56) References Cited

OTHER PUBLICATIONS

Schade, et al., "Differences in Antigen-Specific T-Cell Responses Between Infants with Atopic Dermatitis with and without Cow's Milk Allergy: Relevance of $T_H2$ Cytokines", *J. Allergy Clin. Immunol.* 106: 1155-1162, 2000.
Shen, et al., "Characterization of Allergens from *Penicillium oxalicum* and *P. notatum* by Immunoblotting and N-Terminal Amino Acid Sequence Analysis", *Clinical and Experimental Allergy*, 29: 642-651, 1999.
Shen, et al., "Molecular Cloning and Immunological Characterization of the House Dues Mite Allergen Der f 7", *Clinical and Experimental Allergy*, 25: 1000-1006, 1995.
Sicherer, et al., "Prevalence of Peanut and Tree Nut Allergy in the US Determined by a Random Digit Dial Telephone Survey", *J. Allergy Clin. Immunol.* 103: 559-562, 1999.
Smith, et al., "Sequence Polymorphisms and Antibody Binding to the Group 2 Dust Mite Allergens", *Int. Arch. Allergy Immunol.* 124: 61-63, 2001.
Smith, et al., "The Molecular Basis of Antigenic Cross-Reactivity Between the Group 2 Mite Allergens", *J. Allergy Clin Immunol.* 107: 977-984, 2001.
Snapper, et al., "Interferon-γ and B Cell Stimulatory Factor-1 Reciprocally Regulate Ig Isotype Production", *Science*, 236: 944-947, 1987.
Sommergruber, et al., "Molecular Characterization of Dau c 1, the Bet v 1 Homologous Protein from Carrot and its Cross-Reactivity with Bet v 1 and Api g 1", *Clinical and Experimental Allergy*, 29: 840-847, 1999.
Stanley, et al., "Identification and Mutational Analysis of the Immunodominant IgE Binding Epitopes of the Major Peanut Allergen Ara h 2", *Archives of Biochemistry and Biophysics*, 342(2): 244-253, 1997.
Strobel, et al., "Immune Responses to Dietary Antigens: Oral Tolerance", *Immunology Today*, 19: 173-181, 1998.
Strobel, et al., "Oral Tolerance, Systemic Immunoregulation, and Autoimmunity" *Ann. N. Y. Acad. Sci.* 958: 47-58, 2002.
Tejera, et al., "Identification, Isolation, and Characterization of Ole e 7, a New Allergen of Olive Tree Pollen", *J. Allergy Clin Immunol*, 104: 797-802, 1999.
Tinghino, et al., "Molecular Characterization of a Cross-Reactive *Juniperus oxycedrus* Pollen Allergen, Jun o 2: A Novel Calcium-Binding Allergen", *J. Allergy Clin Immunol*, 101: 772-777, 1998.
Tsai, et al., "Sequence Analysis and Expression of a cDNA Clone Encoding a 98-kDa Allergen in *Dermatophagoides farinae*", *Clinical and Experimental Allergy*, 29: 1606-1613, 1999.
Turcanu, et al., "Characterization of Lymphocyte Responses to Peanuts in Normal Children, Peanut-Allergic Children, and Allergic Children who Acquired Tolerance to Peanuts", *The Journal of Clinical Investigation*, 111(7): 1065-1072, 2003.
Weiner, et al., "Oral Tolerance: Immune Mechanisms and Treatment of Autoimmune Diseases", *Immunology Today*, 18: 335-343, 1997.
Wopfner, et al., "Molecular and Immunological Characterization of Profilin from Mugwort Pollen", *Biol. Chem.* 383: 1779-1789, 2002.
Wu, et al., "Sequencing Analysis of cDNA Clones Encoding the American Cockroach Cr-PI Allergens", *The Journal of Biological Chemistry*, 271(30): 17937-17943, 1996.
Wu, et al., "Cloning of the American Cockroach Cr-PII Allergens: Evidence for the Existence of Cross-Reactive Allergens Between Species", *J. Allergy Clin. Immunol*, 101: 832-840, 1998.
Wu, et al., "Sequencing and Immunochemical Characterization of the American Cockroach Per a 3 (Cr-PI) Isoallergenic Variants", *Molecular Immunology*, 34(1): 1-8, 1997.
Xu, et al., "Cloning, Expression and Immunological Characterization of Ory s 1, the Major Allergen of Rice Pollen", *Gene*, 164: 255-259, 1995.
Yasueda, et al., "Identification and Cloning of Two Novel Allergens from the Lipophilic Yeast, *Malassezia furfur*", *Biochemical and Biophysical Research Communications*, 248: 240-244, 1998.

Yeung, et al., "Heat-Killed *Listeria* Monocytogenes as an Adjuvant Converts Established Murine Th2-Dominated Immune Responses into Th1-Dominated Responses", *The Journal of Immunology*, 161: 4146-4152, 1998.
Yi, et al., "Identification of Shared and Unique Immunoglobulin E Epitopes of the Highly Conserved Tropomyosins in *Blomia tropicalis* and *Dermatophagoides pteronyssinus*", *Clin. Exp. Allergy*, 32: 1203-1210, 2002.
Yocum, et al., "Epidemiology of Anaphylaxis in Olmsted County: A Population-Based Study", *J. Allergy Clin. Immunol.* 104: 452-456, 1999.
Yokoyama, et al., "Purification, Identification, and cDNA Cloning of Jun a 2, the Second Major Allergen of Mountain Cedar Pollen", *Biochemical and Biophysical Research Communications*, 275: 195-202, 2000.
Yu, et al., "Proteomics and Immunological Analysis of a Novel Shrimp Allergen, Pen M 2", *The Journal of Immunology*, 170: 445-453, 2003.
Hansen, "Vaccination with Heat-Killed *Listeria* as Adjuvant Reverses Established Allergen-Induced Airway Hyperreactivity and Inflammation: Role of $CD8^+$ T Cells and IL-18", *The Journal of Immunology*, 164: 223-230, 2000.
Mekalanos, "Bacterial Mucosal Vaccines" in Genetically Engineered Vaccines, Edited by Ciardi et al., Plenum Press, pp. 43-50, 1992.
Burks, et al., "Epitope Specificity of the Major Peanut Allergen, Ara h II", *J. Allergy Clin. Immunol.* 95: 607-611, 1995.
Gayler, et al., "Biosynthesis, cDNA and Amino Acid Sequences of a Precursor of Conglutin δ, a Sulphur-Rich Protein from *Lupinus angustifolius*", *Plant Molecular Biology*, 15: 879-893, 1990.
Del Val, et al., "Thioredoxin Treatment Increases Digestibility and Lowers Allergenicity of Milk", *J. Allergy Clin. Immunol.* 103(4): 690-697, 1999.
Hoyne, et al., "Peptide-Mediated Regulation of the Allergic Immune Response", *Immunol. Cell Biol.* 74(2): 180-186, 1996.
Vailes, et al., "Fine Specificity of B-Cell Epitopes on *Felis domesticus* Allergen I (Fel d I): Effect of Reduction and Alkylation or Deglycosylation of Fel d I Structure and Antibody Binding", *J Allergy Clin. Immunol.* 93(1): 22-33, 1994.
Burns, et al., "Selective Reduction of Disulfides by Tris (2-Carboxyethyl) Phosphine", *J. Org. Chem.* 56(8): 2648-2650, 1991.
Gray, et al., "Echistatin Disulfide Bridges: Selective Reduction and Linkage Assignment", *The Protein Society*, 1749-1755, 1993.
Ichikawa, et al., "Solution Structure of Der f 2, the Major Mite Allergen for Atopic Disease", *J. Mol. Chem.*, 273: 356-360, 1998.
Medaglini, et al., "Mucosal and Systemic Immune Responses to a Recombinant Protein Expressed on the Surface of the Oral Commensal Bacterium *Streptococcus gordonii* After Oral Colonization", *Proceedings of the National Academy of Sciences of the United States of America*, 92(15): 6868-6872, 1995.
Nishiyama, et al., "Analysis of the IgE-epitope of Der f 2, a Major Mite Allergen, by in vitro Mutagenesis", *Mol. Immunol.*, 32: 1021-1029, 1995.
Nishiyama, et al., "Effects of Amino Acid Variations in Recombinant Der f II on its Human IgE and Mouse IgG Recognition", *Int. Arch. Allergy Immunol.*, 105: 62-69, 1994.
Takai, et al., "Effect of Proline Mutations in the Major House Dust Mite Allergen Der f 2 on IgE-binding and Histamine-releasing Activity", *Eur. J. Biochem.*, 267: 6650-6656, 2000.
Takai, et al., "Non-anaphylactic Combination of Partially Deleted Fragments of the Major House Dust Mite Allergen Der f 2 for Allergen-specific Immunotherapy", *Mol. Immunol.*, 36: 1055-1065, 1999.
Takai, et al., "Determination of the N- and C-terminal Sequences to Bind Human IgE of the Major House Dust Mite Allergen Der f 2 and Epitope Mapping for Monoclonal Antibodies", *Mol. Immunol.*, 34: 255-261, 1997.
Takai, et al., "Engineering of the Major House Dust Mite Allergen Der f 2 for Allergen-specific Immunotherapy", *Nat. Biotechnol.*, 15: 754-758, 1997.
Vrtala, et al., "Humoral Immune Responses to Recombinant Tree Pollen Allergens (Bet v 1 and Bet v II) in Mice: Construction of a Live Oral Allergy Vaccine", *International Archives of Allergy and Immunology*, 107: (1-3): 290-294, 1995.

(56) References Cited

OTHER PUBLICATIONS

EMBL Accession No. L77197 (Mar. 1996).
Gray, et al., "Disulfide Structures of Highly Bridged Peptides: A New Strategy for Analysis", *The Protein Society*,1732-1748, 1993.
Herbert, et al., "Reduction and Alkylation of Proteins in Preparation of Two-Dimensional Map Analysis: Why, When, and How?"*Electrophoresis*, 22: 2046-2057, 2001.
Nakamura, et al., "Mass Spectrometric-Based Revision of the Structure of a Cysteine-Rich Peptide Toxin with Gamma-Carboxyglutamic Acid, TxVIIA, from the Sea Snail, *Conus textile*", *Protein Science*, 5(3): 524-530, 1996.
Olsson, et al., "Contribution of Disulphide Bonds to Antigenicity of Lep d 2, the Major Allergen of the Dust Mite *Lepidoglyphus destructor*", *Molecular Immunology*, 35: 1017-1023, 1998.
Smith, et al., "Localization of Antigenic Sites on Der p 2 Using Oligonucleotide-Directed Mutagenesis Targeted to Predicted Surface Residues", *Clinical and Experimental Allergy*, 27:.593-599, 1997.
Smith, et al., "Recombinant Allergens for Immunotherapy: A Der p 2 Variant with Reduced IgE Reactivity Retains T-Cell Epitopes", *J. Allergy Clin. Immunol*. 101(3): 423-425, 1998.
Smith, et al., "Reduction in IgE Binding to Allergen Variants Generated by Site-Directed Mutagenesis: Contribution of Disulfide Bonds to the Antigenic Structure of the Major House Dust Mite Allergen Der p 2", *Molecular Immunology*, 33(4/5): 399-405, 1996.
Watson, et al., "Trapping and Identification of Folding Intermediates of Disulfide Bond-Forming Proteins Based on Cyanylation, Cleavage, and Analysis by Mass Spectrometry", http:/www.abrf.org/JBT/Articles/JBT0014/JBT0014.html. pp. 1-12.
Wu, et al., "A Novel Methodology for Assignment of Disulfide Bond Pairing in Proteins", *Protein Science*, 6(2): 391-398, 1997.
Zhou, et al., "Assignment of Disulfide Bonds in Proteins by Partial Acid Hydrolysis and Mass Spectrometry", *Journal of Protein Chemistry*, 9(5): 523-532, 1990.
U.S. Appl. No. 07/998,377, filed Dec. 30, 1992.
U.S. Appl. No. 08/158,704, filed Nov. 29, 1993.
U.S. Appl. No. 08/610,424, filed Mar. 4, 1996.
U.S. Appl. No. 09/015,657, filed Jan. 28, 1999.
U.S. Appl. No. 09/336,463, filed Jun. 18, 1999.
U.S. Appl. No. 60/009,455, Dec. 29, 1995.
U.S. Appl. No. 08/717,933, filed Sep. 23, 1996.
U.S. Appl. No. 09/106,872, filed Jun. 29, 1998.
U.S. Appl. No. 60/077,763, filed Mar. 13, 1998.
Aas, et al., "Physico-Chemical Properties and Specific Activity of a Purified Allergen (Codfish)", *Dev. Biol. Stand*. 29: 90-98, 1975.
Aki, et al., "Immunochemical Characterization of Recombinant and Native Tropomyosins as a New Allergen from the House Dust Mite, *Dermatophagoides farinae*", *J. Allergy Clin. Immunol*., 96:74-83, 1995.
Alenius, et al., "Prohevein from the Rubber Tree (*Hevea brasiliensis*) is a Major Latex Allergen," *Clin. Exp. Allergy*, 25(7): 659-665, 1995.
Alenius, et al., "The Main IgE-Binding Epitope of a Major Latex Allergen, Prohevein, is Present in its N-Terminal 43-Amino Acid Fragment, Hevein" *J. Immunol*. 156(4): 1618-1625, 1996.
Alenius, et al., "IgE Reactivity to 14-kD and 27-kD Natural Rubber Proteins in Latex-Allergic Children with Spina Bifida and Other Congenital Anomalies", *Int. Arch. Allergy Immunol*., 102:61-66, 1993.
Ansari, et al., "An Investigation of Human Response to Pereninal Ryegrass", *J. Allergy Clin. Immunol*. 80: 229-235, 1987.
Ansari, et al., "Complete Amino Acid Sequence of a *Lolium perenne* (Perennial Rye Grass) Pollen Allergen, Lol p II" *J. Biol. Chem*., 264:11181-11185, 1989.
Ansair, et al., "Complete Primary Structure of a *Lolium perenne* (Perrennial Rye Grass) Pollen Allergen, Lol p III: Comparison with Known Lol P I and II Sequences", *Biochemistry*, 28:8665-8670, 1989.
Apold, et al., "The Allergenic Structure of Allergen M from Cod. III. Studies on the Antigenic of Long-Sequence Peptides", *Int Arch Allergy Appl Immunol*. 58(3): 337-43, 1979.

Arruda, et al., "Molecular Cloning of a Major Cockroach (*Blattella germanica*) Allergen, Bla g 2", *J. Biol. Chem*., 270:19563-19568, 1995.
Arruda, et al., "Cloning of Cockroach Allergen, Bla g 4, Identifies Ligand Binding Proteins (or Calycins) as a Cause of IgE Antibody Responses" *J. Biol. Chem*. 270: 31196-31201, 1995.
Arruda, et al., "Molecular Cloning of German Cockroach (*Blattella germanica*) Allergens", *Int. Arch Allergy Immunol*., 107:295-297, 1995.
Asturias, et al., "Cloning and High Level Expression of *Cynodon Dactylon* (Bermuda Grass) Pollen Profilin (Cyn d 12) in *Escherichia coli*: Purification and Characterization of the Allergen" *Clin. Exp. Allergy*, 27:1307-1313, 1997.
Asturias, et al., "Cloning and Expression of the Panallergen Profilin and the Major Allergen (Ole e 1) from Olive Tree Pollen", *J. Allergy Clin Immunol* 100:365-372, 1997.
Attanayaka, et al., "Molecular Cloning and Nucleotide Sequencing of the Rubber Elongation Factor Gene from *Hevea brasilienis*", *Plant Mol. Biol*., 16:1079-1081, 1991.
Aukrust, L., "Purification of Allergens in *Cladosporium herbarum*", Allergy, 35: 206-207, 1980.
Aukrust, et al., "Partial Purification and Characterization of Two *Cladosporium herbarum* Allergens", *Int Arch Allergy Appl Immunol*., 60:68-79, 1979.
Avjioglu, et al.,"Sequence Analysis of Sor H I, The Group I Allergen of Johnson Grass Pollen and Its Comparison to Rye-Grass Lol P I" *J. Allergy Clin. Immunol*. 91:340.
BSAC Working Party, "Position Paper on Allergen Immunotherapy," *Clin. Exp. Allergy*, 23: 1-44 (1993).
Ball, et al., "A Major Continuous Allergenic Epitope of Bovine Beta-Lactoglobulin Recognized by Human IgE Binding", *Clin. Exp. Allergy*, 24: 758-764, 1994.
Bannon, et al., "Tertiary Structure and Biophysical Properties of a Major Peanut Allergen, Implications for the Production of a Hypoallergenic Protein", *Int. Arch Allergy Immunol*. 118(2-4), 315-6, Feb.-Apr. 1999.
Bannon, et al., "Ara h 3, A Peanut Allergen Identified by Using Peanut Sensitive Patient Sera Adsorbed with Soy Proteins" Abstract.
Barnett, et al., "Multiplicity of Allergens in Peanuts," *J. Allergy Clin. Immunol*., 72: 61-8, 1983.
Barnett, et al., "Partial Characterization of an Allergenic Glycoproteins from Peanut", *Biochimica et Biophysica Acta* 882: 97-105, 1986.
Batanero, et al., "Ole e 3, an Olive-Tree Allergen, Belongs to a Widespread Family of Pollen Proteins" *Eur. J. Biochem*., 241:772-778, 1996.
Bauer, et al., "Modulation of the Allergic Immune Response in BALB/c Mice by Subcutaneo Injection of High Doses of the Dominant T Cell Epitope from the Major Birch Pollen Allergen Bet v 1", *Clin Exp Immunol*, 107(3): 536-41, Mar. 1997.
Bayard, et al., "Mapping of IgE Binding Regions in the Major Rat Urinary Protein, Alpha 2u-Globulin, Using Overlapping Peptides", *Immunol. Invest*, 28(5-6): 323-38, Sep.-Dec. 1999.
Bernhisel-Broadbent, et al., "Cross-Allergenicity in the Legume Botanical Family in Children with Food Hypersensitivity. II. Laboratory correlates" *J Allergy Clin. Immunol*., 84: 701-709 (1989).
Bevier, "Flea Allergy Dermatitis Testing Breakthrough", *Canine Practice*, 22(2-3): 49-50, 1997.
Birkner, et al., "Evaluation of Immunotherapy-Induced Changes in Specific IgE, IgG, and IgG—subclasses in Birch Pollen-Allergic Patient by Means of Immunoblotting, Correlation with Clinical Response," *Allergy*, 45: 418-426.
Bock, "Natural History of Severe Reactions to Foods in Young Children," *J. Pediatr*. 107: 676-680, 1985.
Bock, "The Natural History of Peanut Allergy", *J. Allergy Clin. Immunol*., 83: 900-904 (1989).
Botros, H., "Cross-Antigenicity of Horse Serum Albumin with Dog and Cat Albumins: Study of Three Short Peptides with Siginificant Inhibitory Activity Towards Specific Human IgE and IgG Antibodies", *Immunology*, 88: 340-47, 1996.
Boulet, et al., "Inhibitory Effects of an Anti-IgE Antibody E25 on Allergen-Induced Early Asthmatic Response," *Am J. Respir Crit Care Med*., 155: 1835-1840, 1997.

(56) References Cited

OTHER PUBLICATIONS

Brand, et al., "Allergen-Specific Immune Deviation from a TH2 to TH1 Response Induced by Dendritic Cells and Collagen Type 1", *J. Allergy Clin. Immunol.* 104(5): 1052-58, Nov. 1999.

Breiteneder, et al., "Diversity of Human T Cell Receptor Sequences of T Cell Clones with Specificit Bet v 1 Peptide/MHC II Complexes", *Adv Exp Med Biol.* 409:365-74, 1996.

Breiteneder, et al., "Four Recombinant Isoforms of Cor a I, the Major Allergen of Hazel Pollen, Show Different IgE-Bjnding Properties", *Europ. J. Biochem.* 212:355-362, 1993.

Breiteneder, et al., "Complementary DNA Cloning and Expression in *Escheria coli* of Ali g 1, the Major Allergen in Pollen odf alder (*Alnus glutinosa*)," J. Allergy Clin. Immunol., 90: 909-917 (1992).

Briner, et al., "Peripheral T-Cell Tolerance Induced in Naive and Primed Mice by Subcutaneo Injection of Peptides From the Major Cat Allergen Fel D I", *Proc. Natl Acad Sci USA*, 90(16): 7608-12, Aug. 15, 1993.

Bulone, A., "Separation of Horse Dander Allergen Proteins by Two-Dimensional Electrophoresis Molecular Characterisation and Identification of Equ c 2.0101 and Equ c 2.0102 as Lipocalin Proteins", *Eur J. Biochem.*, 253:202-211, 1998.

Burks, et al., "Allergeicity of Peanut and Soybean Extracts Altered by Chemical or Thermal Denaturation in Patients with Atopic Dermatitis and Positive Food Challenges", *J. Allergy Clin Immunol*, 90(6 pt 1): 889-97, 1992.

Burks, et al., "Anaphylactic Reactions Following Gammaglibulin Administration in Patients with Hypgammaglobulinema: Detection of IgE antibodies to IgA," *N. Eng. J. Med.* 314: 560-4, 1986.

Burks, et al., "Antibody Response to Milk Proteins in Patients with Milk-Protein Intolerance Documented by Challenge," *J. Allergy Clin. Immunol.* 85: 921-7, 1990.

Burks, et al., "Atopic Dermatitis: Clinical Relevance of Food Hypersensitivity Reactions", *J. Pediatr.*113: 447-451, 1988.

Cloning of the Ara H II Peanut Allergen by Polymerase Chain Reaction (PCR) Amplification, Abstract.

Burks, et al,, "The Identification of a Family of Vicilin-Like Genes Encoding Allergens Responsible for Peanut Hyper-Sensitivity", Abstract.

Burks, et al., Epitope Specificity and Immunoaffinity Purification of the Major Peanut Allergen, Ara h 1, , *J. Allergy Clin Immunol.* 93(4): 743-50 (1994).

Burks, et al., "Identification and Characterization of a Second Major Peanut Allergen, Ara h II, with Use of the Sera of Patients with Atopic Dermatitis and Positive Peanut Challenge," *J Allergy Clin Immunol..* 90(6 pt 1):962-9 (1992).

Burks, et al., "Identification of a Second Major Peanut Allergen in Patients with Atopic Dermatitis and Peanut Hypersensivity," *J. Allergy Clin. Immunol.* 87:211, 1991.

Burks, et al., "Identification of Peanut Agglutinin and Soybean Trypsin Inhibitor as Minor Legume Allergens," *Int Arch Allergy Immunol.* 105(2): 143-9, 1994.

Burks, et al., "Identification of a Major Peanut Allergen Ara h 1, in Patients with Atopic Dermatitis and Positive Peanut Challenge," *J Allergy Clin. Immunol.* 88, 172-179, 1991.

Burks, et al., "Isolation, Identification, and Characterization of Clones Encoding Antigens Responsible for Peanut Hypersensitivity", *Int. Arch. Allergy Immunol.* 107(1-3): 248-50, May-Jun. 1995.

Burks, et al., "Mapping and Mutational Analysis of the IgE-Binding Epitopes on Ara h 1, a Legume Vicilin Protein and a Major Allergen in Peanut Hypersensitvity", *Eur J. Biochem.* 245(2): 334-9, Apr. 1997.

Burks, et al., "Modification of a Major Peanut Allergen Leads to Loss of IgE Binding", *Int. Arch Allergy Immunol.* 118(2-4), 313-4, Feb.-Apr. 1999.

Burks, et al., "Peanut Allergens", Allergy, 53(8): 725-30, Aug. 1998.

Burks, et al., Production of Murine Monoclonal (mAb) Antibodies to Ara H1, A 63.5 kD Allergen in Peanuts, *J. Allergy Clin. Immunol.* 87: 210, 1991.

Burks, et al., "Recombinant Peanut Allergen Ara h I Expression and IgE Binding in Patients with Peanut Hypersensitivity", *J. Clin. Invest.* 96(4): 1715-21, Oct. 1996.

Burks, et al., "Cloning, Epitope Mapping and Mutational Analysis of Ara H 2, A Major Peanut Allergen", Abstract.

Butch, et al., "Properties of Human Follicular Dendritic Cells Purified with HJ2, a New Monoclonal Antibody", *Cellular Immunology*, 155, 27-41 (1994).

Cardaba, et al., "Antibody Response to Olive Pollen Antigens: Association Between HLA Class II Genes and IgE Response to Ole e I" *J. Allergy Clin. Immunol.* 91:338, 1993.

Chaloin, et al., "Conformations of Primary Amphipathic Carrier Peptides in Membrane Mimicking Environments", *Biochemistry*, 36: 11179-11187, 1997.

Chapman, et al., "Purification of Allergens," *Curr. Opin. Immunol.*, 1: 647-53, 1989.

Chen, et al., "Allergenic and Antigenic Determinants of Latex Allergen Hev B 1: Peptide Mapping of Epitopes Recognized by Human, Murine and Rabbit Antibodies", *Clin Exp Allergy*, 26(4): 406-15, Apr. 1996.

Chen, et al., "Isolation and Identification of Hevein as a Major IgE-Binding Polypeptide in Hevea Latex," *J. Allergy Clin. Immunol.* 99(3): 402-409, 1997.

Cheng, et al., "House Dust Mite-Induced Sensitivity in Mice", *Journal of Allergy and Clinical Immunology*, 101(1): 51-59, 1998.

Cheng, et al., "House-Dust Mite (HDM) Induced Hypersensitivity in Mice", *Faseb Journal*, 5(4): 801, 1995.

Cheng, et al., "House-Dust Mite (HDM) Induced Hypersensitivity in Mice", *Journal of Allergy and Clinical Immunology*, 95(1): 380,1995.

Christie, et al., "N-Terminal Amino Acid Sequence Identity Between a Major Allergen of *Asacris lumbricoides* and *Ascaris suum*, and MHC-Restricted IgE Responses to it", *Immunology*, 69:596-602, 1990.

Chua, et al., "Sequence Analysis of cDNA Coding for A Major House Dust Mite Allergen" *J. Exp. Med.* 167:175-182, 1988.

Chua, et al., "Isolation of cDNA Coding for the Major Mite Allergen Der p II by IgE Plaque Immunoassay", *Int. Arch. Allergy Appl. Immunol.* 91:118-123, 1990.

Clarke, et al., "Structure of Mouse Major Urinary Protein Genes: Different Splicing Configurations in the 3'—Non-Coding Region", *EMBO J.*, 3:1045-1052, 1984.

Cockrell, et al., "Monoclonal Antibody Enzyme-Linked Immunosorbent Assay (ELISA) for Ara H 1. A Major Peanut Allergen," *J Aller. Clin. Immunol.*, 89:Abstract 613, 1992.

Colman, "Production of Proteins in the Milk of Transgenic Livestock: Problems, Solutions, and successes," *Am J. Clin. Nutr.* 63(4): 639S-6455S, 1996.

Colman, A. "Production of Therapeutic Proteins in the Milk of Transgenic Livestock" *Biochem. Soc. Symp.* 63: 141-147, 1998.

Cooke & Sampson, "Allergenic Properties of Ovomucoid in Man," *J. Immunol.* 159(4): 2026-32, 1997.

Corbi, et al., "Identification of IgE Binding Polypeptides Cross-Reactive with the *Parietaria judaica* Main Allergenic Polypeptide", *Mol Immunol.* 23(12): 1357-63, Dec. 1986.

Counsell, et al., "Definition of the Human T-Cell Epitopes of Fel D 1, the Major Allergen of the Domestic Cat", *J Allergy Clin Immunol.* 98(5 Pt 1): 884-94, Nov. 1996.

Crameri, et al., "Epidemiology and Molecular Basis of the Involvement of *Aspergillus fumigatus* in Allergic Diseases", *Contrib Microbiol.* Basel. Karger, 2: 44-56.

Czisch, et al., "Conformations of Peptide Fragments Comprising the Complete Sequence of Component III of Chi t I and Their Relationship to T-Cell Stimulation", *Biochemistry* 33(32): 9420-7, Aug. 1994.

Czuppon, et al., "Allergens, IgE, Mediators, Inflammatory Mechanisms", The Rubber Elongation Factor of Rubber Trees (*Hevea brasiliensis*) is the Major Allergen in Latex, *J. Allergy Clin Immunol.*, 92:690-697, 1993.

Daul, et al., "Identification of the Major Brown Shrimp (*Penaeus aztecus*) Allergen as the Muscle Protein Tropomyosin", *Int Arch Allergy Immunol.* 105: 49-55, 1994.

Day, "Genetic Modification of Proteins in Food," *Critical Reviews in Food Science and Nutrition*, 36(S): S49-S67, 1996.

(56) References Cited

OTHER PUBLICATIONS

De Palma, et al., "Use of Antagonist Peptides to Inhibit in Vitro T Cell Responses to Par j1, The M Allergen of *Parietaria judaica* Pollen", *J. Immunol.* 162(4): 1982-7, Feb. 15, 1999.
De Jong, et al., "Food Allergen (Peanut)-Specific TH2 Clones Generated from the Peripheral Blood of a Patient with Peanut Allergy," *J Allergy Clin Immunol.* 98(1): 73-81, 1996.
Demerec, et al., "A Proposal for a Uniform Nomenclature in Bacterial Genetics", *Genetics*, 54: 61-75, 1966.
de Groot, "Affinity Purification of a Major and a Minor Allergen from Dog Extract: Serologic Activity of Affinity-Purified Can f I and of Can f I-Depleted Extract" *J Allergy Clin. Immunol.*, 87:1056-1065, 1991.
Demoly, et al., "Anti-IgE Therapy for Asthma," *American J. Resp. Crit Care Med.* 155: 1825-1827, 1997.
Derossi, et al., "Cell Internalization of the Third Helix of the Antennapedia Homeodomain is Receptor-Independent", *The Journal of Biological Chemistry*, 271(30): 18188-18193, 1996.
Deuell, et al., "*Trichophyton tonsurans* Allergen I, Characterization of a Protein That Causes Immediate But Not Delayed Hypersensitivity" *J. Immunol.*, 147:96-101, 1991.
Dilworth, et al.,"Sequence Analysis of cDNA Coding for a Major House Dust Mite Allergen, Der f I" *Clin. Exp. Allergy*, 21:25-32, 1991.
Directions for Use, Pharmacia Diagnostics AB, Uppsala, Sweden 1985 (Revised 1988).
Dolecek, et al., "Molecular Characterization of Phl p II, a Major Timothy Grass (*Phleum pratense*) Pollen Allergen", *FEBS Letter.*, 335:299-304, 1993.
Ebner, et al., "Multiple T Cell Specificities for Bet v I, the Major Birch Pollen Allergen, with Single Individuals. Studies using Specific T Cell Clones and Overlapping Pepti", *Eur J Immunol.* 23(7): 1523-7, Jul. 1993.
Eichler & Houghten, "Generation and Utilization of Synthetic Combinatorial Libraries," *Mol. Med. Today*, 1(4): 174-80, 1995.
Eigenmann, et al., "Identification of Unique Peanut and Soy Allergens in Sera Adsorbed with Cross-Reacting Antibodies", *J. Allergy Clin Immunol*, 98(5 pt 1):969-78, Nov. 1996.
Ekramoddoullah, "Allergenic Cross Reactivity of Cytochrome c From Kentucky Bluegrass and Perennial Ryegrass Pollens".,*Moll Immunol*. 19: 1527-1534, 1982.
Elfman, et al., "IgE Binding Capacity of Synthetic and Recombinant Peptides of the Major Stor Mite (*Lepidoglyphus destructor*) Allergen, Lep d 2", *Int Arch Allergy Immunol*. 117(3): 167-73, Nov. 1998.
Elsayed, et al., "A Synthetic Hexadecapeptide Derived from Allergen M Imposing Allergenic Antigenic Reactivity", 12(2): 171-5, 1980.
Elsayed, et al., "Allergenic Synthetic Peptide Corresponding to the Second Calcium-Binding of Cod Allergen M", *Scand J Immunol.* 14(2): 207-11, Aug. 1981.
Elsayed, et al., "Antigenic and Allergenic Determinants of Ovalbumin. I. Peptide Mapping, Cleavage at the Methionyl Peptide Bonds and Enzymic Hydrolysis of Native A Carboxymethyl OA", *Int Arch Allergy Appl Immunol*. 79(1): 101-7, 1986.
Elsayed, et al., "Synthetic Allergenic Epitopes from the Amino-Terminal Regions of the Major Allergens of Hazel and Birch Pollen", *Int Arch Allergy Appl Immunol*. 89: 410-415, 1989.
Elsayed, et al., "Tryptic Cleavage of a Homogenous Cod Fish Allergen and Isolation of Two Ac Polypeptide Fragments" *Immunochemistry*, 9(6): 647-61, Jun. 1972.
Elsayed, et al., "The Primary Structure of Fragment TM2 of Allergen M from Cod", *Scand J. Immunol.*, 3: 683-686, 1974.
Elsayed, et al., "Cod Fish Allergen Structure", *Immunochemistry*, 9:647-661, 1972.
Enomoto, et al., "Antibodies Raised Against Peptide Fragments of Bovine Alpha s1-Casein Cross—with the Intact Protein Only When the Peptides Contain Both B and T Cell Determinants", *Mol Immunol*. 27(6): 581-6, Jun. 1990.
Epton, et al., "High-Molecular-Weight Allergens of the House Dust Mite: An Apolipophorin-Li cDNA has Sequence Identity with the Major M-177 Allergen and the IgE-Bin Peptide Fragments Mag1 and Mag3", *Int Arch Allergy Immunol*. 120(3): 185-91, Nov. 1999.
Esch, et al., "Isolation and Characterization of a Major Cross-Reactive Grass Group I Allergenic Determinant", *Mol. Immunol*. 26:557-561.
Espanion, "Methods of Production and Perspectives for Use of Transgenic Domestic Animals," *DTW Dtsch Tierarztl Wochenschr*. 103(8-9): 320-8, 1996.
Ezhevsky, et al., "Hypo-Phosphorylation of the Retinoblastoma Protein (pRb) by Cyclin: D:Cdk4/6 Complexes Results in Active pRb", *Proc. Natl. Acad. Sci. USA*, 94:10699-10704, 1997.
Fahhoum, et al., "Immunologic Variables in a Murine Model of House Dust Mite Sensitivity", *Journal of Allergy and Clinical Immunology*, 99(1): 676, 1997.
Fahhoum, et al., "Tolerization of House Dust Mite Sensitive Mice Using a Major HDM Peptide", *Journal of Allergy and Clinical Immunology*, 101(1): 252, 1998.
Fahy, et al., "The Effect of an Anti-IgE Monoclonal Antibody on the Early-and Late-Phase Responses to Allergen Inhalation in Asthmatic Subjects," *American J Respir Crit Care Med*, 155: 1828-1834, 1997.
Fang, et al., "cDNA Cloning and Primary Structure of a White-Face Hornet Venom Allergen, Antigen 5", *Natl. Acad. Sci., USA*, 85:895-899, 1988.
Fasler, et al., "Antagonistic Peptides Specifically Inhibit Proliferation, Cytokine Production, CD40L Expression, and Help for IgE Synthesis by Der p 1-Specific Human T-Cell Clones", *J Allergy Clin Immunol*. 101(4 Pt 1): 521-30, Apr. 1998.
Faster, et al., "Peptide-Induced Anergy in Allergen-Specific Human Th2 Cells Results in Lack Cytokine Production and B Cell Help for IgE Synthesis. Reversal IL-2, not IL-4 or IL-13", *J Immunol*. 155(9): 4199-206, Nov. 1, 1995.
Ferreira, et al., "Modulation of IgE reactivity of allergens by Site-Directed Mutagenesis: Potential Use of Hypoallergenic Variants for Immunotherapy", *FASEB J*, 12: 231-242 (1998).
Fields, et al., "Solid Phase Peptide Synthesis Utilizing 9-Fluorenylmethoxycarbonyl Amino Acids," *Int J Pept Protein Res*. 35(3): 161-214, 1990.
Fischer, et al., "Characterization of Phl p 4, a Major Timothy Grass (*Phleum pratense*) Pollen Allergen" *J. Allergy Clin Immunol*. 98: 189-198, 1996.
Fitzsimmons, et al., "Immunotherapy—Definition and Mechanism," *Allergy Proc.*, 11: 156 (1990).
Fuchs, et al., "Ingredients for Fat Replacement," *Food Tech.* 51: 82-87, 1997.
Fung-Leung, et al., Transgenic Mice Expressing the Human High-Affinity Immonoglobulin (Ig) E Receptor Alpha Chain Respond to Human lgE in Mast Cell Degranualtion and in Allergic Reactions, *J. Exp. Med. 183*: 49-56 (1996).
Garcia, et al., "Nonspecific Changes in Immunotherapy with House dut extract", *J. Invest Alergol. Clin Immunol*. 5 18-24 (1995).
Geluk, et al., "HLA-DR3 Molecules can Bind Peptides Carrying Two Alternative Specific Submotifs", *J Immunol*. 152(12): 5742-8, Jun. 15, 1994.
Ghosh, et al., "Cloning and Expression of Immunologically Active Recombinant Amb a V Allergen of Short Ragweed Pollen", *J. Immunol.*, 150: 5391-5399, 1993.
Gjesing, et al., "Immunochemistry of Food Antigens", *Ann. Allergy*, 53:602-608, 1984.
Gibbs, et al., "Evolution of Legume See Storage Proteins—a Domain Common to Legumins and Vicilins is Duplicated in Vicilins," *Mol. Biol. Evol*., 6: 614-623 (1989).
Gieni, et al., Allergen-Specific Modulation of Cytokins Synthesis Patterns and lgE Responses in Vivo with Chemically Modified Allergen, *The Journal of Immunol.*, 150: 302-310 (1993).
Gius, et al., "Transduced p16$^{INK4a}$ Peptides Inhibit Hypophosphorylation of the Retinoblastoma Protein and Cell Cycle Progression Prior to Activation of Cdk2 Complexes in Late $G_1^1$" *Cancer Research*, 59:2577-2580, 1999.
Gmachl, et al., "Bee Venom Hyaluronidase is Homologous to a Membrane Protein of Mammalian Sperm", *Proc. Natl. Acad. Sci. USA.*, 90:3569-3573, 1993.
Gonzalez, et al., "Soybean Hydrophobic Protein and Soybean Hull Allergy" *Lancet*, 346:48-49, 1995.

(56) References Cited

OTHER PUBLICATIONS

Goodfriend, et al., "New Ragweed Pollen Allergens", *Fed. Proc.* 38: 1415.
Goodfriend, et al., "Ra5G, A Homologue of Ras5 in Giant Ragweed Pollen: Isolation, HLA-DR-Associated Activity and Amino Acid Sequence", *Mol. Immunol.* 22: 899-906, 1985.
Gordon, Future Immunotherapy: What Lies Ahead?, *Otolaryngol Head Neck Surg.*, 113: 603-605 (1995).
Greene, "Characterization of Allergens of the Cat Flea, *Ctenocephalides felis*: Detection and Frequency of IgE Antibodies in Canine Sera," *Parasit Immunology*, 15: 69-74, 1993.
Greene, et al., IgE and IgG Binding of Peptides Expressed from Fragments of cDNA Encoding the Major House Dust Mite Allergen Der p I *J Immunol.* 147(11): 3768-73, Dec. 1, 1997.
Griffith, et al., "cDNA Cloning of Cry j r, The Major Allergen of *Cryptomeria japonica* (Japanese Cedar)" *J. Allergy. Clin. Immunol.* 91:339, 1993.
Griffith, et al., Sequence Poymorphisms of Amb a I and Amb a II, The Major Allergens in *Ambrosia artemisiifolia* (Short Ragweed). *Int. Arch. Allergy Appl. Immunol.* 96: 296-304, 1991.
Griffith, et al., "Expression and Genomic Structure of the Genes Encoding FdI, the Major Allergen from the Domestic Cat", *Gene*, 113: 263-268, 1992.
Griffith, et al., "Cloning and Sequencing of Lol pI, the Major Allergenic Protein of Rye-Grass Pollen", *FEBS Letters*, 279:210-215, 1991.
Gross, et al., "Isolation and Partial Characterization of the Allergen in Mountain Cedar Pollen", *Scand J. Immunol.*, 8:437-441, 1978.
Guerin-Marchand, et al., "Cloning, Sequencing and Immunological Characterization of Dac g 3, A Major Allergen From *Dactylis glomerata* Pollen", *Mol. Immunol.* 33:797-806, 1996.
Habermann, E., "Bee and Wasp Venoms", *Science*, 177:314-322, 1972.
Halliwell, "Aspects of the Immunopathogenisis of Flea Allergy Dermatitis in Dogs," *Veterinary Immunology and Immunopathology*, 17: 483-494, 1987.
Halliwell, IgE and IgG Antibodies to Flea Antigen in Differing Dog Populations, *Veterinary Immunology and Immunopathology*, 8: 215-223, 1985.
Halmepuro, et al., "Crawfish and Lobster Allergens: Identification and Structural Similarities with Other Crustacea", *Int. Arch Allergy Appl. Immun.* 84: 165-72, 1987.
Haselden, et al., "Immunoglobulin E-independent Major Histocompatibility Complex-restricted T Cell Peptide Epitope-induced Late Asthmatic Reactions" *J Exp Med.* 189(12): 1885-94, Jun. 21, 1999.
Hawrylowicz, et al., "T-Cell Receptor Peptides that Inhibit the T-Cell Response to Allergen Induce Transforming Growth Factor-Beta 1 Production", *J Allergy Clin Immunol.* 97(2): 707-9, Feb. 1996.
Hefle, et al., "Isolation of Peanut Allergens Using Monoclonal Antibodies," *J. Allergy and Clinical Immunology*, 87: Abstract, 209, 1991.
Heiner, et al., "RAST Analyses of Peanut Allergens," *J. Allergy Clin. Immunol.*, 55: 82, 1975.
Helm, et al., "A Major Allergen Involved in IgE Mediated Cockroach Hypersensitivity is a 90 kD Protein with Multiple IgE Binding Domains", *Adv Exp Med Biol.* 409: 267-8, 1996.
Helm, et al., "Cellular and Molecidar Characterization of a Major Soybeam Allergen", *Int. Arch Allergy Immunol.* 117(1), 29-37, Sep. 1998.
Helm, et al., "IgE-Binding of Homologous Legume Vicilins and Glycinins of Soybean and Peanut Allergens", Abstract.
Helm, et al., "Isolation and Characterization of a Clone Encoding a Major Allergen (Bla g Bd90K) Involved in IgE-Mediated Cockroach Hypersensitivity", *J Allergy Clin Immunol.* 98(1): 172-80, Jul. 1996.
Helm, et al., "Isolation and Characterization of Clones Encoding Cockroach Allergens", *Int. Arch Allergy, Immunol.* 107(1-3): 462-3, May-Jun. 1995.
Helm, et al., "Mutational Analysis of the IgE-binding Epitopes of P34/Gly m Bd 30K", *J Allergy Clin. Immunol.* 105(2): 378-84, Jan. 2000.
Helm, et al., "Cloning of a Portion of Ara H 3: A Peanut Allergen", Abstract.
Herian, et al., "Identification of Soybean Allergens by Immunoblotting with Sera from Soy-Allergic Adults," *Int. Arch. Allergy Appl. Immunol.* 92: 193-198, 1990.
Hetzel, et al., "Peptide-Mediated Immunoregulation", *Int Arch Allergy Immunol.* 107:(1-3): 275-7, May-Jun. 1995.
Higgins, et al., "Overlapping T-Cell Epitopes in the Group I Allergen of *Dermatophagoides* sp Restricted by HLA-DP and HLA-DR Class II Molecules", *J Allergy Clin Immunol.* 93(5): 891-9, May 1994.
Higgins, et al., "Peptide-Induced Nonresponsiveness of HLA-DP Restricted Human T Cells rea with *Dermatophagoides* spp", *J Allergy Clin Immunol.* 90(5): 749-56, Nov. 1992.
Hirahara, et al., "Oral Administration of A Dominant T-Cell Determinant Peptide Inhibits Allergen-Specific TH1 and TH2 Cell Responses in Cry J 2-Primed Mice", *J Allergy Clin Immunol.* 102(6 Pt 1): 961-7, Dec. 1998.
Ho, et al., "Comparison of the Immunogenicity of Wasp Venom Peptides With or Without Carbohydrate Moieties", *Toxicon.* 36(1): 217-21, Jan. 1998.
Hoffman, et al., "Allergens in Hymenoptera Venom XXV: The Amino Acid Sequences of Antigen 5 Molecules and the Structural Basis of Antigenic Cross-Reactivity",*J. Allergy Clin. Immunol.*, 92:707-716, 1993.
Hoffman, et al., "Allergens in Hymenoptera Venom XXIV: The Amino Acid Sequences of Imported Fire Ant Venom Allergens Sol i II, Sol i III, and Sol i IV" *J. Allergy Clin. Immunol.*, 91:71-78, 1993.
Hoffman, D.R., "Immunochemical Identification of the Allergens in Egg White", *J. Allergy Clin. Immunol.* 71:481-486, 1983.
Hong, et al., "Pepsin-Digested Peanut Contains T-Cell Epitopes But no IgE Epitopes", J. Allergy Clin. Immunol. 104: 473-7, 1999.
Horner, et al., "Identification of the Allergen Psi c 2 from the Basidiomycete Psilocybe Cubensis as a Fungal Cyclophilin", *Int. Arch. Allergy Immunol.*, 107:298-300, 1995.
Hoyne, et al., "Inhibition of T-Cell Responses by Feeding Peptides Containing Major and Cryp Epitopes: Studies with the Der p I Allergen", *Immunology* 83(2): 190-5, Oct. 1994.
Hoyne, et al., "Peptide Modulation of Allergen-Specific Immune Responses", *Curr Opin Immunol.* 7(6): 757-61, Dec. 1995.
Hsu, et al., "Inhibitition of Specific IgE Response in Vivo by Allergen-Gene Transfer," *Int. Immunol.* 8:1405-1411, 1996.
Jacobson, et al., "Characterization of Bumblebee Venom Allergens" *J. Allergy Clin. Immunol.* 91:187, 1993.
Jacobson, et al., "The Cross-Reactivity Between Bee and Vespid Hyaluronidases has a Structural Basis" *J. Allergy Clin. Immunol.*, 89:292, 1992.
James, et al., "Wheat α-Amylase Inhibitor: A Second Route of Allergic Sensitization", *J Allergy Clin Immunol.* 99(2): Feb. 1997.
James, et al., "Serum IgE Antibodies From Wheat-Allergenic Patients Bind A 50 kD Wheat Protein", Abstract.
Jameson, et al., "The Antigenic Index: A Novel Algorithm for Predicting Antigenic Determinants," *Comput. Appl. Bioscil*, 4: 181-186 (1988).
Jansen, et al., "Prevalance of Food Allergy and Intolerance in the Adult Dutch Population," *J. Allergy Clin. Immunol.*, 93: 446-456 (1994).
Janssen, et al., "Modulation of Th2 Responses by Peptide Analogues in a Murine Model of Alle Asthma: Amelioration or Deterioration of the Disease Process Depends on the Thl or Th2 Skewing Characteristics of the Therapeutic Peptide", *J Immunol.*
Jarman, et al., "Inhibition of Human T-Cell Responses to House Dust Mite Allergens by a T-Cell Receptor Peptide", *J Allergy Clin Immunol.* 94(5): 844-52, Nov. 1994.
Jeannin, et al., "Immunogenicity and Antigenicity of Synthetic Peptides Derived from the Mite Allergen Der p I", *Mol Immunol.* 30(16): 1511-8, Nov. 1993.
Jeannin, et al., "Specific Histamine Release Capacity of Peptides Selected from the Modelized Der p I Protein, a Major Allergen of *Dermatophagoides pteronyssinus*", *Mol Immunol.* 29(6): 739-49, Jun. 1992.
Jensen-Jarolim, et al., "Allergen Mimotopes in Food Enhance Type I Allergic Reactions in Mice", *The FASEB Journal*, 13: 1586-92, Sep. 1999.

(56) References Cited

OTHER PUBLICATIONS

Jensen-Jarolim, et al., "Nonapeptides Selected by Phage Display Mimic the Binding Sites of Monoclonal Antibodies BIP1 and BIP4 on Bet v 1, The Major Birch Pollen Allergen", *Int Arch Allergy Immunol.* 118(2-4): 224-5, Feb.-Apr. 1999.
Jensen-Jarolim, et al., "Peptide Mimitopes Displayed by Phage Inhibit Antibody Binding to Bet v 1, the Major Birch Pollen Allergen, and Induce Specific IgG Response in Mice", FASEB J. 12(15): 1635-42, Dec. 1998.
Jimenez, et al., Sensitization to Sunflower Pollen: Only an Occupational Allergy? *Int. Arch Allergy Immunol.* 105:297-307, 1994.
Jusko, "Corticosteroid Pharmacodynamics: Models for Broad Array of Receptor-mediate Pharmacologic Effects," *Clin. Pharmacol*, 30: 303-10, 1990.
Kaminogawa, "Food Allergy, Oral Tolerance and Immunomodulation—Their Molecular and Cellular Mechanisms," *Biosci. Biotech, Biochem*. 60: 1749-1756, 1996.
Kammerer, et al/. "Modulation of T-Cell Response to Phospholipase A2 and Phospholipase A2-Derived Peptides by Conventional Bee Venom Immunotherapy", *J Allergy Clin Immunol.* 100(1): 96-103, Jul. 1997.
Kapitany, et al., "A High Resolution PAS Stain for Polyacrylamide Gel Electrophoresis," *Anal. Biochem*., 56: 361-9, 1973.
Keating, et al. "Immunoassay of Peanut Allergens in Food-Processing Materials and Finished Foods," *J. Allergy Clin. Immunol.* 86: 41-44, 1990.
Kettner, et al., "IgE and T-Cell Responses to High-Molecular Weight Allergens from Bee Venom", *Clin. Exp. Allergy*, 29(3): 394-401, Mar. 1999.
KielisZewski, et al. "Potato Lectin: A Modular Protein Sharing Sequence Similarities with the Extensin Family, the Hevein Lectin Family, and Snake Venom Disintegrins (Platelet Aggregation Inhbitiors)," *Plant J.* 5(6): 849-861, 1994.
Kim, et al., "Suppressive Vaccination at Allergen-Induced Immunoglobulin E Production by the Naked DNA Vaccine", *Journal of Investigative Medicine*, 46(3): A243, 1998.
Kim, et al., "Suppressive Vaccination of Allergen-Induced Immunoglobulin E Production by the Naked DNA Vaccine" *Faseb Journal*, 12(5): 6148, 1998.
King, et al., "Isolation and Characterization of Allergen from Ragweed Pollen" *Biochemistry*, 3: 458-468, 1964.
King, et al., "Modulation of the Allergenicity of a Major Peanut Allergen, Ara h 2 by Mutagenesis of Its Immunodominant IgE Binding Epitopes", Abstract.
King, et al., "The Isolation and Characterization of a Novel Collagenolytic Serine Protease Allergen (Der p 9) from the Dust Mite *Dermatophagoides pteronyssinus*", *J. Allergy Clin Immunol.*, 98:739-747, 1996.
King, et al., "Structural Studies of a Hornet Venom Allergen Antigen 5, Dol m V and its Sequence Similarity with Other Proteins" *Prot. Seq. Data Anal*., 3:263-266, 1990.
King, et al., "Yellow Jacket Venom Allergens, Hyaluronidase and Phospholipase: Sequence Similarity and Antigenic Cross-Reactivity with Their Hornet and Wasp Homologs and Possible Implications for Clinical Allergy" *Allergy Clin. Immunol.*, 98:588-600, 1996.
Klapper, et al., "Amino Acid Sequence of Ragweed Allergen Ra3", *Biochemistry*, 19: 5729-5734, 1980.
Klysner, et al., "Group V Allergens in Grass Pollens: IV. Similarities in Amino Acid Compositions and $NH_2$-Terminal Sequences of the Group V Allergens from Lolium Perenne, Poa *Pratensis* and *Dactylis glomerata*", *Clin. Exp. Allergy*, 22:491-497, 1992.
Kohler, et al., "Continuous Cultures of Fused Cells Secreting Antibody of Predefined Specificity," *Nature*, 256: 495-497, 1975.
Kopper, et al., "Rapid Isolation of Peanut Allergens and Their Physical Chemical and Biological Characterization", Abstract.
Kricek, et al., "IgE-Related Peptide Mimotopes, Basic Structures for Anti-Allergy Vaccine Development", *Int Arch Allergy Immunol*. 118 (2-4): 222-3, Feb.-Apr. 1999.
Krieg, et al., "CpG Motifs in Bacterial DNA Trigger Direct B-Cell Activation," *Nature*, 374(6522): 546-9, 1995.

Kuchler, et al., "Analysis of the cDNA for Phospholipase $A_2$ from Honeybee Venom Glands; The Deduced Amino Acid Sequence Reveals Homology to the Corresponding Vertebrate Enzymes", *Eur. J. Biochem*., 184:249-254, 1989.
Kumar, et al., "Isolation and Characterization of a Recombinant Heat Shock Protein of *Aspergillus fumigatus*", *J. Allergy Clin. Immunol.*, 91:1024-1030, 1993.
Kurup, et al., "Immunodominant Peptide Epitopes of Allergen, Asp F 1 from the Fungus *Aspergillus fumigatus*", *Peptides*, 19(9): 1469-77, 1998.
Kwon, et al., "Immunoprotective Effect of Vaccination with DNA Encoding T Cell Epitopes on the Der p Induced IgE Production" *Journal of Allergy and Clinical Immunology*, 103: 418, 1999.
Kwon, et al., "The Effect of the Intradermal Vaccination with DNA Encoding the T-Cell Receptor on the Induction of Experimental Autoimmune Encephalomyelitis in Mice", *Journal of Allergy and Clinical Immunology*, 103: 76, 1999.
Lacroix, et al., "Attenuation of Allergen-Evoked Nasal Responses by Local Pretreatment with Exogenous Neuropeptide Y in Atopic Patients", *J Allergy Clin Immunol*. 98(3):611-6, Sep. 1996.
Laemmli, "Cleavage of Structural Proteins During the Assembly of the Head of Bacteriophage T4", *Nature*, 227: 680-5, 1970.
Lake, et al., "House Dust Mite-Derived Amylase: Allergenicity and Physicochemical Characterization", *J. Allergy Clin. Immunol*. 87:1035-1042, 1991.
Langeland, T., "A Clinical and Immunological Study of Allergy to Hen's Egg White", *Allergy*, 38:493-500, 1983.
Laperche, et al., "Tissue-Specific Control of $\alpha_{2u}$ Globulin Gene Expression: Constitutive Synthesis in the Submaxillary Gland" *Cell*, 32:453-460, 1983.
Larsen, et al., "PCR Based Cloning and Sequencing of Isogenes Encoding the Tree Pollen Major Allergen *Car b* I from *Carpinus betulus*, Hornbeam", *Mol. Immunol*. 29: 703-711, 1992.
Lehrer, et al., "Reactivity of IgE Antibodies with Crustacea and Oyster Allergens: Evidence for Common Antigenic Structures", *J Allergy Clin. Immunol*. 80(2): 133-39, Aug. 1987.
Lemanske & Taylor, "Standardized Extracts, Foods," *Clin. Rev. Allergy*, 5: 23-26, 1987.
Leung, et al., "Identification and Molecular Characterization of *Charybdis feriatus* Tropomyosin, The Major Crab Allergen", *J Allergy Clin Immunol*. 847-852, Nov. 1998.
Leung, et al., "IgE Reactivity Against a Cross-Reactive Allergen in Crustacea and Mollusca: Evidence for Tropomyosin as the Common Allergen", *J. Allergy Clin Immunol*. 98(5), 954-961, Nov. 1996.
Liebers, et al., "Epitope Mapping with Peptides of Chi t I Component III and Immunomodula of the Chi t Immune Response", *J Allergy Clin Immunol*. 92(2): 334-9, Aug. 1993.
Lind, et al., "The Binding of Mouse Hybridoma and Human IgE Antibodies to the Major Fecal Allergen, Der p I, of *Dermatophagoides pteronyssinus*, Relative Binding Site Location and Species Specificity Studied by Solid-Phase Inhibition Assays with Radiolabeled Antigen", *J. Immunol*., 140:4256-4262, 1988.
Ling, et al., "Construction and Characterization of Human IgE Fab Fragments Specific to Peanut Allergens", Abstract.
Litwin, et al., "Regulation of the Human Immune Response to Ragweed Pollen by Immunotherapy. A Controlled Trial Comparing the Effect of Immunosuppressive Peptic Fragments of Short Ragweed with Standard Treatment", *Clin Exp. Allergy*. 21(4): 457-65, Jul. 1991.
Litwin, et al., "Regulation of the Immune Response to Allergens by Immunosuppressive Allergenic Fragments, Peptic Framents of Honey Bee Venom Phospholipase", *Int Arch Allergy Appl Immunol*. 87(4): 361-6, 1988.
Lopata, et al., "Characteristics of Hypersensitivity Reactions and Identification of a Unique 49 kd IgE-Binding Protein (Hal-m-1) in Abalone (*Haliotis midae*)" *J. Allergy Clin. Immunol*. , 1997.
Lowenstein, H., "Timothy Pollen Allergens" *Allergy*: 35: 188-191, 1980.
Lu, et al., "Sequence Analysis and Antigenic Cross-Reactivity of a Venom Allergen, Antigen 5, From Hornets, Wasps, and Yellow Jackets" *The Journal of Immunology*, 150:2823-2830, 1993.
Maguire, et al., "The Safety and Efficacy of ALLERVAX CAT in Cat Allergic Patients" *Clin Immunol*. 93(3): 222-31, Dec. 1999.

(56) References Cited

OTHER PUBLICATIONS

Maleki, et al., "T-Cell Responses in Food Allergy: Identification of T-Cell Epitopes on a Major Peanut Allergen", Abstract.

Marcotte, et al., "Effects of Peptide Therapy on Ex Vivo T-Cell Responses", *J Allergy Clin Immunol*. 101(4 Pt 1): 506-13, Apr. 1998.

Marsh, et al., "Allergen Nomenclature", *Bull WHO* 64: 767-770, 1986.

Mathison, et al., "A Peptide from the Submandibular Glands Modulates Inflammatory Responses", *Int Arch Allergy Immunol*. 113 (1-3): 337-8, May-Jul. 1997.

Matthiesen, et al., "Group V Allergens in Grass Pollens. I. Purification and Characterization of the Group V Allergen from Phleum Pratense Pollen, Phl p V", *Clin. Exp. Allergy*, 21:297-307.

Matsuoka, et al., "Altered TCR Ligands Affect Antigen-Presenting Cell Responses: Up-Regulation IL-12 by an Analogue Peptide", *J Immunol*. 157(11): 4837-43, Dec. 1996.

McKeon, "IgG and IgE Antibodies Against Antigens of the Cat Flea, *Ctenocephalides felis* Felis in Sera of Allergic and Non-Allergic Dogs," *Int. J. Parasitology*, 24(2): 259-263, 1994.

Mecheri, et al., "Purification and Characterization of a Major Allergen from *Dactylis glomerata* Pollen: The Ag Dgl", *Int. Arch. Allergy Appl. Immunol*., 78:283-289.

Mena, et al., "A Major Barley Allergen Associated with Baker's Asthma Disease is a Glycosylated Monomeric Inhibitor o f Insect α-Amylase: cDNA Cloning and Chromosomal Location of the Gene", *Plant Molec. Biol.* 20:451-458, 1992.

Mendez-Arias, et al., "Primary Structure of the Major Allergen of Yellow Mustard (*Sinapis alba* L.) Seed, Sin α I" *Eur. J. Biochem*., 177:159-166, 1988.

Metcalfe, "Food Allergens," *Clin Rev Allergy*, 3:331-49, 1985.

Metzler, et al., "Determination of the Three-Dimensional Solution Structure of Ragweed Allergen Amb t V by Nuclear Magnetic Resonance Spectroscopy". *Biochemistry*, 31: 5117-5127, 1992.

Metzler, et al., "Proton Resonance Assignments and Three-Dimensional Solution Structure of the Ragweed Allergen Amb a V by Nuclear Magnetic Resonance Spectroscopy" *Biochemistry*, 31: 8697-8705, 1992.

Miller, et al., "Allergy to Bovine Beta-Lactoglobulin: Specificity of Immunoglobulin E Gener in the Brown Norway Rat to Tryptic and Synthetic Peptides", *Clin. Exp. Allergy*, 29(12): 1696-704, Dec. 1999.

Miyazawa, et al., "Identification of the First Major Allergen of a Squid (*Todarodes pacificus*)", *J. Allergy Clin. Immunol*., 98:948-953, 1996.

Mohapatra, SS, "Modulation of Allergen-Specific Antibody Responses by T-Cell-Based Peptide Vaccine(s). Principles and Potential", *Clin Rev Allergy*. 12(1): 3-22, Spring, 1994.

Moneret-Vautrin, "Modifications of Allergenicity Linked to Food Technologies," *Allerg Immunol*, 30(1): 9-13, 1998.

Monsalve, et al., "Characterization of a New Oriental-Mustard (*Brassica juncea*) Allergen, Bra j IE: Detection of an Allergenic Epitope" *Biochem. J.*, 293:625-632, 1993.

Morgenstern, et al., "Amino Acid Sequence of Fel d I, the Major Allergen of the Domestic Cat: Protein Sequence Analysis and cDNA Cloning" *Proc. Natl. Acad. Sci. USA*, 88: 9690-9694, 1991.

Muckerheide, et al., "Immunosuppressive Properties of a Peptic Fragment of BSA", The Journal of Immunology, 119(4): 1340-45, Oct. 1977.

Muckerheide, et al., "Kinetics of Immunosuppression Induced by Peptic Fragments of Bovine Serum Albumin", *Cellular Immunology*, 50, 340-47, 1980.

Muller, et al., "Successful Immunotherapy with T-Cell Epitope Peptides of Bee Venom Phospholipase A2 Induces Specific T-Cell Anergy in Patients Allergic to Bee Venom" *J Allergy Clin Immunol.* 101(6 Pt 1): 747-54, Jun. 1998.

Nagahara, et al., "Transduction of Full-Length TAT Fusion Proteins into Mammalian Cells: TAT-p27$^{Kip1}$ Induces Cell Migration", *Nature Medicine*, 4(12): 1449-1452, 1998.

Nair, Smita et al., Soluble Proteins Delivered to Dendritic Cells Via pH-sensitive Liposomes Induce Primary Cytotoxic T Lymphocyte Responses In Vitro, *J. Exp. Med.*, 175 Feb. 1992 609-612.

Nelson, et al., "Treatment of Anaphylactic Sensivitity to Peanuts by Immunotherapy with Injections of Aqueous Peanut Extract," *J. Allergy Clin. Immunol.* 99: 744-751, 1997.

Nilsen, et al.,"Structural Analysis of the Glycoprotein Allergen Art v from the Pollen of Mugwort (*Artemisia vulgaris* L.)" *J. Biol. Chem.* 266: 2660-2668.

Nicodemus, et al., "Integrated Clinical Experience with Tolerogenic Peptides", *Int Arch Allergy Immunol.* 113:(1-3): 326-8, May-Jul. 1997.

Nishiyama, et al., "Determination of Three Disulfide Bonds in a Major House Dust Mite Allergen, Der f II", *Int. Arch. Allergy Immunol.*, 101:159-166, 1993.

Noon, "Prophylactic Inoculatio Against Hay Fever," *Lancet*, 1: 1572-73, 1911.

Nordlee, et al., "Allergenicity of Various Peanut Products as Determined by RAST Inhibition," *J Allergy Clin. Immunol.* 68: 376-82, 1981.

Norman, et al., "Clinical and Immunologic Effects of Component Peptides in Allervax Cat", *Int Arch Allergy Immunol*. 113(1-3): 224-6, May-Jul. 1997.

Norman, et al., "Multicenter Study of Several Doses of ALLER-VAX® Cat Peptides in the Treatment of Cat Allergy," *Journal of Allergy and Clinical Immunology*, 99: S127, 1997.

Norman, et al., "Treatment of Cat Allergy with T-Cell Reactive Peptides" *Am J Respir Crit Care Med.* 154(6 Pt 1): 1623-8, Dec. 1996.

Obispo, et al., "The Main Allergen of *Olea europaea* (Ole e I) is Also Present in other Species of the *Oleaceae* Family", *Clin. Exp. Allergy*, 23:311-316, 1993.

O'Brien, et al., "An Immunogenetic Analysis of T-Cell Reactive Regions on the Major Allergen from the House Dust Mite, Der p I, with Recombinant Truncated Fragments", *J Allergy Clin Immunol.* 93(3): 628-34, Mar. 1994.

O'Farrell, "High Resolution Two-Dimensional Electrophoresis of Proteins," *J. Biol. Chem.* 250: 4007-21, 1975.

O'Hehir, et al., "House Dust Mite Allergy: From T-Cell Epitopes to Immunotherapy", *Eur J Clin Invest*. 23(12): 763-72, Dec. 1993.

O'Hehir, et al., An In Vitro Model of Peptide-Mediated Immunomodulation of the Human T c Response to *Dermatophagoides* spp (House Dust Mite) *J Allergy Clin Immunol.* 87(6): 1120-7, Jun. 1991.

Okano, et al., "Population Analysis of Cellular Respones to Synthetic Peptides of Der p II, a Major Allergen Molecule of *Dermatophagoides pteronyssinus*, in Allergic and Nonallergic Subjects", *Allergy*. 49(6): 436-41, Jul. 1994.

Olsen, et al., "Identification and Characterization of the Poa p IX Group of Basic Allergens of Kentucky Bluegrass Pollen", *J. Immunol*.147: 205-211.

O'Neil, et al., "Cloning and Characterization of a Major Allergen of the House Dust Mite, *Dermatophagoides pteronyssinus*, Homologous with Glutathione S-Transferase", *Biochimica et Biophysica Acta*, 1219:521-528, 1994.

Oppenheimer, et al., "Treatment of Peanut Allergy with Rush Immunotherapy", *J Allergy Clin Immunol*. 90: 256-62, 1992.

Park, et al., "Pediatric IgE Anibody binding to the Most Common Seafood Proteins in Korea", *Journal of Allergy and Clinical Immunology*, 101(1): 377, 1998.

Pecquet, et al., "Immunoglobulin E Suppression and Cytokine Modulation in Mice Orally Tolerized to β-Lactoglobulin", *Immunology*, 96, 278-85, 1999.

Pene, et al., "Immunotherapy with Fel D 1 Peptides Decreases IL-4 Release by Peripheral Blood T Cells of Patients Allergic to Cats", 102: (4 Pt 1): 571-8, Oct. 1998.

Perez, et al., "cDNA Cloning and Immunological Characterization of the Rye Grass Allergen Lol p I" *J. Biol. Chem.* 265:16210-16215, 1990.

Pesce, et al., "Modulation of the Immune Response to Allergens: Phospholipase A Degradation Products Suppress IgG and IgE Response in Mice", *Int Arch Allergy Appl Immunol*, 92, 88-93, 1990.

(56) References Cited

OTHER PUBLICATIONS

Petersen, et al., "Characterization of the Allergen Group VI in Timothy Grass Pollen (Ph1 p6) II. c DNA Cloning of Ph1 p 6 and Structural Comparison to Grass Group V", *Arch. Allergy Immunol.* 108: 55-59.

Phadebas Rast Radioimmunoassay Reagents for 100 or 300 Tubes, Pharmacia Diagnostics AB, Uppsala Sweden 1985, Revised Jan. 1988.

Pisetsky, "Immune Activation by Bacterial DNA: A New Genetic Code," *Immunity*, 5(4): 303-10, 1996.

Pollart, et al., "Identification, Quantitation, and Purification of Cockroach Allergens using Monoclonal Antibodies," *J. Allergy Clin. Immunol.*, 87: 511-521, 1991.

Posch, et al., "Characterization and Identification of Latex Allergens by Two-Dimensional Electrophoresis and Protein Microsequencing," *J. Allergy Clin. Immunol*, 99(3): 385-395, 1997.

Pucheu-Haston, "Allergenic Cross-Reactivities in Flea-Reactive Canine Serum Samples," *AJVR* 57(7): 1000-1005, 1996.

Rabjohn, et al., "Glycinin, A Third Major Peanut Allergen Identified by Soy-Adsorbed Serum IgE from Peanut Sensitive Individuals", Abstract.

Rabjohn, et al., "Molecular Cloning and Epitope Analysis of the Peanut Allergen Ara h 3", *J. Clin. Invest.* 103(4), 535-42, Feb. 1999.

Rabjohn, et al., "Mutational Analysis of the IgE-Binding Epitopes of the Peanut Allergen, Ara h 3: A Member of the Glycinin Family of Seed-Storage Proteins", Abstract.

Rafner, et al., "Cloning of Amb a I (Antigen E), the Major Allergens Family of Short Ragweed Pollen", *J. Biol. Chem.* 266: 1229-1236, 1991.

Raz, et al., "Intradermal Gene Immunization: The Possible role of DNA Uptake in the Induction of Cellular Immunity to Viruses," *Proc Nat Acad Sci USA*, 91:9519-9523, 1994.

Reese, et al., "Characterization of Recombinant Shrimp Allergen Pen a 1 (Tropomyosin)", *Int Arch Allergy Immunol*, 113: 240-242, 1997.

Remy, et al., "Topical Peptides: Percutaneous Absorption of a Vasopressin Derivate, Grass Pollen, and Other Allergens by Iontophoresis in Men", *J Invest Dermatol*. 91(6): 606, Dec. 1988.

Roberts, et al., "Nucleotide Sequence of cDNA Encoding the Group II Allergen of Cocksfoot/Orchard Grass (*Dactylis glomerata*), Dac g II", *Allergy*, 48:615-623, 1993.

Roebber, et al., "Immunochemical and Genetic Studies of Amb t V (Ra5G), an Ra5 Homologue from Giant Ragweed Pollen", *J. Immunol*. 134: 3062-3069, 1985.

Roebber, et al., "Isolation and Characterization of Allergen Amb a VII from Short Ragweed Pollen", *J. Allergy Clin. Immunol*. 87: 324, 1991.

Rogers, et al., "Potential Therapeutic Recombinant Proteins Comprised of Peptides Containing Recombined T Cell Epitopes", *Mol Immunol*. 31(13): 955-66, Sep. 1994.

Rogers, et al., "Complete Sequence of the Allergen Amb a II: Recombinant Expression and Reactivity with T Cells from Ragweed Allergic Patients", *J. Immunol*. 147: 2547-2552, 1991.

Rolfsen, "Detection of Specific IgE Antibodies Towards Cat Flea (*Ctenocephalides felis* Felis) in Patients with Suspected Cat Allergy," *Allergy*, 42: 177-181 (1987).

Rolland, et al., "Immunotherapy of Allergy: Anergy, Deletion, and Immune-Deviation", Current Opinion in Immunology, 10: 640-45, 1998.

Rooney, et al., "Antiparallel, Intramolecular Triplex DNA Stimulates Homologous Recombination in Human Cells," *Proc. Natl. Acad. Sci. USA*, 92: 2141-2144, 1995.

Sachs, et al., "Isolation and Partial Characterization of a Major Peanut Allergen," *J. Allergy Clin. Immunol*. 67: 27-34, 1981.

Sakaguchi, et al., "Identification of the Second Major Allergen of Japanese Cedar Pollen", *Allergy*, 45:309-312, 1990.

Sampson & McCaskill, "Food Hypersensitivity in Atopic Dermatitis: Evaluation of 113 Patients," *J. Pediatr*. 107: 669-75, 1995.

Sampson, "Peanut Anaphylaxis," *J Allergy Clin Immunol.*, 86: 1-3, 1990.

Sampson, "Role of Immediate Food Hypersensitivity in the Pathogenesis of Atopic Dematitis," *J. Allergy Clin. Immunol.* 71: 473-80, 1993.

Sampson, et al., "Fatal and Near-Fatal Anaphylactic Reactions to Food in Children and Adolescents", *The New England Journal of Medicine*, 327(6): 380-84, Aug. 1992.

Sampson, et al., "Food Allergy and the Role of Immunotherapy," *J Allergy Clin. Immun*, 90:151-52, 1992.

Sampson, et al., "Mechanisms of Food Allergy," *Annu. Rev. Nutr*, 16: 161-77, 1996.

Reisman, "Fifteen yeas of hymenoptera Venom Immunotherapy," *J. Allergy Clin Immunol.*, 90: 256-62 (1992).

Scheiner, "Recombinant Allergens: Biological, Immunological and Practical Aspects," *Int. Arch. Allergy Immunol.*, 98: 93-96 (1992).

Schemmer, "Efficacy of Alum-Precipitated.Flea Antigen for Hyposensitization of Flea-Allergic Dogs," *Seminars in Veterinary Medicine and Surgery (Small Animal)*, 2(3): 195-198, 1987.

Schmidt, et al., "cDNA Analysis of the Mite Allergen Lep d 1 Identifies Two Different Isoallergens and Variants", *FEBS Letter*, 370:11-14, 1995.

Schmidt, et al., "The Complete cDNA Sequence and Expression of the First Major Allergenic Protein of *Malassezia furfur*, Mal f 1", *Eur J. Biochem.*, 246:181-185, 1997.

Schmidt, et al., "Nucleotide Sequence of cDNA Encoding the Fire Ant Venom Protein Sol i II", *FEBS Letter*, 319:138-140, 1993.

Schwarze, et al. "In Vivo Protein Transduction: Delivery of a Biologically Active Protein into the Mouse", Science, 285: 1569-1572.

Secrist, et al., "Allergen Immunotherapy Decreases Interleukin 4 Production in CD4+T Cells From Allergic Individuals," *J. Exp. Med.* 178 2123-2130 (1993).

Sehra, et al., "Role of Liposomes in Selective Proliferation of Splenic Lymphocytes" *Molecular and Cellular Biochemistry*, 183: 133-139, 1998.

Sen, et al., "Allergen Structure May Dictate Why Some IgE Binding Epitopes Become Immunodominant Within a Food Allergic Population", Abstract.

Sevier, et al., "Monoclonal Antibodies in Clinical Immunology," *Clin. Chem*. 27(11): 1797-1806, 1981.

Shanti, et al., "Identification of Tropomyosin as the Major Shrimp Allergen and Characterization of its IgE-Binding Epitopes: ," *J. Immunol*, 151: 5354-5363, 1993.

Sharif, et al., "Biodegradable microparticles as a delivery system for the allergens of *Dermatophagoides pteronyssinus* (house dust mite): I. Preparation and characterization of microparticles", *International Journal of Pharmaceutics*, 119 1995) 239-246.

Shen, et al., "Molecular Cloning of a House Dust Mite Allergen with Common Antibody Binding Specificities with Multiple Components in Mite Extracts", *Clin. Exp. Allergy*, 23: 934-940, 1993.

Shen, et al., "Studies on Allergens of *Aspergillus flavus* ", *J. Allergy Clin. Immunol.*, 103:S157, 1999.

Shen, et al., "Allergenic Components in Three Different Species of Penicillium: Crossreactivity Among Major Allergens" *Clin. Exp. Allergy*, 26:444-451, 1996.

Shen, et al., "Molecular Cloning of cDNA Coding for the 68 kDa Allergen of *Penicillium notatum* Using MoAbs", *Clin Exp. Allergy*, 25:350-356, 1995.

Shen, et al., "The 40-Kilodalton Allergen of *Candida albicans* is an Alcohol Dehydrogenase: Molecular Cloning and Immunological Analysis Using Monoclonal Antibodies", *Clin Exp. Allergy*, 21:675-681, 1991.

Shin, et al., "Biochemical and Structural Analysis of the IgE Binding Sites on Ara hl, An Abundant and Highly Allergenic Peanut Protein", *J. Biol. Chem.* 273(22): 13753-9, May 1998.

Shin, et al., Characterization of a Major Peanut Allergen: Mutational Analysis of the Ara h 1 IgE Binding Epitopes and Strategies for the Creation of a Hypoallergenic Peanut Clone, Abstract.

Shin, Modulation of the Reactivity of the Major Peanut Allergen Ara h 1 Through Epitope Characterization, Structural Analysis, and Mutation, Abstract.

Shin, et al., "Tertiary Structure of the Major Peanut Allergen Ara h 1: Implications for the Bioengineering of a Hypoallergenic Protein", Abstract.

(56) References Cited

OTHER PUBLICATIONS

Sidoli, et al., "Cloning, Expression, and Immunological Characterization of Recombinant Lolium-Perenne Allergen Lol p II", *J. Biol Chem.*, 268:21819-21825, 1993.

Simons, et al., "Fel D 1 Peptides: Effect on Skin Tests and Cytokine Synthesis in Cat-Allergic Human Subjects", Int Immunol. 8(12): 1937-45, Dec. 1996.

Singh, et al., "Isolation of cDNA Encoding a Newly Identified -Major Allergenic P, rotein of Rye-Grass Pollen: Intracellular Targeting to the Amyloplast", *Proc. Natl. Acad. Sci.*, 88:1384-1388, 1991.

Smith, et al., "Cloning and Expression in Yeast *Pichia pastoris* of a Biologically Active Form of Cyn d 1, the Major Allergen of Bermuda Grass Pollen", *J. Allergy Clin. Immunol.* 98:331-343, 1996.

Smith, et al., "Comparative Analysis of the Genes Encoding Group 3 Allergens from *Dermatophagoides pteronyssinus* and *Dermatophagoides farinae*", Int Arch Allergy Immunol., 109:133-140, 1996.

Soldatova, et al., "Sequence Similarity of a Hornet (*D. maculata*) Venom Allergen Phospholipase $A_1$ with Mammalian Lipases", *FEBS Letters*, 320:145-149, 1993.

Sone, et al., "T Cell Epitopes in a Japanese Cedar (*Cryptomeria japonica*) Pollen Allergens: Choice of Major T Cell Epitopes in Cry j 1 and Cry j 2 Toward Design of the Peptide-Immunotherapeutics for the Management of Japanese Cedar Pollinosis"; *J. Immunol.* 161(1): 448-57, Jul. 1, 1998.

Sparholt, et al., The Allergen Specific B-Cell Response During Immunotherapy. *Clinical and Experimental Allergy*, 22: 648-653 (1992).

Stadler, et al., "Mimotope and Anti-Idiotypic Vaccines to Induce an Anti-IgE Response", *Int Arch Allergy Immunol.* 118(2-4): 119-21, Feb.-Apr. 1999.

Stanley, et al., "Biochemistry of Food Allergens", Clin Rev. Allergy Immunol. 17(3): 279-91, 1999.

Stanley, et al., "Identification and Mutational Analysis of the Immunodominant IgE Binding Epitopes of the Major Peanut Allergen Ara h 2", *Arch Biochem Biophys.* 342(2): 244-53, Jun. 1997.

Stanley, et al., "Peanut Hypersensitivity. IgE Binding Characterictics of a Recombinant Ara h I Protein", *Adv. Exp Med. Biol.* 409: 213-6, 1996.

Stanley, et al., "Mapping of the B-Cell Epitopes on Ara h 1 and Ara h II, Legume Storage Proteins and Major Allergens Involved in Peanut Hypersensitivity", Abstract.

Stanley, et al., "Ara h I, A Major Allergen Involved in Peanut Hypersensitivity, Has Multiple IgE Binding Domains", Abstract.

Stanley, et al., "Isolation and Quantitation of mRNA Differentially Expressed in Stimulated T Lymphocytes from Peanut Hypersensitive Individuals", Abstract.

Stanworth, et al., "Allergy Treatment with a Peptide Vaccine", *Lancet*. 336(8726): 1279-81, Nov. 24, 1990.

Stanworth, et al., "Nomenclature for Synthetic Peptides Respresentative of Immunoglobulin Chain Sequences", *Bulletin WHO*, 68: 109-111, 1990.

Steinberger, et al., "Construction of a Combinatorial IgE Library from an Allergic Patient. Isolation and Characterization of Human IgE Fabs with Specificity for the Major Timothy Grass Pollen Allergen, Ph1 p 5", *J. Biol. Chem.* 271: 10967-10982, 1996.

Sunderasan, et al., "Latex B-Serum β-1,3-Glucanase (Hev b II) and a Component of the Microhelix (Hev b IV) are Major Latex Allergens" *J. Nat Rubb Res.*,10:82-99, 1995.

Suphioglu, et al., "Peptide Mapping Analysis of Group I Allergens of Grass Pollens", *Int Arch Allergy Immunol.* 102(2): 144-51, 1993.

Suphioglu, et al., "Molecular Cloning and Immunological Characterisation of Cyn D 7, A Novel Calcium-Binding Allergen from Bermuda Grass Pollen", *FEBS Letter*. 402:167-172, 1997.

Suphioglu, et al., "Cloning, Sequencing and Expression in *Escherichia coli* of Pha a 1 and Four Isoforms of Pha a 5, The Major Allergens of Canary Grass Pollen", *Clin. Exp. Allergy*, 25:853-865, 1995.

Sutton, et al., "Detection of IgE and IgG Binding Proteins After Electrophoresis Transfer From Polyacrylamide Gels", *Journal of Immunological Methods*, 52:183-86, 1982.

Svirshchevskaya, et al., "Intravenous Injection of Major and Cryptic Peptide Epitopes of Ribotoxin, Asp Fl Inhibits T Cell Response Induced by Crude *Aspergillus fumigatus* Antigens in Mice", 21(1): 1-8, Jan. 1, 2000.

Sward-Nordmo, et al., "The Glycoprotein Allergen Ag-54 (Cla h II) From *Cladosporium herbarum*, Structural Studies of the Carbohydrate Moiety", *Int. Arch. Allergy Appl. Immunol.*, 85:288-294, 1988.

Szostak, "In Vitro Genetics", *TIBS*, 19:89, 1992.

Takai, et al., "Engineering of the Major House Dust Mite Allergen Der f 2 for Allergen-specific Immunotherapy," *Nature Biotechnology*, 15:754-58 (1997).

Takashi, et al., "Engineering of Hypoallergenic Mutants of the Brassica Pollen Allergen, Bra r 1, for Immunotherapy," *FEBS Letters*, 434: 255-260 (1998).

Taniai, et al., N-Terminal Amino Acid Sequence of a Major Allergen of Japanese Cedar Pollen (Cry *j* I) *FEBS Letter*, 239:329-332, 1988.

Taylor, et al., "Peanut Oil is Not Allergenic to Peanut Sensitive Individuals", *J. Allergy Clin. Immunol.*, 68: 372-375 (1981).

Taylor, et al., "Evidence for the Ecistence of Multiple Allergens in Peanuts," *J. Allergy Clin. Immunol.* 69:128, 1982.

Teshima, et al., "Isolation and Characterization of a Major Allergenic Component (gp55) of *Aspergillus fumigatus*", *J. Allergy Clin. Immunol.* 92:698-706, 1993.

Texier, et al., "HLA-DR Restricted Peptide Candidates for Bee Venom Immunotherapy", *J. Immunol,.* 164(6): 3177-84, Mar. 15, 2000.

Thomas, et al., "Purification of Membrane Proteins," Meth. Enzymol., 182:499-520, 1990.

Tovey, et al., "Cloning and Sequencing of a cDNA Expressing a Recombinant House Dust Mite Protein that Binds Human IgE and Corresponds to an Important Low Molecular Weight Allergen", *J. Exp. Med.* 170:1457-1462, 1989.

Towbin, et al., "Electrophoretic Transfer of Proteins from Polyacrylamide Gels to Nitrocellulose Sheets: Procedure and Some Applications," Proc. Natl. Acad. Sci. USA, 176: 4350-54, 1979.

Trudinger, et al., "cDNA Encoding the Major Mite Allergen Der *f*II" *Clin. Exp. Allergy*, 21:33-38, 1991.

Twardosz, "Molecular Characterization, Expression i *Escherichia coli*, and Epitope Analysis of a Two EF-Hand Calcium-Binding Birch Pollen Allergen, Bet v 4," *Biochem. Biophys. Res. Commun*, 239:197-204, 1997.

Valenta, et al., "cDNA Cloning and Expression of Timothy Grass (*Phleum pratense*) Pollen Profilin in *Escherichia coli*: Comparison with Birch Pollen Profilin", *Biochem. Biophys. Res. Commun.* 199: 106-118.

Van Der Stoep, et al., "In vivo and in Vitro IgE Isotype Switching in Human B Lymphocytes: Evidence for a Predominantly direct IgM to IgE class Switch Program", *European J. Immunol*, 24 1307-1311 (1994).

Van Hage-Hamsten, "Skin Test Evaluation of Genetically Engineered Hypoallergenic Derivatives of the Major Birch Pollen Allergen, Bet v 1: Results Obtained with a Mix of Two Recombinant Bet v 1 Fragments and Recombinant Bet v 1 Trimer in a Swedish Population Before the Birch Pollen Season", *J Allergy Clin Immunol.* 104(5): 969-77, Nov. 1999.

Van Hage-Hamsten, et al., "N-Terminal Aminoacid Sequence of Major Allergen of the Mite *Lepidoglyphus destructor*," *J. Allergy Clin. Immunol.* 91:353, 1993.

Van Hoeyveld, et al., "Allergenic and Antigenic Activity of Peptide Fragments in a Whey Hydrolysate Formula", 28(9): 1131-7, Sep. 1998.

Van Kampen, et al., "Analysis of B-cell Epitopes in the N-Terminal Region of Chi t 1 component III using Monoclonal Antibodies," *MolecularImmunol.* 31: 1133-1140 (1994).

Van Millgen, et al., Differences Between Specificities of IgE and IgG4 Antibodies: Studies Using Recombinant Chain 1 and Chain 2 of the Major Cat Allergen *Felis domesticus* (d) I. Clin Exp Allergy 25(3): 247-51, Mar. 1995.

(56) References Cited

OTHER PUBLICATIONS

Van Milligen, et al., "IgE and IgG4 Binding to Synthetic Peptides of the Cat (*Felis domesticus*) Maj Allergen Fel dI" *Int Arch Allergy Immunol*. 103(3): 274-9, 1994.
Van Milligen, et al., "IgE Epitopes on the Cat (*Felis domesticus*) Major Allergen Fel D I: A Study Wit Overlapping Synthetic Peptides", *J Allergy Clin Immunol*. 93(1 Pt 1): 34-43, Jan. 1994.
Van Ree, et al., "Rabbit IgG Directed to a Synthetic C-Terminal Peptide of the Major Grass Pollen Allergen Lol p I Inhibits Human Basophil Histamine Release Induced by Natural p I". *Int Arch Allergy Immunol*. 106(3): 250-7, Mar. 1995.
Van Ree R, et al., "Lol p XI, a New Major Grass Pollen Allergen, is a Member of a Family of Soybean Trypsin Inhibitor-Related Protein", *J. Allergy Clin Immunol*. 95:970-978, 1995.
Van't Hof, et al., "Epitope Mapping of the Cat (*Felis domesticus*) Major Allergen Fel D I by Overlapping Synthetic Peptides and Monoclonal Antibodies Against Native and Denatured Fel D I", *Allergy*, 48(4) 255-63, May 1993.
Van't Hof, et al., Epitope Mapping of the *Dermatophagoides pteronyssinus* House Dust Mite Major Allergen Der p II Using Overlapping Synthetic Peptides, 28(11): 1225-32, Nov. 1991.
Varela, et al., "Primary Structure of Lep d I, the Main *Lepidoglyphus destructor* Allergen", *Eur J. Biochem.*, 225:93-98, 1994.
Villalba, et al., "The Amino Acid Sequence of Ole e I, the Major Allergen From Olive Tree (*Olea europaea*) Pollen", *Europ. J. Biochem.*, 216:863-869, 1993.
Vives, et al., "A Truncated HIV-1 Tat Protein Basic Domain Rapaidly Translocates Through the Plasma Membrane and Accumulates in the Cell Nucleus", *The Journal of Biological Chemistry*, 272(25): 16010-16017, 1997.
Voller, et al., "Enzyme-Linked Immunosorbent Assay," *Manual of Clinical Laboratory Immunology, Rose, ed.*, Chapter 17, Third Edition, 99-109, 1986.
Vrtala, "High Level Expression in *Escherichia coli* and Purification of Recombinant Plant Profilins: Comparison of IgE Binding Capacity and Allergenic Activity," *Biochem. Biophys. Res. Comm*, 226: 42-50, 1996.
Vrtala, et al., "Conversion of the Major Birch Pollen Allergen, Bet v 1, Into Two Nonanaphylactic T Cell Epitope-Containing Fragments: Candidates for a Novel Form of Specific Immunotherapy", *J. Clin. Invest*. 99(7): 1673-81, Apr. 1997.
Vrtala, et al., "Division of the Major Birch Pollen Allergen, Bet v 1, Into Two Non-Anaphylactic Fragments", *Int Arch Allergy Immunol.*, 113: 246-48, 1997.
Wallner, et al., "Immunotherapy with T-Cell Reactive Peptides Derived from Allergens" Allergy 49(5): 302-8, May 1994.
Watanabe, et al., "Primary Structure of an Allergenic Peptide Occurring in the Chymotryptic Hydrolysate of Gluten", *Biosci Biotechnol Biochem*. 59(8): 1596-7, Aug. 1995.
Weber, et al., "Characteristics of the Aspargine-Linked Oligosaccharide from Honey-Bee Venom Phospholipase A2". *Comp. Biochem. Physiol.* 83B: 321-324, 1986.
Weber, et al., "Specific Interaction of IgE Antibodies with a Carbohydrate Epitope of Honey Bee Venom Phospholipase A2", *Allergy*, 42: 464-470, 1987.
Wiedermann, et al., "Suppression of Antigen-Specific T- and B-Cell Responses by Intranasal or Oral Administration of Recombinant Bet v 1, The Major Birch Pollen Allergen, in a Murine Model of Type I Allergy", *J. Allergy Clin Immunol.*, 103(6): 1202-10, Jun. 1999.
Williams, et al., "Indentification of Epitopes Within Beta Lactoglobulin Recognised by Polyclonal Antibodies Using Phage Display and PEPSCAN", *J Immunol Methods*. 213(1): 1-17, Apr. 1998.
Woodfolk, et al., "Trichophyton Antigens Associated with IgE Antibodies and Delayed Type Hypersensitivity", *J. Biol. Chem.* 273:29489-29496, 1998.
Wu, et al., "Isolation and Preliminary Characterization of cDNA Encoding American Cockroach Allergens", *J. Allergy Clin. Immunol.*, 96:352-359, 1995.
Yamamoto, et al., "DNA From Bacteria, But Not From Vertebrates, Induces Interferons, Activates Natural Killer Cells and Inhibits Tumor Growth," *Microbiol. Immunol.* 36(9): 983-97, 1992.
Yang, et al., "Immunologic Characterization of a Recombinant Kentucky Bluegrass (*Poapratensis*) Allergenic Peptide", *J Allergy Clin Immunol*. 87(6): 1096-104, Jun. 1991.
Yeang, et al., "The 14.6 kd Rubber Elongation Factor (Hey b 1) and 24 kd (Hey b 3) Rubber Particle Proteins are Recognized by IgE from Patients with Spina Bifida and Latex Allergy" *J. Allergy Cim Immunol*, 98(3): 628-639, 1996.
Yssel, et al., "Peptide Induced Anergy of Human Allergen-Specific T Cells" *Adv Exp. Med Biol*. 409: 405-10, 1996.
Yunginger, et al., "Fatal Food-Induced Anaphylaxis," *JAMA*, 260: 1450-2, 1988.
*Zimmerman, et al., "CpG Oligodexoynucleotides Trigger Protective and Curative Th1 Responses in Lethal Murine Leishmaniasis," *J. Immunol*. 160(8): 3627-30, 1998.
Stanley et al. Arch. Biochem. Biophys. 342(2):244-253 (1997).
Vrtala et al. J. Clin Invest. 99(7):1673-1681 (1997).

\* cited by examiner

| SEQ. ID. NO. | 90 4 | 100 5 | 110 6 | 120 | 130 7 |
|---|---|---|---|---|---|
| 44. | TNQRSPPGERTRGRQP | GDYDDDRRQP | RREEGGRWG | PAGPRERE | REEDWRQPR |
| 45. | TNQRSPPGER | | | | |
| 46. | QRSPPGERTR | | | | |
| 47. | SPPGERTRGR | | | | |
| 48. | PGERTRGRQP | | | | |
| 49. | ERTRGRQPGD | | | | |
| 50. | TRGRQPGDYD | | | | |
| 51. | GRQPGDYDDD | | | | |
| 52. | QPGDYDDDRR | | | | |
| 53. | GDYDDDRRQP | | | | |
| 54. | YDDDRRQPRR | | | | |
| 55. | DDRRQPRREE | | | | |
| 56. | RRQPRREEGG | | | | |
| 57. | QPRREEGGRW | | | | |
| 58. | RREEGGRWGP | | | | |
| 59. | EEGGRWGPAG | | | | |
| 60. | GGRWGPAGPR | | | | |
| 61. | RWGPAGPRER | | | | |
| 62. | GPAGPRERER | | | | |
| 63. | AGPREREREE | | | | |
| 64. | PREREREED W | | | | |
| 65. | EREEEDWRQ | | | | |
| 66. | EREEDWRQPR | | | | |

```
            55      6      65      7      75
SEQ. ID. NO. |      |      |       |      |
    67.     DSYE RDPYSP SQ DPYSPS PYDR

68.     DSYE RDPYSP
    69.       YE RDPYSP SQ
    70.          RDPYSP SQ DP
    71.              PYSP SQ DPYS
    72.                SPSQ DPYSPS
    73.                  SQ DPYSPS PY
    74.                     DPYSPS PYDR
```

Figure 6

```
            299                         321
SEQ. ID. NO. |                           |
    75.     EEEYDEDE YEYDEEDRR RGRGSR
    76.     EEEYDEDE YEYDEED
    77.       EYDEDE YEYDEEDRR
    78.         DEDE YEYDEEDRR RG
    79.           DE YEYDEEDRR RGRG
    80             YEYDEEDRR RGRGSR
    81.              YDEEDRRR GRGSRGR
```

Figure 7

MICROBIAL DELIVERY SYSTEM

PRIORITY INFORMATION

The present application is a continuation of U.S. patent application Ser. No. 10/728,323, filed Dec. 4, 2003, which is a divisional of U.S. patent application Ser. No. 09/731,375, filed Dec. 6, 2000, which claims the benefit of U.S. Provisional Patent Application Ser. No. 60/195,035, filed Apr. 6, 2000; the entire contents of each of which are incorporated herein by reference.

RELATED APPLICATIONS

The present invention is generally in the area of controlled delivery of antigens for use in vaccination or induction of tolerance to allergens, and in particular relates to cellular delivery of proteins and polypeptides. This application is related to U.S. Ser. No. 60/169,330 entitled "Controlled Delivery of Antigens" filed Dec. 6, 1999; U.S. Ser. No. 09/141,220 entitled "Methods and Reagents for Decreasing Clinical Reaction to Allergy" filed Aug. 27, 1998; U.S. Ser. No. 09/455,294 entitled "Peptide Antigens" filed Dec. 6, 1999; U.S. Ser. No. 09/494,096 filed Jan. 28, 2000 entitled "Methods and Reagents for Decreasing Clinical Reaction to Allergy" by Bannon et al.; and U.S. Ser. No. 09/527,083 entitled "Immunostimulatory Nucleic Acids and Antigens" by Caplan filed Mar. 16, 2000; the teachings of which are all incorporated herein by reference in their entirety.

SEQUENCE LISTING

In accordance with 37 CFR §1.52(e)(5), the present specification makes reference to a Sequence Listing (submitted electronically as a .txt file named "Sequence_Listing.txt" May 20, 2013). The .txt file was generated on May 15, 2013 and is 30 KB in size. The entire contents of the Sequence Listing are herein incorporated by reference, with the intention that, upon publication (including issuance), this incorporated sequence listing will be inserted in the published document immediately before the claims.

BACKGROUND OF THE INVENTION

Allergic reactions pose serious public health problems worldwide. Pollen allergy alone (allergic rhinitis or hay fever) affects about 10-15% of the population, and generates huge economic costs. For example, reports estimate that pollen allergy generated $1.8 billion of direct and indirect expenses in the United States in 1990 (*Fact Sheet*, National Institute of Allergy and Infectious Diseases; McMenamin, *Annals of Allergy* 73:35, 1994). Asthma, which can be triggered by exposure to antigens, is also a serious public health problem, and like anaphylactic allergic reactions, can lead to death in extreme cases. Asthma currently accounts for millions of visits yearly to hospitals and is increasing in frequency. The only treatment currently available is for alleviation of symptoms, for example, to relieve constriction of airways. More serious than the economic costs associated with pollen and other inhaled allergens (e.g., molds, dust mites, animal danders) is the risk of an anaphylactic allergic reaction observed with allergens such as food allergens, insect venoms, drugs, and latex.

Allergic reactions result when an individual's immune system overreacts, or reacts inappropriately, to an encountered antigen. Typically, there is no allergic reaction the first time an individual is exposed to a particular antigen. However, it is the initial response to an antigen that primes the system for subsequent allergic reactions. In particular, the antigen is taken up by antigen presenting cells (APC; e.g., macrophages and dendritic cells) that degrade the antigen and then display antigen fragments to T cells. T cells, in particular $CD4^+$ "helper" T-cells, respond by secreting a collection of cytokines that have effects on other immune system cells. The profile of cytokines secreted by responding $CD4^+$ T cells determines whether subsequent exposures to the antigen will induce allergic reactions. Two classes of $CD4^+$ T cells (Th1 and Th2) influence the type of immune response that is mounted against an antigen.

Th2 cells can secrete a variety of cytokines and interleukins including IL-4, IL-5, IL-6, IL-10 and IL-13. One effect of IL-4 is to stimulate the maturation of B cells that produce IgE antibodies specific for the antigen. Allergic responses to allergens are characterized by the production of antigen-specific IgE antibodies which are dependent on help from IL-4 secreting $CD4^+$ T cells. These antigen-specific IgE antibodies attach to receptors on the surface of mast cells, basophils and eosinophils, where they act as a trigger to initiate a rapid allergic reaction upon the next exposure to antigen. When the individual encounters the antigen a second time, the antigen is quickly bound by these surface-associated IgE molecules. Each antigen typically has more than one IgE binding site, so that the surface-bound IgE molecules quickly become crosslinked to one another through their simultaneous (direct or indirect) associations with antigen. Such cross-linking induces mast cell degranulation, resulting in the release of histamines and other substances that trigger allergic reactions. Individuals with high levels of IgE antibodies are known to be particularly prone to allergies.

Current treatments for allergies involve attempts to "vaccinate" a sensitive individual against a particular allergen by periodically injecting or treating the individual with a crude suspension of the raw allergen. The goal, through controlled administration of known amounts of antigen, is to modulate the IgE response mounted in the individual. If the therapy is successful, the individual's IgE response is diminished, or can even disappear. However, the therapy requires several rounds of vaccination, over an extended time period (3-5 years), and very often does not produce the desired results. Moreover, certain individuals suffer anaphylactic reactions to the vaccines, despite their intentional, controlled administration.

Clearly, there is a need for treatments and preventive methods for patients with allergies to allergens that elicit serious allergic responses including anaphylaxis.

SUMMARY OF THE INVENTION

The present invention provides methods and compositions for modulating the immune response in a subject. It is an aspect of the present invention to provide a method of treating or preventing undesirable allergic reactions and anaphylactic allergic reactions to allergens in a subject. Methods of the present invention involve administering to subjects, microorganisms that express or produce allergens of interest. Without being limited to the proposed mechanism of action, after administration the microorganisms are taken up by antigen-presenting cells in the subject where the expressed antigens are released. After being processed inside the antigen-presenting cells and displayed on the cell surface, the processed antigens activate T-cell mediated immune responses. Use of genetically modified microorganisms to express and deliver allergens to a subject therefore reduces the exposure of the allergens to the subject's IgE antibodies, which lead to allergic reactions and possibly anaphylaxis. The present invention therefore reduces the risk of anaphylaxis during immunotherapy. Furthermore, the microorganisms may act as a natural adjuvant to enhance desirable Th1-type immune responses.

In a preferred embodiment, microorganisms are genetically modified to express selected polypeptides or proteins, and are used as delivery vehicles in accordance with the present invention. Such microorganisms include but are not limited to bacteria, viruses, fungi (including yeast), algae, and protozoa. Generally, preferred microorganisms for use in accordance with the present invention are single cell, single spore or single virion organisms. Additionally, included within the scope of the present invention are cells from multicellular organisms which have been modified to produce a polypeptide of interest.

In a particularly preferred embodiment, bacteria or yeast are used as microorganisms to express and deliver allergenic proteins to individuals to treat or prevent allergic responses, including anaphylactic allergic responses, to the allergens. Gram-positive and gram-negative bacteria may be used in the present invention has delivery vehicles. Antigens expressed by the bacteria may be secreted or non-secreted. Secretion of proteins may involve secretion into the cellular medium. For gram-negative bacteria and yeast, secretion may involve secretion into the periplasm. Secretion of polypeptides may be facilitated by secretion signal peptides. In certain preferred embodiments microorganisms expressing allergenic compounds may be administered to subjects in compositions as attenuated microorganisms, non-pathogenic microorganisms, non-infectious microorganisms, or as killed microorganisms. Preferably, the killed microorganisms are killed without degrading the antigenic properties of the polypeptides.

In another preferred embodiment, the allergens utilized are allergens found in foods, venom, drugs and a rubber-based products. Particularly preferred protein allergens are found in foods and venoms that elicit anaphylactic allergic responses in subjects who are allergic to the allergens. Included in the present invention are peptides and polypeptides whose amino acid sequences are found in the proteins allergens in nature. Also included in the present invention are allergens that have modifications that reduce the ability of the peptides, polypeptides and proteins to bind and crosslink IgE antibodies. Also included in the present invention are non-peptide allergens that are produced by microorganisms and include for example antibiotics such as penicillin.

In another aspect of the invention, compositions for use in treating or prevent allergic and anaphylactic allergic responses in a subject comprise microorganisms that have been engineered by the hand of man, and preferably by the introduction of one or more introduced nucleic acids, to produce allergens in accordance with the present invention. In certain preferred embodiments, the produced allergens are peptides, polypeptides, or proteins encoded by the introduced nucleic acids(s).

BRIEF DESCRIPTION OF FIGURES

FIG. 2. Determination of protein produce per cell. The optical density (O.D.) of the HIS-tagged Ara h 2 allergen was determined from an immunoblot where different concentrations of E. coli extract has been electrophoresed on SDS-PAGE gels. The allergen O.D. was used to estimate the amount of protein produced by that extract.

FIG. 5 shows an example of how IgE binding epitopes were mapped to a specific amino acid sequence on the Ara h 1 allergen. In particular, FIG. 5 depicts twenty-two 10-mer peptides (SEQ ID NOs. 45-66) that span amino acid residues 82-133 (SEQ ID NO. 44) of the Ara h 1 allergen (SEQ ID NO. 2). This region of the Ara h 1 allergen includes epitopes 4, 5, 6, and 7, as identified in Table 1.

FIG. 6 shows an example of how IgE binding epitopes were mapped to a specific amino acid sequence on the Ara h 2 allergen. In particular, FIG. 6 depicts seven 10-mer peptides (SEQ ID NOs. 68-74) that span amino acid residues 55-76 (SEQ ID NO. 67) of the Ara h 2 allergen (SEQ ID NO. 4). This region of the Ara h 2 allergen includes epitopes 6 and 7 as identified in Table 2.

FIG. 7 shows an example of how IgE binding epitopes were mapped to a specific amino acid sequence on the Ara h 3 allergen. In particular, FIG. 7 depicts six 15-mer peptides (SEQ ID NOs. 76-81) that span amino acid residues 299-321 (SEQ ID NO. 75) of the Ara h 3 allergen (SEQ ID NO. 6). This region of the Ara h 3 allergen includes epitope 4 as identified in Table 3.

DEFINITIONS

Figure 1:
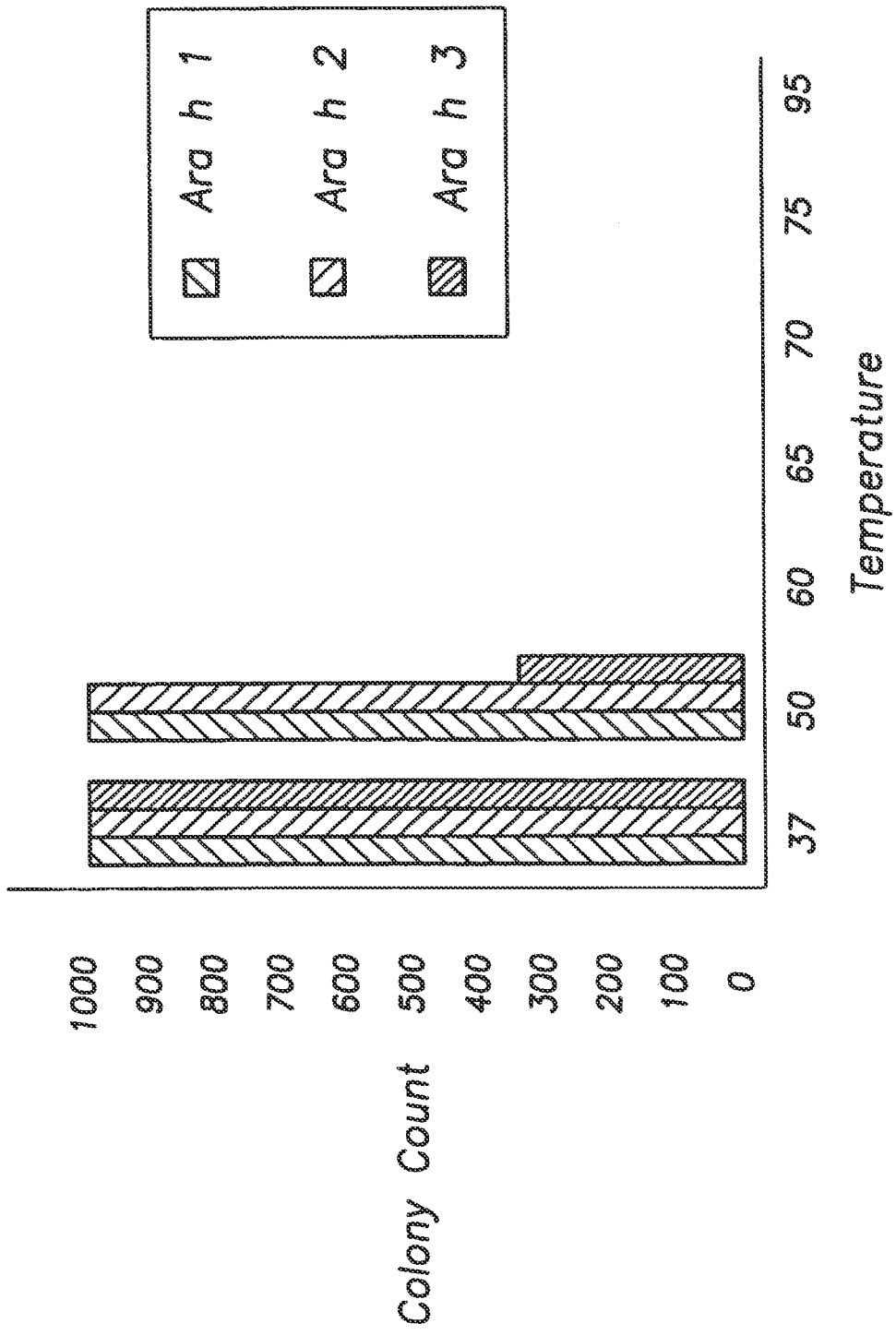
FIG. 1. Experiments designed to determine the optimal temperature for heat-killing bacteria (E. coli) are depicted in graphic form. The number of surviving colonies in aliquots of samples are shown as a function of temperature (Celsius).
Figure 3:
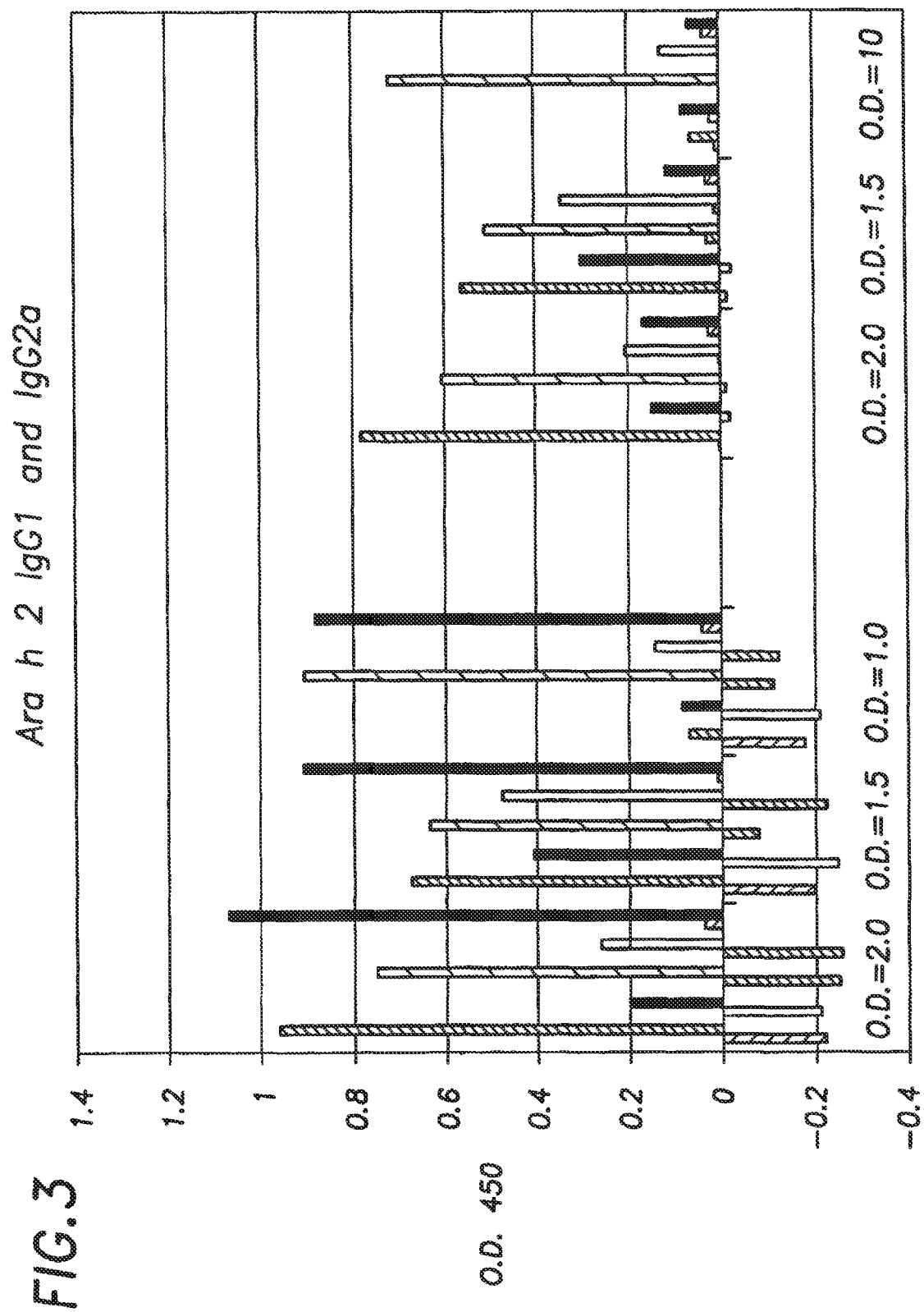
FIG. 3. Results of ELISA analysis of Ara h 2-specific IgG antibodies produced in mice following injection of E. coli producing Ara h 2. IgG1 is on the left and IgG2a is on the right.
Figure 4:
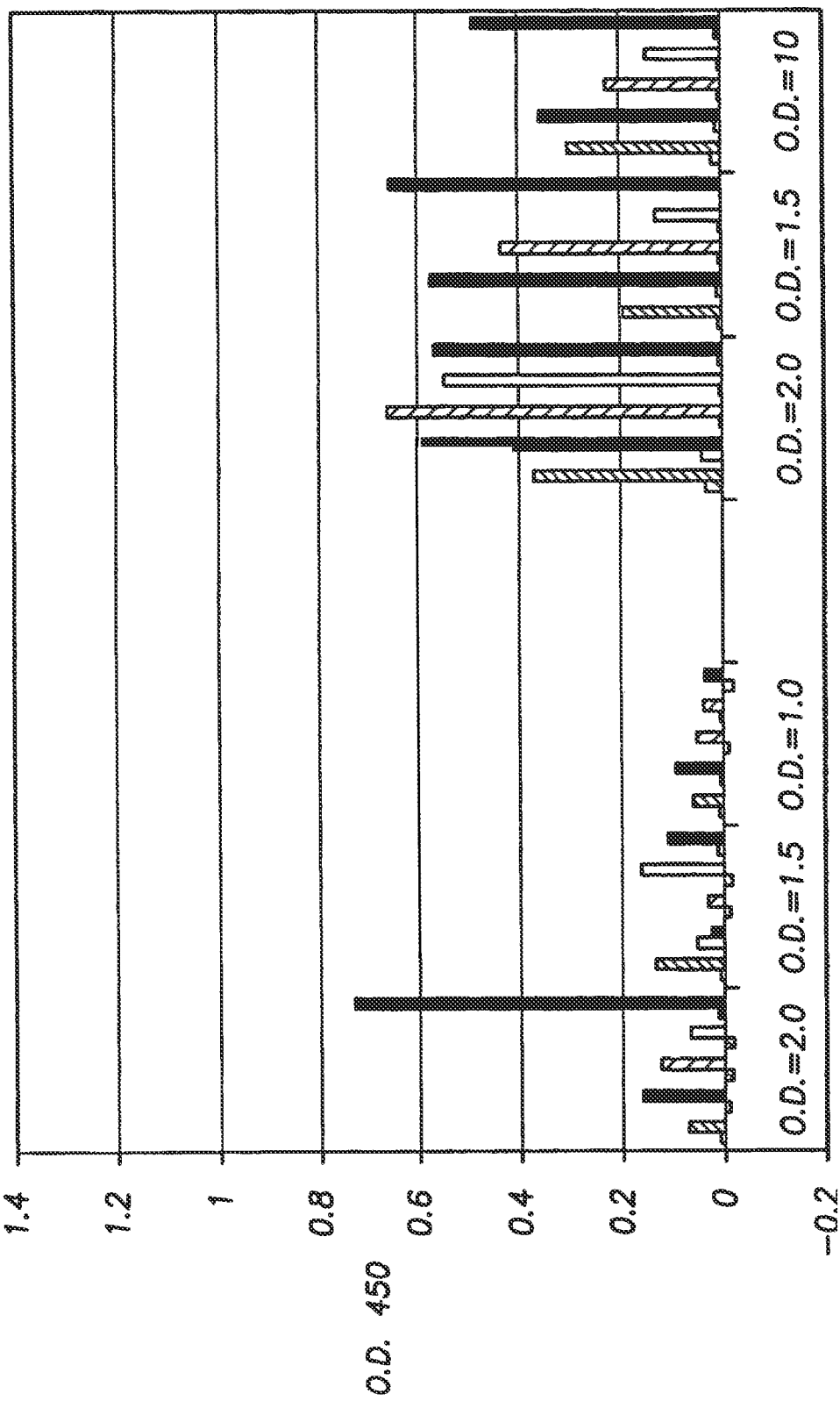
FIG. 4. Results of ELISA analysis of Ara h 3-specific IgG antibodies produced in mice following injection of E. coli producing Ara h 3. IgG1 is on the left and IgG2a is on the right.

"Allergen": An "allergen" is an antigen that (i) elicits an IgE response in an individual; and/or (ii) elicits an asthmatic reaction (e.g., chronic airway inflammation characterized by eosinophilia, airway hyperresponsiveness, and excess mucus production), whether or not such a reaction includes a detectable IgE response). Preferred allergens for the purpose of the present invention are peptide, polypeptide and protein allergens. An exemplary list of protein allergens is presented as an Appendix. This list was adapted from ftp://biobase.dk/pub/who-iuis/allergen.list (updated on Mar. 1, 2000), which provides lists of known allergens. Other preferred allergens are chemical compounds such as small molecules that are produced by proteins. In some embodiments, an allergen is a subset of antigens which elicits IgE production in addition to other isotypes of antibodies.

"Allergic reaction": An allergic reaction is a clinical response by an individual to an antigen. Symptoms of allergic reactions can affect cutaneous (e.g., urticaria, angioedema, pruritus), respiratory (e.g., wheezing, coughing, laryngeal edema, rhinorrhea, watery/itching eyes) gastrointestinal (e.g., vomiting, abdominal pain, diarrhea), and/or cardiovascular (if a systemic reaction occurs) systems. For the purposes of the present invention, an asthmatic reaction is considered to be a form of allergic reaction. A decreased allergic reaction is characterized by a decrease in clinical symptoms following treatment of symptoms associated with exposure to an allergen, which can involve respiratory, gastrointestinal, skin, eyes, ears and mucosal surfaces in general.

"Anaphylactic antigen": An "anaphylactic antigen" according to the present invention is an antigen (or allergen) that is recognized to present a risk of anaphylactic reaction in allergic individuals when encountered in its natural state, under natural conditions. For example, for the purposes of the present invention, pollens and animal danders or excretions (e.g., saliva, urine) are not considered to be anaphylactic antigens. On the other hand, food antigens, insect antigens, drugs, and rubber (e.g., latex) antigens latex are generally considered to be anaphylactic antigens. Food antigens are particularly preferred anaphylactic antigens for use in the practice of the present invention. Particularly interesting anaphylactic antigens are those (e.g., nuts, seeds, and fish) to which reactions are commonly so severe as to create a risk of death.

"Anaphylaxis" or "anaphylactic reaction", as used herein, refers to an immune response characterized by mast cell degranulation secondary to antigen-induced cross-linking of the high-affinity IgE receptor on mast cells and basophils with subsequent mediator release and the production of pathological responses in target organs, e.g., airway, skin digestive tract and cardiovascular system. As is known in the art, the severity of an anaphylactic reaction may be monitored, for example, by assaying cutaneous reactions, puffiness around the eyes and mouth, and/or diarrhea, followed by respiratory reactions such as wheezing and labored respiration. The most severe anaphylactic reactions can result in loss of consciousness and/or death.

"Antigen": An "antigen" is (i) any compound or composition that elicits an immune response; and/or (ii) any compound that binds to a T cell receptor (e.g., when presented by an MHC molecule) or to an antibody produced by a B-cell. Those of ordinary skill in the art will appreciate that an antigen may be collection of different chemical compounds (e.g., a crude extract or preparation) or a single compound (e.g., a protein). Preferred antigens are peptide, polypeptide or protein antigens. In some embodiments, an antigen is a molecule that elicits production of antibody (a humoral response) or an antigen-specific reaction with T cells (a cellular response).

"Antigen presenting cells": "Antigen presenting cells" or APCs" include known APCs such as Langerhans cells, veiled cells of afferent lymphatics, dendritic cells and interdigitating cells of lymphoid organs. The term also includes mononuclear cells such as lymphocytes and macrophages which take up polypeptides and proteins according to the invention. In some embodiments, an antigen presenting cell (an APC) is a cell which processes and presents peptides to T cells to elicit an antigen-specific response.

"Attenuation": "Attenuation" of microorganisms as used herein refers to the manipulation of the microorganisms so that the microorganisms do not induce significant toxic reactions in individuals or laboratory test animals. The manipulations include genetic methods and are well known in the art.

An epitope is a binding site including an amino acid motif of between approximately six and fifteen amino acids which can be bound by either an immunoglobulin or recognized by a T cell receptor when presented by an antigen presenting cell in conjunction with the major histocompatibility complex (MHC). A linear epitope is one where the amino acids are recognized in the context of a simple linear sequence. A conformational epitope is one where the amino acids are recognized in the context of a particular three dimensional structure. An immunodominant epitope is one which is bound by antibody in a large percentage of the sensitized population or where the titer of the antibody is high, relative to the percentage or titer of antibody reaction to other epitopes present in the same protein.

"IgE binding site": An IgE binding site is a region of an antigen that is recognized by an anti-antigen IgE molecule. Such a region is necessary and/or sufficient to result in (i) binding of the antigen to IgE; (ii) cross-linking of anti-antigen IgE; (iii) degranulation of mast cells containing surface-bound anti-antigen IgE; and/or (iv) development of allergic symptoms (e.g., histamine release). In general, IgE binding sites are defined for a particular antigen or antigen fragment by exposing that antigen or fragment to serum from allergic individuals (preferably of the species to whom inventive compositions are to be administered). It will be recognized that different individuals may generate IgE that recognize different epitopes on the same antigen. Thus, it is typically desirable to expose antigen or fragment to a representative pool of serum samples. For example, where it is desired that sites recognized by human IgE be identified in a given antigen or fragment, serum is preferably pooled from at least 5-10, preferably at least 15, individuals with demonstrated allergy to the antigen. Those of ordinary skill in the art will be well aware of useful pooling strategy in other contexts.

"Immunologic inducing agents": The term "immunological inducing agents" is used herein as agents that prompt the expression of Th1 stimulating cytokines by T-cells and include factors such as, CD40, CD40 ligand, oligonucleotides containing CpG motifs, TNF, and microbial extracts such as preparations of *Staphylococcus aureus*, heat killed *Listeria*, and modified cholera toxin.

Immunostimulatory sequences are oligodeoxynucleotides of bacterial, viral or invertebrate origin that are taken-up by APCs and activate them to express certain membrane receptors (e.g., B7-1 and B7-2) and secrete various cytokines (e.g., IL-1, IL-6, IL-12, TNF). These oligodeoxynucleotides containing unmethylated CpG motifs cause brisk activation and when injected into animals in conjunction with antigen, appear to skew the immune response to a Th1-type response. See, for example, Yamamoto, et al., *Microbiol. Immunol.* 36, 983 (1992); Krieg, et al., *Nature* 374, 546-548 (1995); Pisetsky, *Immunity* 5, 303 (1996); and Zimmerman, et al., *J. Immunol.* 160, 3627-3630 (1998).

"Inducible promoter": The term "inducible promoter", as used herein, means a promoter site which is activated directly by the presence or absence of a chemical agent or indirectly by an environmental stimulus such as temperature changes. A promoter is the region of DNA at which the enzyme RNA polymerase binds and initiates the process of gene transcription.

"Mast cell": As will be apparent from context, the term "mast cell" is often used herein to refer to one or more of mast cells, basophils, and other cells having IgE receptors, which when activated by crosslinking bound IgE molecules, releases histamines, vasodilators, and/or other mediators of allergic responses.

"Microorganisms": "Microorganisms" as used herein are cells, bacteria, fungi, viruses, algae, and protozoa. Preferred microorganisms can be genetically manipulated to produce a desired polypeptide(s).

"Peptide": According to the present invention, a "peptide" comprises a string of at least three amino acids linked together by peptide bonds. Inventive peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

A peptide or polypeptide is derived from a protein if the amino acid sequence of the peptide or polypeptide is found within the amino acid sequence of the protein. The sequences are preferably identical but may have a sequence homology between approximately 80-100%. It is also recognized that amino acid residues may be replaced with other amino acids residues with similar physical properties such as hydrophobicity, hydrophilicity, charge, aromatic structures and polarity.

"Reduced IgE binding": An inventive composition or antigen is considered to have "reduced IgE binding" if it demonstrates a lower level of interaction with IgE when compared with unmodified antigen in any available assay. For example, a modified antigen is considered to have reduced IgE binding if (i) its affinity for anti-antigen IgE (assayed, for example, using direct binding studies or indirect competition studies) is reduced at least about 2-5 fold, preferably at least about 10, 20, 50, or 100 fold as compared with intact antigen; (ii) ability of the modified antigen to support cross-linking of anti-antigen IgE is reduced at least about 2-fold, preferably at least about 5, 10, 20, 50, or 100 fold as compared with intact antigen; (iii) mast cells containing surface-bound anti-antigen IgE degranulate less (at least about 2 fold, preferably at least about 3, 5, 10, 20, 50, or 100 fold less) when contacted with modified as compared with unmodified antigen; and/or (iv) individuals contacted with modified antigen develop fewer (at least about 2 fold, preferably at least about 3, 5, 10, 20, 50, or 100 fold fewer) allergic symptoms, or developed symptoms are reduced in intensity when exposed to modified antigens as compared with unmodified antigens.

"Secretion signals": A secretion signal is any amino acid sequence which when conjugated to a peptide, polypeptide or protein facilitates the transport of the conjugate fusion proteins across cell membranes. For uses of secretion signals in microorganisms, transport of fusion proteins involves crossing an inner membrane into the periplasm. It is preferred that secretion signals also facilitate transport of fusion proteins across an outer membrane into an extracellular medium. Secretion of proteins into the extracellular medium is considered "excretion".

"Sensitized mast cell": A "sensitized" mast cell is a mast cell that has surface-bound antigen specific IgE molecules. The term is necessarily antigen specific. That is, at any given time, a particular mast cell will be "sensitized" to certain antigens (those that are recognized by the IgE on its surface) but will not be sensitized to other antigens.

"Small molecules": As used herein, the term "small molecule" refers to a compound either synthesized in the laboratory or found in nature. Typically, a small molecule is organic and is characterized in that it contains several carbon-carbon bonds, and has a molecular weight of less than 1500 daltons, although this characterization is not intended to be limiting for the purposes of the present invention. Examples of "small molecules" that are allergens include without limitation penicillin, alcohols, and aspirin. Non-organic small molecule allergens include sulfites present in wine, for example.

"Susceptible individual": According to the present invention, a person is susceptible to an allergic reaction if (i) that person has ever displayed symptoms of allergy after exposure to a given antigen; (ii) members of that person's genetic family have displayed symptoms of allergy against the allergen, particularly if the allergy is known to have a genetic component; and/or (iii) antigen-specific IgE are found in the individual, whether in serum or on mast cells.

"Th1 response" and "Th2 response": Certain preferred peptides, polypeptides, proteins and compositions of the present invention are characterized by their ability to suppress a Th2 response and/or to stimulate a Th1 response preferentially as compared with their ability to stimulate a Th2 response. Th1 and Th2 responses are well-established alternative immune system responses that are characterized by the production of different collections of cytokines and/or cofactors. For example, Th1 responses are generally associated with production of cytokines such as IL-1β, IL-2, IL-12, IL-18, IFNα, IFNγ, TNFβ, etc; Th2 responses are generally associated with the production of cytokines such as IL-4, IL-5, IL-10, etc. The extent of T cell subset suppression or stimulation may be determined by any available means including, for example, intra-cytoplasmic cytokine determination. In preferred embodiments of the invention, Th2 suppression is assayed, for example, by quantitation of IL-4, IL-5, and/or IL-13 in stimulated T cell culture supernatant or assessment of T cell intra-cytoplasmic (e.g., by protein staining or analysis of mRNA) IL-4, IL-5, and/or IL-13; Th1 stimulation is assayed, for example, by quantitation of IFNα, IFNγ, IL-2, IL-12, and/or IL-18 in activated T cell culture supernatant or assessment of intra-cytoplasmic levels of these cytokines.

DESCRIPTION OF CERTAIN PREFERRED EMBODIMENTS

The present invention provides compositions and methods for modulating the immune response in a subject. It is an aspect of the present invention that undesirable allergic immune responses to antigens in a subject are treated or prevented by administering modified cells, virions, or spores ("microorganisms") that express allergens of interest. By using genetically modified microorganisms to express and deliver allergens, exposure of the allergens to the subject's IgE-mediated allergic immune response is reduced or eliminated. Without limitation to the mechanisms proposed, it is expected that the modified microorganisms of the present invention are engulfed by antigen-presenting cells (APCs) such as macrophages and dendritic cells without exposing allergens to IgE antibodies. Once inside the APCs, the expressed allergens are released by lysis of the microorganisms or secretion of the antigen by the microorganisms. The allergens are then processed, for example through partial digestion by the APCs, and displayed on the cell surface.

Once the processed antigens are displayed on the cell surface, activation of the cytotoxic T cell response and helper T cell response promotes cellular immune response and Th1-mediated B cell response to protein allergens. In addition, the processed antigens have a reduced ability (or no ability) to bind and crosslink IgE antibodies located on the surface of mast cells and basophils leading to the release of histamines and other vasodilators responsible for allergic and sometimes fatal anaphylactic responses.

Host Microorganisms

Any microorganism capable of expressing (e.g., by expression of polypeptide or protein allergens, or by expression of polypeptide or protein enzymes involved in synthesis of small molecule allergens) allergens may be used as delivery vehicles in accordance with the present invention. Such microorganisms include but are not limited to bacteria, viruses, fungi (including yeast), algae, and protozoa. Generally, microorganisms are single cell, single spore or single virion organisms. Additionally, included within the scope of the present invention are cells from multi-cellular organisms which have been modified to produce a polypeptide of interest. Microorganisms that can be genetically manipulated to produce a desired polypeptide are preferred. (Ausubel et al. *Current Protocols in Molecular Biology*. Wiley and Sons, Inc. 1999, incorporated herein by reference) Genetic manipulation includes mutation of the host genome, insertion of genetic material into the host genome, deletion of genetic material of the host genome, transformation of the host with extrachromosomal genetic material, transformation with linear plasmids, transformation with circular plasmids, insertion of genetic material into the host (e.g., injection of mRNA), insertion of transposons, and chemical modification of genetic material. Methods for constructing nucleic acids (including an expressible gene), and introducing such nucleic acids into an expression system to express the encoded protein are well established in the art (see, for example, Sambrook et al., *Molecular Cloning: A Laboratory Manual*, 2nd Ed., Cold Spring Harbor Laboratory Press, Cold Spring Harbor, N.Y., 1989, incorporated herein by reference).

Use of microorganisms such as bacteria and yeast for allergen delivery in accordance with the present invention offers many advantages over delivery of allergens that are not encapsulated inside microorganisms for immunotherapy. Generally, microorganisms, such as bacteria, are known to act as an adjuvant (for a review, see for example, Freytag et al. *Curr Top Microbiol Immunol* 236:215-36, 1999). Therefore, use of microorganisms to delivery allergens to subjects, and APCs of subjects, provides protection of the allergen from IgE-mediated allergic responses and also provides an adjuvant effect which elicits a Th1-type immune response from an individual susceptible to allergic responses. In addition, use of non-pathogenic, non-infectious, attenuated and/or killed microorganisms reduces or eliminates toxicity which may be associated with allergen delivery vehicles.

In a preferred embodiment, bacteria are used as protein delivery microorganisms. Generally, bacteria are classified as gram-negative or gram-positive depending on the structure of the cell walls. Those skilled in the art are capable of identifying gram-negative and gram-positive bacteria which may be used to express proteins in accordance with the present invention. Non-limiting examples of genera and species of gram-negative bacteria include *Escherichia coli, Vibro cholera, Salmonella, Listeria, Legionella, Shigella, Yersenia, Citrobacter, Enterobacter, Klebsiella, Morganella, Proteus, Providencia, Serratia, Plesiomonas, Aeromonas*. Non-limiting examples of genera and species of gram-positive bacteria which may be used in the present invention include *Bacillus subtilis, Sporolactobacillus, Clostridium, Arthrobacter, Micrococcus, Mycobacterium, Peptococcus, Peptostreptococcus*, and *Lactococcus*.

Gram-negative bacterial systems for use as delivery vehicles are known and may be used in the present invention. For example, *E. coli* is a well-studied bacteria, and methods of protein expression in *E. coli* are well-established. Most strains of *E. coli* have the advantage of being non-pathogenic since *E. coli* is found naturally in the gut. Therefore, *E. coli* is preferred as a delivery vehicle in the present invention. In addition, Calderwood et al. (U.S. Pat. No. 5,747,028) utilize *Vibrio cholerae* as a delivery vehicle for production of antigens for use as a live vaccine against infectious organisms. Miller and Mekalanos (U.S. Pat. No. 5,731,196) utilize *Salmonella* as delivery vehicle for production of antigens for use as a live vaccine against infectious organisms. Hess et al. (*Proc. Natl. Acad. Sci. USA* 93:1458-1463, 1996) utilize recombinant attenuated *Salmonella* which secretes antigenic determinants of *Listeria* as a live vaccine to protect against listeriosis. Donner et al. (WO 98/50067) utilize attenuated *Salmonella typhimurium* as a gram-negative host for secretion of polypeptides for controlling fertility and also teach that other attenuated gram-negative strains including *Yersinia* may be used to express and secrete such polypeptides.

Gram-positive bacteria have also been studied as delivery vehicles for proteins to modulate an immune response in a subject. WO 97/14806 describes the use of *Lactococcus* to deliver polypeptides into a body to enhance the immune response to the polypeptides. However, WO 97/14806 does not teach the use of *Lactococcus* to treat patients with food allergies and venom allergies which may result in anaphylaxis In another preferred embodiment, yeast are used as protein delivery microorganisms. It is well known that yeast are amenable to genetic manipulation to express a protein or proteins of choice (Ausubel et al. supra). Furthermore, in general most yeast are non-pathogenic. Without limitation to these species, two well-characterized species of yeast are the budding yeast *Saccharomyces cerevisiae*, and the fission yeast, *Schizosaccharomyces pombe*. Moreover, the administration of yeast that express protein antigens to alter an immune response has been studied. Duke et al. (U.S. Pat. No. 5,830,463; "Duke") describe the use of yeast to express proteins after administration of the yeast to a mammal. However, Duke does not teach the use of yeast to treat patients with food allergies and venom allergies which may result in anaphylaxis.

Microorganisms of the present invention may be administered to a subject as live or dead microorganisms. Preferably if the microorganisms are administered as live microorganisms, they are non-pathogenic or attenuated pathogenic microorganisms. For applications of the invention where live microorganisms are administered to individuals, preferably the microorganisms are attenuated and/or are administered in suitable encapsulation materials and/or as pharmaceutical compositions as vaccines to decrease an individuals immune response to the microorganism and/or allergenic compounds. Generally, attenuation involves genetically modifying the infectious pathogenic microorganism to reduce or eliminate the infectious ability of the microorganism. Preferably, the microorganism is attenuated such that an individual inoculated with the microorganism does not suffer any cytotoxic effects from the presence of the microorganism. Particularly preferred attenuated microorganisms are infectious intracellular pathogens which are phagocytosed by antigen-presenting cells in individuals who are exposed to the microorganism. Examples of microorganisms which are intracellular pathogens include *Salmonella, Mycobacterium, Leishmania, Legionella, Listeria*, and *Shigella*.

Microorganisms of the present invention may be administered to subjects after killing the microorganisms. Any method of killing the microorganisms may be utilized that does not greatly alter the antigenicity of the expressed polypeptides. Methods of killing microorganism include but are not limited to using heat, antibiotics, chemicals such as iodine, bleach, ozone, and alcohols, radioactivity (i.e. irradiation), UV light, electricity, and pressure. Preferred methods of killing microorganisms are reproducible and kill at least 99% of the microorganisms. Particularly preferred is the use of heat above 50 degrees Celsius for a period of time that kills greater than 99% of the cells and preferably 100% of the cells.

Inducible Systems

In another preferred embodiment, the inventive expression of allergens by microorganisms is regulated so that synthesis occurs at a controlled time after the live microorganism is administered to an individual. Preferably the induction of protein synthesis is regulated so that activation occurs after the microorganism(s) is taken up by antigen-presenting cells (APCs) and phagocytosed into the endosome. A desirable result of this regulation is that production of the allergen of interest occurs inside the APCs and therefore reduces or eliminates the exposure of the allergen to IgE molecules bound to the surface of histamine-releasing mast cells and basophils. This reduces or eliminates the risk of anaphylaxis during administration of microorganisms that produce anaphylactic antigens.

Any method of controlling protein synthesis in the microorganism may be used in accordance with the present invention. Preferably, the method of controlling protein synthesis utilizes an inducible promoter operatively-linked to the gene of interest (e.g., a gene which encodes a signal peptide and protein antigen). Many systems for controlling transcription of a gene using an inducible promoter are known (Ausubel et al. *Current Protocols in Molecular Biology*. Wiley and Sons. New York. 1999). Generally, inducible systems either utilize activation of the gene or derepression of the gene. It is preferred that the present invention utilizes activation of a gene to induces transcription. However, inducible systems using derepression of a gene may also be used in the present invention. Systems using activation are preferred because these systems are able to tightly control inactivation (and hence basal level synthesis) since derepression may result in low levels of transcription if the derepression is not tight.

Methods of inducing transcription include but are not limited to induction by the presence or absence of a chemical agent, induction using a nutrient starvation inducible promoter, induction using a phosphate starvation inducible promoter and induction using a temperature sensitive inducible promoter. A particularly preferred system for regulating gene expression utilizes tetracycline controllable expression system. Systems which utilize the tetracycline controllable expression system are commercially available (see for example, Clontech, Palo Alto, Calif.).

Another particularly preferred system for regulating gene expression utilizes an ecdysone-inducible expression system which is also commercially available (Invitrogen, Carlsbad Calif.). The ecdysone-inducible expression system is based on the ability of ecdysone which is an insect hormone, to activate gene expression by binding to the ecdysone receptor. The expression system utilizes a modified heterologous protein containing the ecdysone receptor, a viral transactivation domain (from VP16) and the retinoid X receptor derived from mammalian cells to bind to a modified ecdysone response element in the presence of a ligand such as ecdysone or an analog (e.g. muristerone A, ponasterone A).

It is preferred that inducible systems for use in the present invention utilize inducing agents that are non-toxic to mammalians cells including humans. Furthermore, it is preferred that transcriptional inducing agents permeate cells membranes. More specifically for activation of protein synthesis in microorganisms after phagocytosis by APCs, transcriptional inducing agents must be able to pass through cells membranes of the APC and cell membranes of the microorganism to activate the expression of genes encoding protein allergens in accordance with the present invention. Since both tetracycline and ecdysone are able to pass through cell membranes and are non-toxic, tetracycline-inducible systems and ecdysone-inducible systems are ideally suited for use in the present invention. However, the use of inducible systems in the present invention is not limited to those systems.

It is also preferred that bacteria that have not been phagocytosed are killed before induction of genes expressing polypeptide allergens of interest. A preferred method of killing bacteria is to use antibiotics which are not permeable to mammalian cell membranes such that only bacteria that are not phagocytosed are killed. The use of antibiotics in accordance with the present embodiment reduces or eliminates the production of polypeptides by bacteria outside antigen presenting cells. It is important to reduce or eliminate exposure of allergen-producing bacteria to the immune system, especially bacteria that secrete polypeptides, which could elicit a potentially lethal anaphylactic reaction in an individual. Those having ordinary skill in the art are readily aware of antibiotics which may be used. Such antibiotics include but are not limited to penicillin, ampicillin, cephalosporin, griseofulvin, bacitracin, polymyxin b, amphotericin b, erythromycin, neomycin, streptomycin, tetracycline, vancomycin, gentamicin, and rifamycin Secretion Signals In another embodiment of the present invention, expressed allergens (and/or immunomodulatory molecules, such as cytokines; see below) are secreted by the microorganisms. Preferably, secretion of the allergens occurs inside a mammalian cell to reduce or eliminate exposure of allergens to a subject's allergic immune response. Secretion of polypeptides includes secretion into the extracellular medium and secretion of polypeptides into the periplasm of microorganisms such as gram-negative bacteria and yeast. Advantages of secreting allergens into the periplasm include reducing leakage of the allergens prior to phagocytosis of the microorganism. This advantage is most applicable in non-inducible systems. Advantages of secreting allergens into the extracellular medium in inducible systems include maximizing the amount of allergens available for processing by antigen-presenting cells after phagocytosis of the microorganisms of the present invention.

To express secreted polypeptides in bacteria, a variety of bacterial secretion signals known in the art may be used. For example, the Sec-dependent process in *E. coli* is one which is well known (for a review see Driessen et al. *Curr. Opin. Microbiology* 1:216-22). In addition, the OmpA signal peptide in *E. coli* has been described by Wong and Sutherland (U.S. Pat. No. 5,223,407). Fusion proteins containing either of these secretion signal peptides are not fully secreted by the bacteria, but rather transported across the inner membrane of the gram-negative bacteria into the periplasm. These secretion signals may be used in the present invention to transport allergenic or immunomodulatory polypeptides into the periplasm of bacteria. After administration of the genetically engineered bacteria to an individual and subsequent phagocytosis by APCs, the allergenic or immunomodulatory polypeptides in the periplasm are released after degradation of the outer membrane by enzymes in the endosome of the APCs. Preferably, the bacteria synthesize and secrete the polypeptides into the periplasm and are killed, preferably heat-killed, before administration. However, it is recognized that attenuated bacteria may be used to secrete inventive allergens into the periplasm and administered to individuals.

In another preferred embodiment of secreted proteins or polypeptides, fusion proteins containing secretion signal sequences and allergenic or immunomodulatory sequences are fully secreted into the extracellular medium by a microorganism after synthesis of the protein. Such secretion signals include those found in hemolysin and listeriolysin. In a particularly preferred embodiment, the hemolysin complex of *E. coli* is used to transport allergenic or immunomodulatory polypeptides across the inner and outer membrane of a microorganism (e.g. *E. coli, Salmonella, Shigella, Vibrio, Yersinia, Citrobacter, Serratia, Pseudomonas*) into the extracellular medium (Spreng et al. *Mol. Microbiol.* 31:1589-1601, 1999, and references therein all of which are incorporated herein by reference). Fusion of HlyAs to proteins and polypeptides has been shown to result in secretion of these fusion proteins utilizing the hemolysin secretion system (Blight and Holland, *Trends Biotechnol.* 1994 November; 12(11):450-5; Gentschev et al., *Behring Inst Mitt.* 1994 December; (95):57-66)

The hemolysin protein (HlyA) contains a C-terminal transport signal (HlyAs) which is approximately 50-60 amino acids in length (Hess et al., *Mol Gen Genet.* 1990 November; 224(2):201-8; Jarchau et al., *Mol Gen Genet.* 1994 Oct. 17; 245(1):53-60). The HlyA protein is secreted across the inner and outer cellular membranes by the hemolysin secretion system. This complex contains three membrane proteins. Two of these proteins, HlyB and HlyD, are located in the inner membrane, and the third TolC, is located at the outer membrane. Genes encoding these proteins are part of the hemolysin operon which consists of four genes hlyC, hlyA, hlyB, and hlyD (Wagner et al., *J Bacteriol.* 1983 April; 154(1):200-10; Gentschev. *Gene.* 1996 Nov. 7; 179(1):133-40).

In a preferred embodiment for use of the Hly secretion system, DNA plasmids (vectors) are used to express fusion proteins containing the HlyAs signal peptide and allergenic or immunomodulatory polypeptides. The genes encoding the transport complex (hlyB, and hlyD) are encoded by the same vector. It is recognized that multiple vectors can be used to encode and express these genes, or that sequences encoding these genes can be inserted into the host genome for expression. Preferably, a single vector contains the complete hemolysin operon including the hly specific promoter and an enhancer-type regulator hlyR; the HlyA gene where only the minimal polypeptide sequence necessary to transport a fusion protein is present; and the antigen of interest. TolC protein is generally produced by the host *E. coli* system. However, in systems where tolC DNA is not encoded by a host organism, tolC can be encoded by a vector.

In a particularly preferred embodiment, the secretion plasmid pMOhly1 described in WO 98/50067 ("Donner") is used to express fusion proteins containing secretion signal sequences and polypeptides related to inducing anaphylaxis in individuals. The secretion vector pMOhly1 contains the complete hemolysin operon including the hly specific promoter and an enhancer-type regulator hlyR. A majority of the hlyA gene has been deleted so that HlyA encodes only the 34 amino terminal and 61 carboxyl terminal amino acids (HlyA$_s$). A unique Nsi restriction enzyme site between the amino terminal and carboxyl terminal residues of HlyA facilitates the insertion of heterologous genes or gene fragments into the reading frame of HlyA$_s$. The genetic information for antigens the size of 10-1000 amino acids can be inserted into this secretion vector pMOhly1, which facilitates the secretion of these antigens in attenuated *Salmonella* and other gram-negative attenuated inoculation strains (e.g. *E. coli, Vibrio cholera, Yersina enterocolitica*). In contrast to other secretion systems, the secretion of fusion proteins using a single plasmid is described by Donner. An advantage of the hemolysin secretion system in comparison to conventional transport systems is the larger size of the fusion proteins synthesized and secreted according to the methods taught in Donner. Conventional secretion systems for the presentation of antigens are only capable of secreting relatively short peptides to the outer part of the bacterial cell (Cardenas and Clements, *Clin Microbiol Rev.* 1992 July; 5(3):328-42).

Antigens and Allergens

In general, any allergen may be produced by microorganisms in accordance with the present invention. Preferred allergens are found in certain foods, venom, drugs or rubber and are capable of eliciting allergic responses, and in particular anaphylactic allergic responses in an individual. Particularly preferred allergens are protein or polypeptide allergens.

In a preferred embodiment, microorganisms of the present invention produce allergenic proteins that elicit allergies, possibly anaphylaxis, and are found in foods, venoms, drugs, and rubber-based products. Particularly preferred allergenic proteins that induce anaphylaxis, such as several protein allergens found in food (peanut, milk, egg, wheat), insect venom (i.e. bees, reptiles), drugs, and latex. Non-limiting examples of protein allergens found in food include proteins found in nuts (e.g., peanut walnut, almond, pecan, cashew, hazelnut, pistachio, pine nut, brazil nut), seafood (e.g. shrimp, crab, lobster, clams), fruit (e.g. plums, peaches, nectarines; *Ann Allergy Asthma Immunol* 7(6):504-8 (1996); cherries, *Allergy* 51(10):756-7 (1996)), seeds (sesame, poppy, mustard), and soy and dairy products (e.g., egg, milk).

Some protein allergens found in nuts are related to legume allergies and may be used instead of the legume proteins (e.g. peanuts, soybeans, lentils; *Ann Allergy Asthma Immunol* 77(6): 480-2 (1996). Also, protein antigens found in pollen-related food allergies may be used (e.g. birch pollen related to apple allergies). Other protein allergens found in foods include those found in young garlic (*Allergy* 54(6):626-9 (1999), and for children allergic to house dust mites, allergens found in snails (*Arch Pediatr* 4(8):767-9 (1997)). Protein allergens in wheat are known to cause exercise-induced allergies (*J Allergy Clin Immunol* 1999 May; 103(5 Pt 1):912-7).

Stings from organisms that inject venoms, such as insect stings are known to cause anaphylaxis in individuals with allergies to the venom. In general, insect venom includes venom from Hymenoptera such as bees, hornets, wasps, yellow jackets, velvet ants, and fire ants. In particular for example, venom from honey bees of the genus *Apis* can cause anaphylaxis in stung victims who are allergic (Weber et al. *Allergy* 42:464-470). The venom from honey bees contains numerous compounds which have been extensively studied and characterized (see for a reference, Banks and Shipolini. *Chemistry and Pharmacology of Honey-bee Venom*. Chapter 7 of *Venoms of the Hymenoptera*. Ed. T. Piek. Academic Press. London. 1986). The two main components of bee venom are phospholipase A2 and melittin and are preferred protein allergens for use in the present invention for treating and preventing allergies to bee venom.

In certain uses of the present invention, it will be desirable to work in systems in which a single compound (e.g., a single protein) is responsible for most observed allergy. In other cases, the invention can be applied to more complex allergens. Therefore, collections of more than one antigen can be used so that immune responses to multiple antigens may be modulated simultaneously.

Appendix A presents a representative list of certain known protein antigens. As indicated, the amino acid sequence is known for many or all of these proteins, either through knowledge of the sequence of their cognate genes or through direct knowledge of protein sequence, or both. Of particular interest are anaphylactic antigens.

In another embodiment of allergenic antigens, microorganisms are genetically engineered to synthesize and secrete modified allergenic polypeptides that elicit anaphylaxis when exposed to individuals who are susceptible to anaphylactic shock. Preferably, the allergens are modified such that the ability to elicit anaphylaxis is reduced or eliminated. As previously discussed allergens elicit allergic responses which are sometimes severe enough to induce anaphylactic shock by crosslinking IgE antibodies bound to the surface of mast cells and basophils. The IgE crosslinking releases compounds such as histamines which causes symptoms related to allergies and anaphylactic shock. In accordance with the present invention, microorganisms are used to synthesize and secrete antigens which are modified to reduce or eliminate IgE binding sites while still maintaining antigenicity or immunomodulatory activity (U.S. Ser. No. 09/141,220 incorporated herein by reference). This reduces the risk of allergic or anaphylactic responses in individuals treated with vaccines containing these engineered microorganisms.

The amount of antigen to be employed in any particular composition or application will depend on the nature of the particular antigen and of the application for which it is being used, as will readily be appreciated by those of ordinary skill in the art. The experiments described in Examples 1-4 suggest that larger amounts of polypeptides are useful for inducing Th1 responses. The amount of antigen can be controlled by a variety of factors including but not limited to expression systems, inducible expression systems, levels of secretion and excretion, methods of killing bacteria before delivery. Those of ordinary skill in the art are capable of determining the desired levels of antigens to be produced by bacteria and delivered to individuals.

It is recognized that multiple antigenic molecules may be delivered by bacteria simultaneously in accordance with the methods of the present invention. Without limitation, different antigenic determinants for one antigenic protein may be delivered. Different antigenic determinants from different antigenic proteins may also be delivered. Further, multiple antigenic polypeptides and proteins may be delivered in accordance with the present invention. It is also recognized that single or multiple antigenic polypeptides and single or multiple cytokines may be delivered to individuals by bacteria in accordance with the present invention. For example but without limitation, allergenic antigens of the present invention and immunomodulatory molecules such as interleukins may be delivered by bacteria using secreted or non-secreted methods in accordance with the present invention.

Diagnostic and Therapeutic Reagents

The first step in making the modified allergen is to identify IgE binding sites and/or immunodominant IgE binding sites. The second step is to mutate one or more of the IgE binding sites, preferably including at a minimum one of the immunodominant sites, or to react the allergen with a compound that selectively blocks binding to one or more of the IgE binding sites. The third step is to make sufficient amounts of the modified allergen for administration to persons or animals in need of tolerance to the allergen, where the modified allergen is administered in a dosage and for a time to induce tolerance, or for diagnostic purposes. The modified allergen can be administered by injection, or in some cases, by ingestion or inhalation.

A. Allergens.

Many allergens are known that elicit allergic responses, which may range in severity from mildly irritating to life-threatening. Food allergies are mediated through the interaction of IgE to specific proteins contained within the food. Examples of common food allergens include proteins from peanuts, milk, grains such as wheat and barley, soybeans, eggs, fish, crustaceans, and mollusks. These account for greater than 90% of the food allergies (Taylor, Food Techn. 39, 146-152 (1992). The IgE binding epitopes from the major allergens of cow milk (Ball, et al. (1994) *Clin. Exp. Allergy*, 24, 758-764), egg (Cooke, S. K. and Sampson, H. R. (1997) *J. Immunol.*, 159, 2026-2032), codfish (Aas, K., and Elsayed, S. (1975) *Dev. Biol. Stand.* 29, 90-98), hazel nut (Elsayed, et al. (1989) *Int. Arch. Allergy Appl. Immunol.* 89, 410-415), peanut (Burks et al., (1997) *Eur. J. Biochemistry,* 245:334-339; Stanley et al., (1997) *Archives of Biochemistry and Biophysics,* 342:244-253), soybean (Herein, et al. (1990) *Int. Arch. Allergy Appl. Immunol.* 92, 193-198) and shrimp (Shanty, et al. (1993) *J. Immunol.* 151, 5354-5363) have all been elucidated, as have others Other allergens include proteins from insects such as flea, tick, mite, fire ant, cockroach, and bee as well as molds, dust, grasses, trees, weeds, and proteins from mammals including horses, dogs, cats, etc.

The majority of allergens discussed above elicit a reaction when ingested, inhaled, or injected. Allergens can also elicit a reaction based solely on contact with the skin. Latex is a well known example. Latex products are manufactured from a milky fluid derived from the rubber tree, *Hevea brasiliensis* and other processing chemicals. A number of the proteins in latex can cause a range of allergic reactions. Many products contain latex, such as medical supplies and personal protective equipment. Three types of reactions can occur in persons sensitive to latex: irritant contact dermatitis, and immediate systemic hypersensitivity. Additionally, the proteins responsible for the allergic reactions can fasten to the powder of latex gloves This powder can be inhaled, causing exposure through the lungs. Proteins found in latex that interact with IgE antibodies were characterized by two-dimensional electrophoresis. Protein fractions of 56, 45, 30, 20, −14, and less than 6.5 kd were detected (Posch A. et al., (1997) *J. Allergy Clin. Immunol.* 99(3), 385-395). Acidic proteins in the 8-14 kd and 22-24 kd range that reacted with IgE antibodies were also identified (Posch A. et al., (1997) *J. Allergy Clin. Immunol.* 99(3), 385-395. The proteins prohevein and hevein, from *hevea brasiliensis*, are known to be major latex allergens and to interact with IgE (Alenius, H., et al., *Clin. Exp. Allergy* 25(7), 659-665; Chen Z., et al., (1997). *J. Allergy Clin. Immunol.* 99(3), 402-409). Most of the IgE binding domains have been shown to be in the hevein domain rather than the domain specific for prohevein (Chen Z., et al., (1997) *J. Allergy Clin. Immunol.* 99(3), 402-409). The main IgE-binding epitope of prohevein is thought to be in the N-terminal, 43 amino acid fragment (Alenius H., et al., (1996) *J. Immunol.* 156(4), 1618-1625). The hevein lectin family of proteins has been shown to have homology with potato lectin and snake venom disintegrins (platelet aggregation inhibitors) (Kielisqewski, M. L., et al., (1994) *Plant J.* 5(6), 849-861).

B. Identification of IgE Binding Sites.

Allergens typically have both IgE and IgG binding sites and are recognized by T cells. The binding sites can be determined either by using phage display libraries to identify conformational epitopes (Eichler and Houghten, (1995) *Molecular Medicine Today* 1, 174-180; Jensen-Jarolim et al., (1997) *J. Appl. Clin. Immunol.* 101, 5153a) or by using defined peptides derived from the known amino acid sequence of an allergen (see examples below), or by binding of whole protein or protein fragments to antibodies, typically antibodies obtained from a pooled patient population known to be allergic to the allergen. It is desirable to modify allergens to diminish binding to IgE while retaining their ability to activate T cells and in some embodiments by not significantly altering or decreasing IgG binding capacity. This requires modification of one or more IgE binding sites in the allergen.

A preferred modified allergen is one that can be used with a majority of patients having a particular allergy. Use of pooled sera from allergic patients allows determination of one or more immunodominant epitopes in the allergen. Once some or all of the IgE binding sites are known, it is possible to modify the gene encoding the allergen, using site directed mutagenesis by any of a number of techniques, to produce a modified allergen as described below, and thereby express modified allergens. It is also possible to react the allergen with a compound that achieves the same result as the selective mutation, by making the IgE binding sites inaccessible, but not preventing the modified allergen from activating T cells, and, in some embodiments, by not significantly altering or decreasing IgG binding.

Assays to assess an immunologic change after the administration of the modified allergen are known to those skilled in the art. Conventional assays include RAST (Sampson and Albergo, 1984), ELISAs (Burks, et al. 1986) immunoblotting (Burks, et al. 1988), and in vivo skin tests (Sampson and Albergo 1984). Objective clinical symptoms can be monitored before and after the administration of the modified allergen to determine any change in the clinical symptoms.

It may be of value to identify IgEs which interact with conformational rather than linear epitopes. Due to the complexity and heterogeneity of patient serum, it may be difficult to employ a standard immobilized allergen affinity-based approach to directly isolate these IgEs in quantities sufficient to permit their characterization. These problems can be avoided by isolating some or all of the IgEs which interact with conformational epitopes from a combinatorial IgE phage display library.

Steinberger et al. (Steinberger, P., Kraft D. and Valenta R. (1996) "Construction of a combinatorial IgE library from an allergic patient: Isolation and characterization of human IgE Fabs with specificity for the major Timothy Grass pollen antigen," Phl p. 5 *J. Biol. Chem.* 271, 10967-10972) prepared a combinatorial IgE phage display library from mRNA isolated from the peripheral blood mononuclear cells of a grass allergic patient. Allergen-specific IgEs were selected by panning filamentous phage expressing IgE Fabs on their surfaces against allergen immobilized on the wells of 96 well microtiter plates. The cDNAs were than isolated from allergen-binding phage and transformed into *E. coli* for the production of large quantities of monoclonal, recombinant, allergen-specific IgE Fabs.

If native allergen or full length recombinant allergen is used in the panning step to isolate phage, then Fabs corresponding to IgEs specific for conformational epitopes should be included among the allergen-specific clones identified. By screening the individual recombinant IgE Fabs against denatured antigen or against the relevant linear epitopes identified for a given antigen, the subset of conformation-specific clones which do not bind to linear epitopes can be defined.

To determine whether the library screening has yielded a complete inventory of the allergen-specific IgEs present in patient serum, an immunocompetition assay can be performed. Pooled recombinant Fabs would be preincubated with immobilized allergen. After washing to remove unbound Fab, the immobilized allergen would then be incubated with patient serum. After washing to remove unbound serum proteins, an incubation with a reporter-coupled secondary antibody specific for IgE Fc domain would be performed. Detection of bound reporter would allow quantitation of the extent to which serum IgE was prevented from binding to allergen by recombinant Fab. Maximal, uncompeted serum IgE binding would be determined using allergen which had not been preincubated with Fab or had been incubated with nonsense Fab. If IgE binding persists in the face of competition from the complete set of allergen-specific IgE Fab clones, this experiment can be repeated using denatured antigen to determine whether the epitopes not represented among the cloned Fabs are linear or conformational.

Production of Recombinant or Modified Allergens

A modified allergen will typically be made using recombinant techniques. Expression in a procaryotic or eucaryotic host including bacteria, yeast, and baculovirus-insect cell systems are typically used to produce large (mg) quantities of the modified allergen. It is also possible to make the allergen synthetically, if the allergen is not too large, for example, less than about 25-40 amino acids in length.

Adjuvants and Immunostimulatory Agents

Compositions and methods of the present invention include the use of adjuvants and immunomodulatory polypeptides or immunostimulatory factors to modulate an individual's immune response. Immunologic adjuvants are agents that enhance specific immune responses to vaccines. Formulation of vaccines with potent adjuvants is desirable for improving the performance of vaccines composed of antigens. Adjuvants may have diverse mechanisms of action and should be selected for use based on the route of administration and the type of immune response (antibody, cell-mediated, or mucosal immunity) that is desired for a particular vaccine In general, immunomodulatory polypeptides include cytokines which are small proteins or biological factors (in the range of 5-20 kD) that are released by cells and have specific effects on cell-cell interaction, communication and behavior of other cells. As previously described, cytokines in accordance with the present invention are proteins that are secreted to T-cells to induce a Th1 or Th2 response. Preferably, the cytokine(s) to be administered is/are selected to reduce production of a Th2 response to antigens associated with anaphylaxis. One preferred method of reducing a Th2 response is through induction of the alternative response. Cytokines that, when expressed during antigen delivery into cells, induce a Th1 response in T cells (i.e., "Th1 stimulating cytokines") include IL-12, IL-2, I-18, IL-1 or fragments thereof, IFN, and/or IFNγ.

Other compounds that are immunomodulatory include immunological inducing agents. These inducing agents prompt the expression of Th1 stimulating cytokines by T-cells and include factors such as, CD40, CD40 ligand, oligonucleotides containing CpG motifs, TNF, and microbial extracts such as preparations of *Staphylococcus aureus*, heat killed *Listeria*, and modified cholera toxin, etc.

Those of ordinary skill in the art readily appreciate the preferred types of adjuvants for use with particular antigen compositions. In general, immunologic adjuvant include gel-type adjuvants (e.g. aluminum hydroxide/aluminum phosphate, calcium phosphate), microbial adjuvants (e.g. DNA such as CpG motifs; endotoxin such as monophosphoryl lipid A; exotoxins such as cholera toxin, *E. coli* heat labile toxin, and pertussis toxin; and muramyl dipeptide), oil-emulsion and emulsifier-based adjuvants (e.g. Freund's Incomplete Adjuvant, MF59, and SAF), particulate adjuvants (e.g. liposomes, biodegradable microspheres, and saponins), and synthetic adjuvants (e.g. nonionic block copolymers, muramyl peptide analogues, polyphosphazene, and synthetic polynucleotides).

Adjuvants that are known to stimulate Th2 responses are preferably avoided. Particularly preferred adjuvants include, for example, preparations (including heat-killed samples, extracts, partially purified isolates, or any other preparation of a microorganism or macroorganism component sufficient to display adjuvant activity) of microorganisms such as *Listeria monocytogenes* or others (e.g., Bacille Calmette-Guerin [BCG], *Corynebacterium* species, *Mycobacterium* species, *Rhodococcus* species, *Eubacteria* species, *Bortadella* species, and *Nocardia* species), and preparations of nucleic acids that include unmethylated CpG motifs (see, for example, U.S.

Pat. No. 5,830,877; and published PCT applications WO 96/02555, WO 98/18810, WO 98/16247, and WO 98/40100, each of which is incorporated herein by reference). Other preferred adjuvants reported to induce Th1-type responses and not Th2-type responses include, for example, Aviridine (N,N-dioctadecyl-N'N'-bis(2-hydroxyethyl)propanediamine) and CRL 1005. Particularly preferred are ones that induce IL-12 production, including microbial extracts such as fixed *Staphylococcus aureus, Streptococcal preparations, Mycobacterium tuberculosis*, lipopolysaccharide (LPS), monophosphoryl lipid A (MPLA) from gram negative bacterial lipopolysaccharides (Richards et al. *Infect Immun* 1998 June; 66(6):2859-65), *listeria monocytogenes, toxoplasma gondii, leishmania major*. Some polymers are also adjuvants. For example, polyphosphazenes are described in U.S. Pat. No. 5,500,161 to Andriavnov, et al. These can be used not only to encapsulate the microorganisms but also to enhance the immune response to the antigen.

If adjuvants are not synthesized by microorganisms in accordance with the present invention, adjuvants which are cytokines may be provided as impure preparations (e.g., isolates of cells expressing a cytokine gene, either endogenous or exogenous to the cell), but are preferably provided in purified form. Purified preparations are preferably at least about 90% pure, more preferably at least about 95% pure, and most preferably at least about 99% pure. Alternatively, genes encoding the cytokines or immunological inducing agents may be provided, so that gene expression results in cytokine or immunological inducing agent production either in the individual being treated or in another expression system (e.g., an in vitro transcription/translation system or a host cell) from which expressed cytokine or immunological inducing agent can be obtained for administration to the individual. It is recognized that microorganisms utilized to synthesize and deliver allergenic and/or immunomodulatory proteins according to the present invention can act as an adjuvant, and that preferred microorganisms are immunostimulatory adjuvants.

It will be appreciated by those of ordinary skill in the art that the inventive administration of microorganisms expressing cytokines and/or allergens may optionally be combined with the administration of any other desired immune system modulatory factor such as, for example, an adjuvant or other immunomodulatory compound.

Methods of Administration

Formulations can be delivered to a patient by any available route including for example enteral, parenteral, topical (including nasal, pulmonary or other mucosal route), oral or local administration. The compositions are preferably administered in an amount effective to elicit cellular immunity and production of Th1-related IgG while minimizing IgE mediated responses. Also preferred are compositions administered in an effective amount to active T-cell response, preferably Th1-type responses. For compositions of the present invention containing bacteria, administration is preferably delivered parenterally.

It is important to administer the modified allergen to an individual (human or animal) to decrease the clinical symptoms of allergic disease by using a method, dosage, and carrier which are effective. Allergen will typically be administered in an appropriate carrier, such as saline or a phosphate saline buffer. Allergen can be administered by injection subcutaneously, intramuscularly, or intraperitoneally (most humans would be treated by subcutaneous injection), by aerosol, inhaled powder, or by ingestion.

Pharmaceutical Compositions

Pharmaceutical compositions for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and/or to other animals, orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include agents such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of an agent, it is often desirable to slow the absorption of the drug from subcutaneous or intramuscular injection. This may be accomplished by the use of a liquid suspension of crystalline or amorphous material with poor water solubility. The rate of absorption of the agent then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of agent to polymer and the nature of the particular polymer employed, the rate of release of the agent can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The compounds can also be in micro-encapsulated form with one or more excipients as noted above. The solid dosage forms of tablets, dragees, capsules, pills and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of an inventive pharmaceutical composition include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye drops are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Encapsulation

In a preferred embodiment, inventive compositions comprising live microorganisms are provided in association with an encapsulation device (see, for example, U.S. Ser. No. 60/169,330 entitled "Controlled Delivery of Antigens" filed Dec. 6, 1999, incorporated by reference herewith). Preferred encapsulation devices are biocompatible, are stable inside the body so that microorganisms are not released until after the encapsulation device reaches its intended destination (e.g. mucosal lining of the gut, endocytosis by antigen-presenting cells (APC)). For example, preferred systems of encapsulation are stable at physiological pH and degrade at acidic pH levels comparable to those found in the digestive tract or endosomes of APCs. Particularly preferred encapsulation compositions include but are not limited to ones containing liposomes, polylactide-co-glycolide (PLGA), chitosan, synthetic biodegradable polymers, environmentally responsive hydrogels, and gelatin PLGA nanoparticles. Inventive compositions may be encapsulated in combination with one or more adjuvants, targeting entities, or other agents including, for example, pharmaceutical carriers, diluents, excipients, oils, etc. Alternatively or additionally the encapsulation device itself may be associated with a targeting entity and/or an adjuvant.

Methods of encapsulating live cells are known and may also be used in accordance with the present invention for delivering antigen-secreting microorganisms to individuals. The following references are provided as examples of encapsulation of live cells. However, any method of encapsulating live cells may be used in the present invention. U.S. Pat. Nos. 5,084,350; 4,680,174; and 4,352,883 (all of which are incorporated herein by reference) describe the encapsulation of a prokaryotic or eukaryotic cell or cell culture in microcapsules. Briefly, U.S. Pat. Nos. 5,084,350; 4,680,174; and 4,352,883 disclose that a tissue sample, cell, or cell culture to be encapsulated is first prepared in finely divided form in accordance with well-known techniques and suspended in an aqueous medium suitable for maintenance and for supporting the ongoing metabolic processes of the particular cells involved. Media suitable for this purpose generally are available commercially. Thereafter, a water-soluble substance which is physiologically compatible with the cells and which can be rendered water-insoluble to form a shape-retaining coherent spheroidal mass or other shape is added to the medium. The solution is then formed into droplets containing cells together with their maintenance or growth medium and is immediately rendered water-insoluble and gelled to form shape-retaining, typically spheroidal coherent masses.

The material used to induce gelation of the culture medium may be any non-toxic water-soluble material which, by a change in the surrounding temperature, pH, ionic environment, or concentration, can be converted to shape-retaining masses. Preferably, the material also is one which comprises plural, easily ionized groups, e.g., carboxyl or amino groups, which can react by salt formation with polymers containing plural groups which ionize to form species of the opposite charge. Use of this type of material enables the deposition of a membrane of a selected porosity range without damage to the labile cells. The presently preferred materials for forming the gelled masses are water-soluble natural or synthetic polysaccharides. Many such commercially available materials are typically extracted from vegetable matter and are often used as additives in various foods. Sodium alginate is the presently preferred water-soluble polysaccharide. Other usable materials include acidic fractions of guar gum, gum arabic, carrageenan, pectin, tragacanth gum or xanthan gums. These materials may be gelled when multivalent ions are exchanged for the acidic hydrogen or alkali metal ion normally associated with the carboxyl groups.

Uses

The compositions of the present invention may be employed to treat or prevent allergic reactions in a subject. Subjects are animal and human patients in need of treatment for allergies. Preferably, the animal is a domesticated mammal (e.g., a dog, a cat, a horse, a sheep, a pig, a goat, a cow, etc). Animals also include laboratory animals such as mice, rats, hamsters, monkeys, and rabbits. Any individual who suffers from allergy, or who is susceptible to allergy, may be treated. It will be appreciated that an individual can be considered susceptible to allergy without having suffered an allergic reaction to the particular antigen in question. For example, if the individual has suffered an allergic reaction to a related antigen (e.g., one from the same source or one for which shared allergies are common), that individual will be considered susceptible to allergy to the relevant antigen. Similarly, if members of an individual's family are allergic to a particular antigen, the individual may be considered to be susceptible to allergy to that antigen. More preferably, any individual who is susceptible to anaphylactic shock upon exposure to food allergens, venom allergens or rubber allergens may be treated according to the present invention.

The compositions of the present invention may be formulated for delivery by any route. Preferably, the compositions are formulated for injection, ingestion, or inhalation.

Therapy or desensitization with the modified allergens can be used in combination with other therapies, such as allergen-non-specific anti-IgE antibodies to deplete the patient of allergen-specific IgE antibodies (Boulet, et al. (1997) 155: 1835-1840; Fahy, et al. (1997) *American J Respir. Crit. Care Med.* 155:1828-1834; Demoly, P. and Bousquet (1997) *J Am J Resp. Crit. Care Med.* 155:1825-1827), or by the pan specific anti-allergy therapy described in U.S. Ser. No. 08/090, 375 filed Jun. 4, 1998, by M. Caplan and H. Sosin. Therapy with the modified allergen can also be administered in combination with an adjuvant such as IL-12, IL-16, IL-18, IFNγ.

The nucleotide molecule encoding the modified allergen can also be administered directly to the patient, for example, in a suitable expression vector such as a plasmid, which is injected directly into the muscle or dermis, or through administration of genetically engineered cells.

In general, effective dosages will be in the picogram to milligram range, more typically microgram to milligram. Treatment will typically be between twice/weekly and once a month, continuing for up to three to five years, although this is highly dependent on the individual patient response.

The modified allergen can also be used as a diagnostic to characterize the patient's allergies, using techniques such as those described in the examples.

Modifications and variations of the methods and compositions described herein are intended to be within the scope of the following claims.

OTHER EMBODIMENTS

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

EXAMPLES

Material and Methods

For general methods used to express proteins in microorganisms see Ausubel et al. (supra) and Sambrook et al. (supra) both of which are incorporated herein by reference. In addition, expression vectors for use in the present invention are widely available from commercial sources (see for example, Clontech, Palo Alto, Calif.; Invitrogen, Carlsbad, Calif.; Promega Corporation, Madison, Wis.; New England Biolabs, Beverly, Mass.).

The following experiments describe the encapsulation of allergens in bacteria for use as a delivery vehicle and/or adjuvant in immunotherapy in accordance with the teachings of the present invention. Recombinant peanut allergen proteins (Ara h 1, Ara h 2, and Ara h 3; Burks et al. *J Allergy Clin Immunol.* 88(2):172-9, 1991; Burks et al. *J Allergy Clin Immunol.* 90(6 Pt 1):962-9, 1992; Rabjohn et al. *J Clin Invest.* 103(4):535-42, 1999; incorporated herein by reference) were produced in *E. coli* BL21 cells by transforming the bacterial cells with cDNA clones encoding the proteins (see Appendix B; sequences cloned into pET24, Novagen, Madison, Wis.). The transformed cells were then injected into C3H/HEJ mice to determine if the allergen-expressing *E. coli* elicited an immune response.

Example 1

Methods of Killing Allergen-producing *E. Coli*

Several methods of killing allergen-producing *E. coli* were tested. Preferably, the method of killing bacteria does not denature or proteolyze the recombinant allergen(s) produced by the bacteria. As non-limiting examples, *E. coli* were killed by heat (at temperatures ranging from 37° C. to 95° C.), by using ethanol (0.1% to 10%), and by using solutions containing iodine (0.1% to 10%). Survival was determined by plating 100 µl of cells onto the appropriate agar plates, and subsequently counting the resulting colonies. The most reproducible method was heat killing. Therefore, the preferred method of killing allergen-producing *E. coli* is to incubate the cells at 60° C. for 20 minutes which results in 100% death (i.e. no colonies formed; see FIG. 1).

Example 2

Growth of Bacteria

The following protocol was developed for the preparation of allergen-producing *E. coli* cells for inoculation of mice.
Day 1
Five milliliters (ml) of liquid cultures of LB (Luria-Bertani broth) containing kanamycin (30 micrograms/ml per each cell line used) were prepared in 50 ml sterile tubes or flasks. Cultures were inoculated with approximately 10 microliters from a frozen stock of the desired bacterial cell line containing the desired expression vectors. The inoculated cultures were incubated with shaking overnight at 37° C.
Day 2
The following morning, 100 ml of liquid LB (500 ml Erlenmeyer flask) containing kanamycin (30 micrograms/ml) were inoculated using a 1 ml aliquot from the 5 ml culture grown from the previous day. (The remaining 4 mls of culture were frozen. Optionally, the remaining 4 milliliters of culture can be stored at 4° C. for several weeks for inoculating subsequent cultures) The inoculated cultures were incubate with shaking at 37° C. until the optical density of the solution measured at 600 nM ($OD_{600}$) reached approximately 0.6 to 0.9.
Day 3
To induce production of recombinant proteins, the cultures from the previous day were induced by adding isopropyl-beta-D-thiogalactopyranoside (IPTG; Sigma-Aldrich, St. Louis, Mo.) from a 1 M stock to a final concentration of 1 mM (100 microliters of 1 M IPTG per 100 mls of culture) when the $OD_{600}$ of the culture reached approximately 0.6-0.9. The induced cultures were incubated overnight.
Day 4
1.4 ml of culture from the previous day were aliquoted into each of five 1.5 ml microfuge tubes for each culture and heat killed at 60° C. in a water bath for 20 minutes. The tubes were centrifuged at 16,000×g for 5 minutes at room temperature and the supernatant discarded. The pellets were washed with 1× phosphate buffer saline (PBS) and centrifuged at 16,000×g for 5 minutes at room temperature. Again, the supernatant was discarded and the pellets were resuspended in 250 microliters of 1×PBS. The resuspended pellets from the same original samples were combined. The $OD_{600}$ were determined for each sample and diluted to the desired $OD_{600}$ using 1×PBS.

Example 3

Production and Release of Allergen

Figure 2:
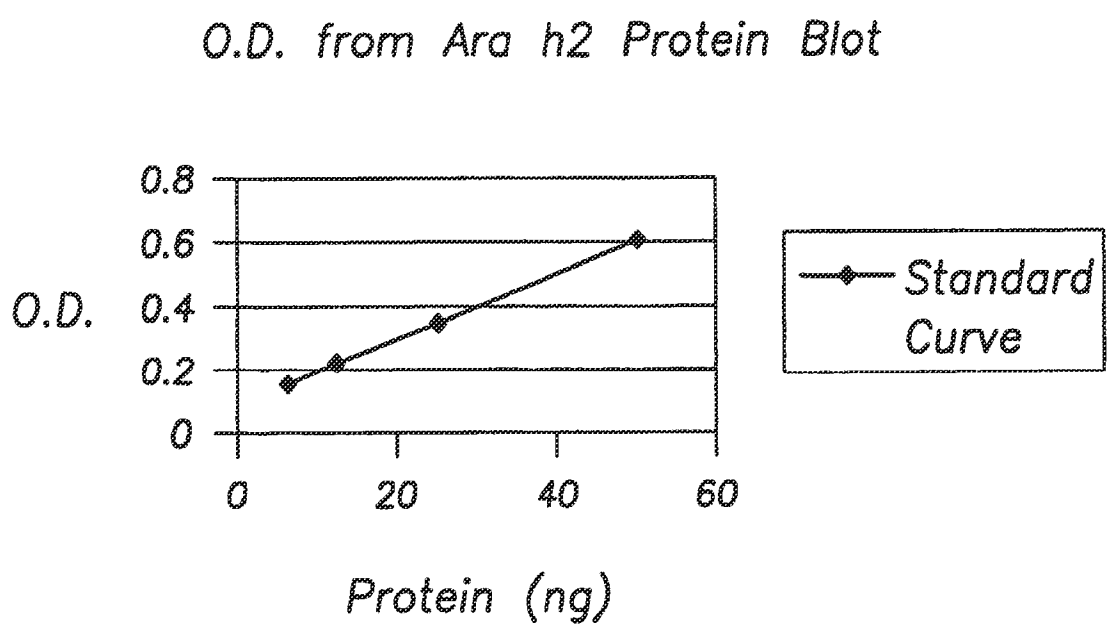

Release of Allergen by Heat-killed Bacteria
In order to determine if the cells remained intact after heat-killing we measured the amount of allergen released into the media. A dot-blot assay was developed that utilized as controls, purified recombinant allergens applied to a filter at known concentrations and serum IgE from peanut sensitive patients. The assay detected and quantified the amount of allergen present in 100 microliters of supernatant after pelleting heat-killed bacteria. The level of allergen released varied and was dependent on the expression vector and protein tested. In general, more Ara h 2 was released than Ara h 1 and Ara h 3 (Ara h 2>>Ara h 1>Ara h 3).
Production of Allergen.
In order to measure amounts of allergen in *E. coli*, we developed an immunoblot assay that utilizes a six histidine tag (HIS tag) that is present on all of our purified recombinant allergens and a HIS tag antibody to build a standard curve that could then be used to estimate amounts of allergen produced. The amount of allergen produced on a per cell basis varied depending on which clone was tested. In general, more Ara h 3 was produced than Ara h 2 and Ara h 1 (Ara h 3>Ara h 2>>Ara h1).
Our best estimates for amounts of allergen delivered in 100 µl of a 2.0 O.D. inoculum of *E. coli* varies from about 1 µg of Ara h 1 to about 20 µg of Ara h 3.
FIG. 2 is an example of a standard curve generated for Ara h 2. The optical density (O.D.) of the HIS-tagged Ara h 2 allergen is then determined from an immunoblot where different concentrations of *E. coli* extract has been electrophoresed on SDS-PAGE gels. The allergen O.D. is then used to estimate the amount of protein produced by that extract.

Example 4

Immune Response of Mice

The following protocol was utilized to determine the immune response of mice injected with allergen-producing bacteria. Blood was collected from the tail vein of each mouse used before the first injection. Enough blood was collected for antibody ELISA for each allergen and *E. coli* proteins. On Day Zero each mouse was injected with 100 microliters of the killed *E. coli* samples subcutaneously in the left hind flank. The mice were injected for the second time on Day 14 using the same procedure as Day Zero. On Day 21, a second blood sample was collected from each mouse. Blood samples at Day 0 and Day 21 were assayed for IgG1 and IgG2a antibodies to either Ara h 1, Ara h 2, or Ara h 3 by an ELISA assay.
Mice injected with *E. coli* producing Ara h 1 did not give detectable levels of any immunoglobulin to the Ara h 1 allergen and therefore, that data are not shown. Without limitation to theory, we speculate that this may be due to the relatively small amounts of Ara h 1 produced by these cells (see previous discussion). Mice injected with *E. coli* producing Ara h 2 contained relatively high levels of IgG1 and IgG2a. Again, without limitation to the cause, we speculated that this may be due to the amount of Ara h 2 released from these cells (see discussion above). Mice injected with *E. coli* producing Ara h 3 contained relatively high levels of IgG2a (indicative of a Th1-type response) and elicited relatively low levels of IgG1 (indicative of a Th2-type response.
Interpretation of Results
The present data should be cautiously interpreted. The data in the Figures only represent O.D. levels and do not represent absolute amounts of immunoglobulin. Therefore comparisons between groups should take into consideration the data presented as O.D. However, the general trend suggests that for example, more mice exhibited an IgG2a response to Ara h 3 than mice that exhibit an IgG1 response to Ara h 3.

Examples 5-9

Peanut allergy is one of the most common and serious of the immediate hypersensitivity reactions to foods in terms of persistence and severity of reaction. Unlike the clinical symptoms of many other food allergies, the reactions to peanuts are rarely outgrown, therefore, most diagnosed children will have the disease for a lifetime (Sampson, H. A., and Burks, A. W. (1996) *Annu. Rev. Nutr.* 16, 161-77; Bock, S. A. (1985). *J. Pediatr.* 107, 676-680). The majority of cases of fatal food-induced anaphylaxis involve ingestion of peanuts (Sampson et al., (1992) *NEJM* 327, 380-384; Kaminogawa, S. (1996) *Biosci. Biotech. Biochem.* 60, 1749-1756). The only effective therapeutic option currently available for the prevention of a peanut hypersensitivity reaction is food avoidance. Unfortunately, for a ubiquitous food such as a peanut, the possibility of an inadvertent ingestion is great.

The examples described below demonstrate identification, modification, and assessment of allergenicity of the major peanut allergens, Ara h 1, Ara h 2, and Ara h 3. Detailed experimental procedures are included for Example 1. These same procedures were used for Examples 2-5. The nucleotide sequences of Ara h 1, Ara h 2, and Ara h 3, are shown in SEQ ID NOs. 1, 3, and 5, respectively. The amino acid sequences of Ara h 1, Ara h 2, and Ara h 3 are shown in SEQ ID NOs. 2, 4, and 6 respectively.

Example 5

Identification of Linear IgE Binding Epitopes

Due to the significance of the allergic reaction and the widening use of peanuts as protein extenders in processed foods, there is increasing interest in defining the allergenic proteins and exploring ways to decrease the risk to the peanut-sensitive individual. Various studies over the last several years have identified the major allergens in peanuts as belonging to different families of seed storage proteins (Burks, et al. (1997) *Eur. J. Biochem.* 245, 334-339; Stanley, et al. (1997) *Arch. Biochem. Biophys.* 342, 244-253). The major peanut allergens Ara h 1, Ara h 2, and Ara h 3 belong to the vicilin, conglutin and glycinin families of seed storage proteins, respectively. These allergens are abundant proteins found in peanuts and are recognized by serum IgE from greater than 95% of peanut sensitive individuals, indicating that they are the major allergens involved in the clinical etiology of this disease (Burks, et al. (1995). *J. Clinical Invest.,* 96, 1715-1721). The genes encoding Ara h 1 (SEQ ID NO. 1), Ara h 2 (SEQ ID NO. 3), and Ara h 3 (SEQ ID NO. 5) and the proteins encoded by these genes (SEQ ID NOs. 2, 4, 6) have been isolated and characterized. The following studies were conducted to identify the IgE epitopes of these allergens recognized by a population of peanut hypersensitive patients and a means for modifying their affinity for IgE.

Experimental Procedures

Serum IgE. Serum from 15 patients with documented peanut hypersensitivity reactions (mean age, 25 yrs) was used to determine relative binding affinities between wild-type and mutant Ara h 1 synthesized epitopes. The patients had either a positive double-blind, placebo-controlled, food challenge or a convincing history of peanut anaphylaxis (laryngeal edema, severe wheezing, and/or hypotension; Burks, et al. (1988) *J. Pediatr.* 113, 447-451). At least 5 ml of venous blood was drawn from each patient, allowed to clot, and serum was collected A serum pool from 12 to 15 patients was made by mixing equal aliquots of serum IgE from each patient. The pools were then used in immunoblot analysis.

Peptide Synthesis. Individual peptides were synthesized on a derivatized cellulose membrane using 9-fluorenyll-methoxycarbonyl (Fmoc) amino acid active esters according to the manufacturer's instructions (Geriosys Biotechnologies, Woodlands, Tex.; Fields, G. B and Noble, R. L. (1990) *Int. J. Peptide Protein Res.* 35, 161-214). Fmoc-amino acids (N-terminal blocked) with protected side chains were coupled in the presence of 1-methyl-2-pyrrolidone to a derivatized cellulose membrane. Following washing with dimethylformamide (DMF), unreacted terminal amino groups were blocked from further reactions by acetylation with acetic anhydride. The N-terminal Fmoc blocking group was then removed by reaction with 20% piperidine and 80% DMF, v/v. The membrane was washed in DMF followed by methanol, the next reactive Fmoc-amino acid was then coupled as before, and the sequence of reactions was repeated with the next amino acid. When peptide synthesis was complete, the side chains were deprotected with a mixture of dichloromethane (DCM), trifluoroacetic acid, and triisobutylsilane (1.0:1.0:0.5), followed by successive washes in DCM, DMF, and methanol. Peptides synthesis reactions were monitored by bromophenol blue color reactions during certain steps of synthesis. Cellulose derivitised membranes and Fmoc-amino acids were supplied by Genosys Biotechnologies. All other chemical were purchased from Aldrich Chemical Company, Inc. (Milwaukee, Wis.) or Fluka (Bucks, Switzerland). Membranes were either probed immediately or stored at −20° C. until needed.

IgE Binding Assays. Cellulose membranes containing synthesized peptides were washed 3 times in Tris-buffered saline (TBS; 136 mM NaCl, 2.7 mM KCl, and 50 mM trizma base pH 8.0) for 10 min at room temperature (RT) and then incubated overnight in blocking buffer: [TBS, 0.05% Tween™ 20; concentrated membrane blocking buffer supplied by Genosys; and sucrose (0.0:1.0:0.5)]. The membrane was then incubated in pooled sera diluted in 1:5 in 20 mM Tris-Cl pH7.5, 150 mM NaCl, and 1% bovine serum albumin overnight at 4° C. Primary antibody was detected with $^{125}$I-labeled equine anti-human IgE (Kallestad, Chaska, Minn.).

Quantitation of IgE Binding. Relative amounts of IgE binding to individual peptides were determined by a Bio-Rad (Hercules, Calif.) model GS-700 imaging laser densitometer and quantitated with Bio-Rad molecular analyst software. A background area was scanned and subtracted from the obtained values. Following quantitation, wild-type intensities were normalized to a value of one and the mutants were calculated as percentages relative to the wild-type.

Synthesis and Purification of Recombinant Ara h 2 Protein. cDNA encoding Ara h 2 was placed in the pET-24b expression vector. The pET-24 expression vector places a 6× histidine tag at the carboxyl end of the inserted protein. The histidine tag allows the recombinant protein to be purified by affinity purification on a nickel column (HisBind resin). Recombinant Ara h 2 was expressed and purified according to the instructions of the pET system manual. Briefly, expression of the recombinant Ara h 2 was induced in 200 ml cultures of strain BL21(DE3) *E. coli* with 1 mM IPTG at mid log phase. Cultures were allowed to continue for an additional 3 hours at 36° C. Cells were harvested by centrifugation at 2000×g for 15 minutes and then lysed in denaturing binding buffer (6 M urea, 5 mM imidazole, 0.5 M NaCl, 20 mM Tris-HCl, pH 7.9). Lysates were cleared by centrifugation at 39,000×g for 20 minutes followed by filtration though 0.45 micron filters. The cleared lysate was applied to a 10 ml column of HisBind resin, washed with imidazole wash buffer (20 mM imidazole, 6 M urea, 0.5 M NaCl, 20 mM Tris-HCl, pH 7.9). The recombinant Ara h 2 was then released from the column using elution buffer (1 M imidazole, 0.5 M NaCl, 20 mM Tris-HCl, pH 7.9). The elution buffer was replaced with phosphate buffered saline by dialysis. The purification of recombinant Ara h 2 was followed by SIDS PAGE and immunoblots. Peanut specific serum IgE was used as a primary antibody.

Skin Prick Tests. The ability of purified native and recombinant Ara h 2 to elicit the IgE mediated degranulation of mast cells was evaluated using prick skin tests in a peanut allergic individual. An individual meeting the criteria for peanut allergy (convincing history or positive double blind placebo controlled food challenge) and a non-allergic control were selected for the testing. Purified native and recombinant Ara h 2 and whole peanut extract (Greer Laboratories, Lenoir, N.C.) were tested. Twenty microliters of the test solution were applied to the forearm of the volunteer and the skin beneath pricked with a sterile needle. Testing was started at the lowest concentration (less than or equal to 1 mg/ml) and increased ten fold each round to the highest concentration or until a positive reaction was observed. Mean diameters of the wheal and erythema were measured and compared to the negative saline control. A positive reaction was defined as a wheal 3 mm larger then the negative control. Histamine was used as the positive control.

Results

Identification of the Linear IgE-Binding Epitopes of Ara h 1, Ara h 2 and Ara h 3 Allergens.

Epitope mapping was performed on the Ara h 1, Ara h 2 and Ara h 3 allergens by synthesizing each of these proteins in 15 amino acid long overlapping peptides that were offset from each other by 8 amino acids. The peptides were then probed with a pool of serum IgE from 15 patients with documented peanut hypersensitivity. This analysis resulted in multiple IgE binding regions being identified for each allergen. The exact position of each IgE binding epitope was then determined by re-synthesizing these IgE reactive regions as 10 or 15 amino acid long peptides that were offset from each other by two amino acids. These peptides were probed with the same pool of serum IgE from peanut sensitive patients as used before. An example of this procedure for each of the peanut allergens is shown in FIGS. 5-7. FIG. 5 depicts twenty-two 10-mer peptides (SEQ ID NOs. 45-66) that span amino acid residues 82-133 (SEQ ID NO. 44) of the Ara h 1 allergen (SEQ ID NO. 2). This region of the Ara h 1 allergen includes epitopes 4, 5, 6, and 7, as identified in Table 1. FIG. 6 depicts seven 10-mer peptides (SEQ ID NOs. 68-74) that span amino acid residues 55-76 (SEQ ID NO. 67) of the Ara h 2 allergen (SEQ ID NO. 4). This region of the Ara h 2 allergen includes epitopes 6 and 7 as identified in Table 2. FIG. 7 depicts six 15-mer peptides (SEQ ID NOs. 76-81) that span amino acid residues 299-321 (SEQ ID NO. 75) of the Ara h 3 allergen (SEQ ID NO. 6). This region of the Ara h 3 allergen includes epitope 4 as identified in Table 3. This analysis revealed that there were 23 linear IgE binding epitopes on Ara h 1, 10 epitopes on Ara h 2, and 4 epitopes on Ara h 3.

In an effort to determine which, if any, of the epitopes were recognized by the majority of patients with peanut hypersensitivity, each set of epitopes identified for the peanut allergens were synthesized and then probed individually with serum IgE from 10 different patients. All of the patient sera tested recognized multiple epitopes.

Table 1 shows the amino acid sequence and position of each epitope within the Ara h 1 protein (SEQ ID NO. 2) of all 23 IgE binding epitopes mapped to this molecule. Table 2 shows the amino acid sequence and position of each epitope within the Ara h 2 protein (SEQ ID NO. 4) of all 10 IgE binding epitopes mapped to this molecule. Table 3 shows the amino acid sequence and position of each epitope within the Ara h 3 protein (SEQ ID NO. 6) of all 4 IgE binding epitopes mapped to this molecule.

Four epitopes of the Ara h 1 allergen (peptides 1, 3, 4, 17 of Table 1), three epitopes of the Ara h 2 allergen (peptides 3, 6, 7 of Table 2), and one epitope of the Ara h 3 allergen (peptide 2 of Table 3) were immunodominant.

TABLE 1

Ara h 1 IgE binding epitopes

| EPITOPE | AA SEQUENCE | POSITION | SEQ ID NO. |
|---|---|---|---|
| 1 | AKSSPYQKKT | 25-34 | 7 |
| 2 | QEPDDLKQKA | 48-57 | 8 |
| 3 | LEYDPRLVYD | 65-74 | 9 |
| 4 | GERTRGRQPG | 89-98 | 10 |
| 5 | PGDYDDDRRQ | 97-106 | 11 |
| 6 | PRREEGGRWG | 107-116 | 12 |
| 7 | REREEDWRQP | 123-132 | 13 |
| 8 | EDWRRPSHQQ | 134-143 | 14 |
| 9 | QPRKIRPEGR | 143-152 | 15 |
| 10 | TPGQFEDFFP | 294-303 | 16 |
| 11 | SYLQEFSRNT | 311-320 | 17 |
| 12 | FNAEFNEIRR | 325-334 | 18 |
| 13 | EQEERGQRRW | 344-353 | 19 |
| 14 | DITNPINLRE | 393-402 | 20 |
| 15 | NNFGKLFEVK | 409-418 | 21 |
| 16 | GTGNLELVAV | 461-470 | 22 |
| 17 | RRYTARLKEG | 498-507 | 23 |
| 18 | ELHLLGFGIN | 525-534 | 24 |
| 19 | HRIFLAGDKD | 539-548 | 25 |
| 20 | IDQIEKQAKD | 551-560 | 26 |
| 21 | KDLAFPGSGE | 559-568 | 27 |
| 22 | KESHFVSARP | 578-587 | 28 |
| 23 | PEKESPEKED | 597-606 | 29 |

The underlined portions of each peptide are the smallest IgE binding sequences as determined by this analysis. All of these sequences can be found in SEQ ID NO. 2.

TABLE 2

Ara h 2 IgE binding epitopes

| EPITOPE | AA SEQUENCE | POSITION | SEQ ID NO. |
|---|---|---|---|
| 1 | HASARQQWEL | 15-24 | 30 |
| 2 | QWELQGDRRC | 21-30 | 31 |
| 3 | DRRCQSQLER | 27-36 | 32 |
| 4 | LRPCEQHLMQ | 39-48 | 33 |
| 5 | KIQRDEDSYE | 49-58 | 34 |
| 6 | YERDPYSPSQ | 57-66 | 35 |
| 7 | SQDPYSPSPY | 65-74 | 36 |

TABLE 2-continued

Ara h 2 IgE binding epitopes

| EPITOPE | AA SEQUENCE | POSITION | SEQ ID NO. |
|---------|-------------|----------|------------|
| 8 | DRLQGRQQEQ | 115-124 | 37 |
| 9 | KRELRNLPQQ | 127-136 | 38 |
| 10 | QRCDLDVESG | 143-152 | 39 |

The underlined portions of each peptide are the smallest IgE binding sequences as determined by this analysis. All of these sequences can be found in SEQ ID NO. 4.

TABLE 3

Ara h 3 IgE binding epitopes

| EPITOPE | AA SEQUENCE | POSITION | SEQ ID NO. |
|---------|-------------|----------|------------|
| 1 | IETWNPNNQEFECAG | 33-47 | 40 |
| 2 | GNIFSGFTPEFLEQA | 240-254 | 41 |
| 3 | VTVRGGLRILSPDRK | 279-293 | 42 |
| 4 | DEDEYEYDEEDRRRG | 303-317 | 43 |

The underlined portions of each peptide are the smallest IgE binding sequences as determined by this analysis. All of these sequences can be found in SEQ ID NO. 6.

Example 6

Modification of Peanut Allergens to Decrease Allergenicity

The major linear IgE binding epitopes of the peanut allergens were mapped using overlapping peptides synthesized on an activated cellulose membrane and pooled serum IgE from 15 peanut sensitive patients, as described in Example 1. The size of the epitopes ranged from six to fifteen amino acids in length. The amino acids essential to IgE binding in each of the epitopes were determined by synthesizing duplicate peptides with single amino acid changes at each position. These peptides were then probed with pooled serum IgE from 15 patients with peanut hypersensitivity to determine if the changes affected peanut-specific IgE binding. For example, epitope 9 in Table 1 was synthesized with an alanine or methionine residue substituted for one of the amino acids and probed. The following amino acids were substituted (first letter is the one-letter amino acid code for the residue normally at the position, the residue number, followed by the amino acid that was substituted for this residue; the numbers indicate the position of each residue in the Ara h 1 protein, SEQ ID NO. 2): Q143A; P144A; R145A; K146A; I147A; R148A; P149A; E150A; G151A; R152A; Q143M; P144M; R145M; K146M; I147M; R148M; P149M; E150M; G151M; R152M. The immunoblot strip containing the wild-type and mutated peptides of epitope 9 showed that binding of pooled serum IgE to individual peptides was dramatically reduced when either alanine or methionine was substituted for each of the amino acids at positions 144, 145, and 147-150 of Ara h 1 shown in SEQ ID NO. 2. Changes at positions 144, 145, 147, and 148 of Ara h 1 shown in SEQ ID NO. 2 had the most dramatic effect when methionine was substituted for the wild-type amino acid, resulting in less than 1% of peanut specific IgE binding to these peptides. In contrast, the substitution of an alanine for arginine at position 152 of Ara h 1 shown in SEQ ID NO. 2 resulted in increased IgE binding. The remaining Ara h 1 epitopes, and the Ara h 2 and Ara h 3 epitopes, were tested in the same manner and the intensity of IgE binding to each spot was determined as a percentage of IgE binding to the wild-type peptide. Any amino acid substitution that resulted in less than 1% of IgE binding when compared to the wild-type peptide was noted and is indicated in Tables 4-6. Table 4 shows the amino acids that were determined to be critical to IgE binding in each of the Ara h 1 epitopes. Table 5 shows the amino acids that were determined to be critical to IgE binding in each of the Ara h 2 epitopes. Table 6 shows the amino acids that were determined to be critical to IgE binding in each of the Ara h 3 epitopes.

This analysis indicated that each epitope could be mutated to a non-IgE binding-peptide by the substitution of a single amino acid residue.

The results discussed above for Ara h 1, Ara h 2, and Ara h 3 demonstrate that once an IgE binding site has been identified, it is possible to reduce IgE binding to this site by altering a single amino acid of the epitope. The observation that alteration of a single amino acid leads to the loss of IgE binding in a population of peanut-sensitive individuals is significant because it suggests that while each patient may display a polyclonal IgE reaction to a particular allergen, IgE from different patients that recognize the same epitope must interact with that epitope in a similar fashion. Besides finding that many epitopes contained more than one residue critical for IgE binding, it was also determined that more than one residue type (ala or met) could be substituted at certain positions in an epitope with similar results. This allows for the design of a hypoallergenic protein that would be effective at blunting allergic reactions for a population of peanut sensitive individuals. Furthermore, the creation of a plant producing a peanut where the IgE binding epitopes of the major allergens have been removed should prevent the development of peanut hypersensitivity in individuals genetically predisposed to this food allergy.

TABLE 4

Amino acids critical to IgE binding of Ara h 1

| EPITOPE | AA SEQUENCE | POSITION | SEQ ID NO. |
|---------|-------------|----------|------------|
| 1 | AKSSPYQKKT | 23-34 | 7 |
| 2 | QEPDDLKQKA | 48-57 | 8 |
| 3 | LEYDPRLVYD | 65-74 | 9 |
| 4 | GERTRGRQPG | 89-98 | 10 |
| 5 | PGDYDDDRRQ | 97-106 | 11 |
| 6 | PRREEGGRWG | 107-116 | 12 |
| 7 | REREEDWRQP | 123-132 | 13 |
| 8 | EDWRRPSHQQ | 134-143 | 14 |
| 9 | QPRKIRPEGR | 143-152 | 15 |
| 10 | TPGQFEDFFP | 294-303 | 16 |
| 11 | SYLQEFSRNT | 311-320 | 17 |
| 12 | FNAEFNEIRR | 325-334 | 18 |
| 13 | EQEERGQRRW | 344-353 | 19 |
| 14 | DITNPINLRE | 393-402 | 20 |

TABLE 4-continued

Amino acids critical to IgE binding of Ara h 1

| EPITOPE | AA SEQUENCE | POSITION | SEQ ID NO. |
|---|---|---|---|
| 15 | NNFGKLFEVK | 409-418 | 21 |
| 17 | RRYTARLKEG | 498-507 | 23 |
| 18 | ELHLLGFGIN | 525-534 | 24 |
| 19 | HRIFLAGDKD | 539-548 | 25 |
| 20 | IDQIEKQAKD | 551-560 | 26 |
| 21 | KDLAFPGSGE | 559-568 | 27 |
| 22 | KESHFVSARP | 578-587 | 28 |

The Ara h 1 IgE binding epitopes are indicated as the single letter amino acid code. The position of each peptide with respect to the Ara h 1 protein (SEQ ID NO. 2) is indicated. The amino acids that, when altered, lead to loss of IgE binding are shown as the bold, underlined residues. Epitopes 16 and 23 were not included in this study because they were recognized by a single patient who was no longer available to the study. All of these sequences can be found in SEQ ID NO. 2.

TABLE 5

Amino acids critical to IgE binding of Ara h 2

| EPITOPE | AA SEQUENCE | POSITION | SEQ ID NO. |
|---|---|---|---|
| 1 | HASARQQWEL | 15-24 | 30 |
| 2 | QWELQGDRRC | 21-30 | 31 |
| 3 | DRRCQSQLER | 27-36 | 32 |
| 4 | LRPCEQHLMQ | 39-48 | 33 |
| 5 | KIQRDEDSYE | 49-58 | 34 |
| 6 | YERDPYSPSQ | 57-66 | 35 |
| 7 | SQDPYSPSPY | 65-74 | 36 |
| 8 | DRLQGRQQEQ | 115-124 | 37 |
| 9 | KRELRNLPQQ | 127-136 | 38 |
| 10 | QRCDLDVESG | 143-152 | 39 |

The Ara h 2 IgE binding epitopes are indicated as the single letter amino acid code. The position of each peptide with respect to the Ara h 2 protein (SEQ ID NO. 4) is indicated. The amino acids that, when altered, lead to loss of IgE binding are shown as the bold, underlined residues. All of these sequences can be found in SEQ ID NO. 4.

TABLE 6

Amino acids critical to IgE binding of Ara h 3

| EPITOPE | AA SEQUENCE | POSITION | SEQ ID NO. |
|---|---|---|---|
| 1 | IETWNPNNQEFECAG | 33-47 | 40 |
| 2 | GNIFSGFTPEFLEQA | 240-254 | 41 |
| 3 | VTVRGGLRILSPDRK | 279-293 | 42 |
| 4 | DEDEYEYDEEDRRRG | 303-317 | 43 |

The Ara h 3 IgE binding epitopes are indicated as the single letter amino acid code. The position of each peptide with respect to the Ara h 3 protein (SEQ ID NO. 6) is indicated. The amino acids that, when altered, lead to loss of IgE binding are shown as the bold, underlined. All of these sequences can be found in SEQ ID NO. 6.

Example 7

A Modified Ara h 2 Protein Binds Less IgE but Similar Amounts of IgG

In order to determine the effect of changes to multiple epitopes within the context of the intact allergen, four epitopes (including the three immunodominant epitopes) of the Ara h 2 allergen were mutagenized and the protein produced recombinantly. The amino acids at position 20, 31, 60, and 67 of the Ara h 2 protein (shown in SEQ ID NO. 4) were changed to alanine by mutagenizing the gene encoding this protein by standard techniques. These residues are located in epitopes 1, 3, 6, and 7 and represent amino acids critical to IgE binding that were determined in Example 2. The modified and wild-type versions of this protein were produced and immunoblot analysis performed using serum from peanut sensitive patients. These results showed that the modified version of this allergen bound significantly less IgE than the wild-type version of these recombinant proteins but bound similar amounts of IgG.

Example 8

Figure 8:
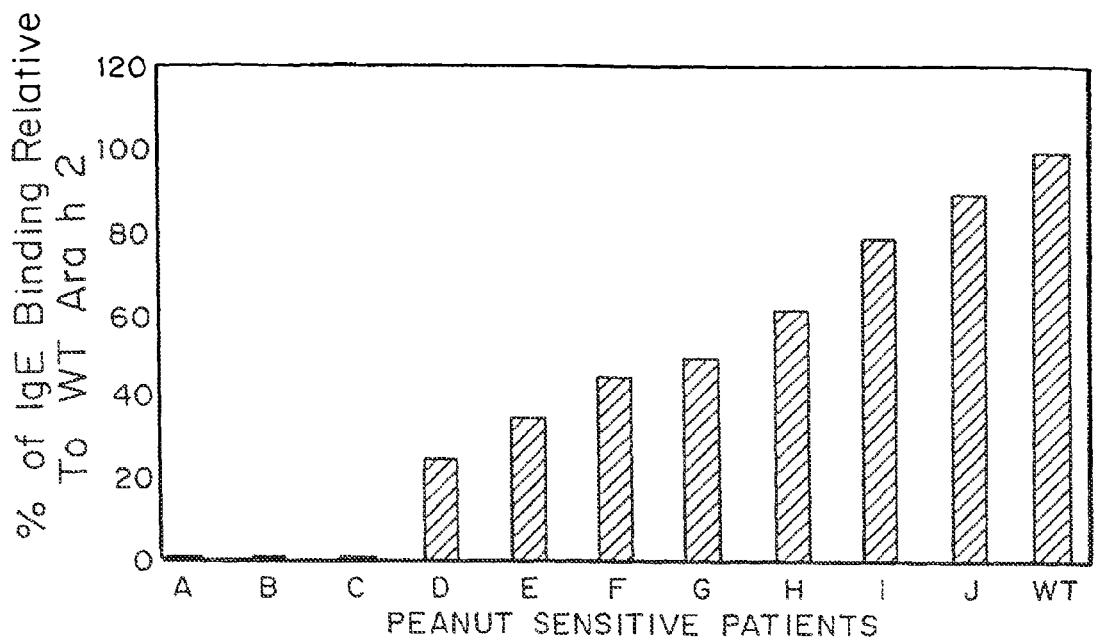
FIG. 8 shows the effect the modified Ara h 2 protein has on IgE binding.
Figure 9:
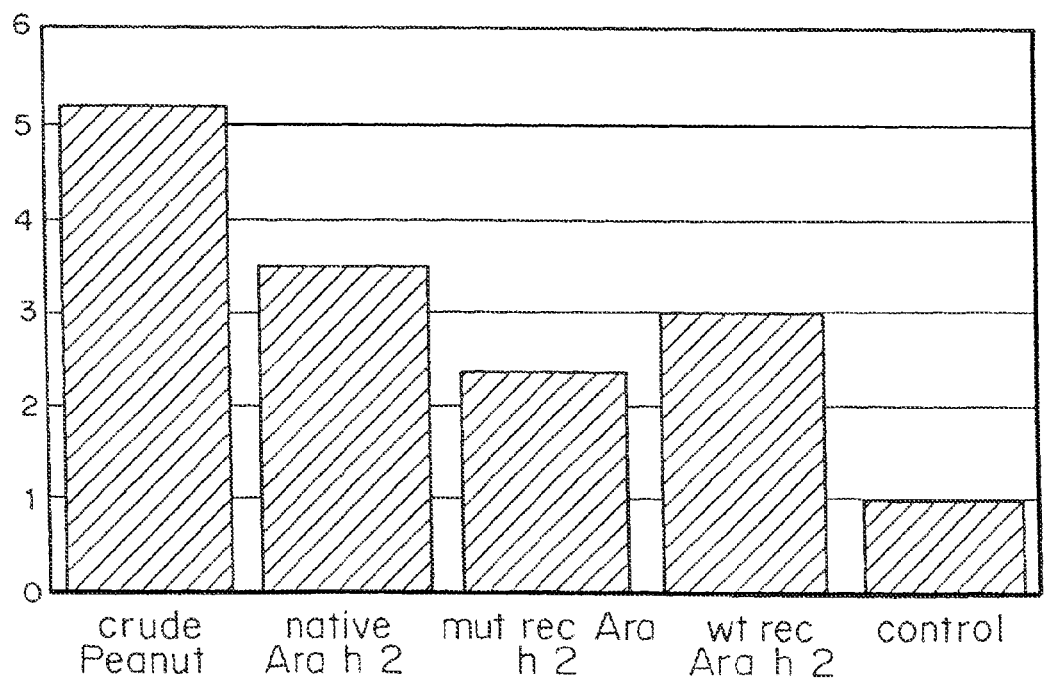
FIG. 9 shows the results of T cell proliferation assays using the wild-type and modified Ara h 2 protein.

A Modified Ara h 2 Protein Retains the Ability to Stimulate T Cells to Proliferate The modified recombinant Ara h 2 protein described in Example 3 was used in T cell proliferation assays to determine if it retained the ability to activate T cells from peanut sensitive individuals. Proliferation assays were performed on T cell lines grown in short-term culture developed from six peanut sensitive patients. T cells lines were stimulated with either 50 µg of crude peanut extract, 10 µg of native Ara h 2, 10 µg of recombinant wild-type Ara h 2, or 10 µg of modified recombinant Ara h 2 protein and the amount of 3H-thymidine determined for each cell line. Results were expressed as the average stimulation index (SI) which reflected the fold increase in 3H-thymidine incorporation exhibited by cells challenged with allergen when compared with media treated controls (FIG. 8).

Example 9

A Modified Ara h 2 Protein Elicits a Smaller Wheal and Flare in Skin Prick Tests of a Peanut Sensitive Individual The modified recombinant Ara h 2 protein described in Example 3 and the wild-type version of this recombinant protein were used in a skin prick test of a peanut sensitive individual. Ten micrograms of these proteins were applied separately to the forearm of a peanut sensitive individual, the skin pricked with a sterile needle, and 10 minutes later any wheal and flare that developed was measured. The wheal and flare produced by the wild-type Ara h 2 protein (8 mm×7 mm) was approximately twice as large as that produced by the modified Ara h 2 protein (4 mm×3 mm). A control subject (no peanut hypersensitivity) tested with the same proteins had no visible wheal and flare but, as expected, gave positive results when challenged with histamine. In addition, the test subject gave no positive results when tested with PBS alone. These results indicate that an allergen with only 40% of its IgE binding epitopes modified (4/10) can give measurable reduction in reactivity in an in vivo test of a peanut sensitive patient.

These same techniques can be used with the other known peanut allergens, Ara h 1 (SEQ ID NOs. 1 and 2), Ara h 3 (SEQ ID NOs. 5 and 6), or any other allergen.

Modifications and variations of the methods and materials described herein will be obvious to those skilled in the art. Such modifications and variations are intended to come within the scope of the appended claims.

APPENDIX A

| ALLERGEN SOURCE | SYSTEMATIC AND ORIGINAL NAMES | MW KDA | SEQ | ACCESSION NO. OR REFERENCES |
|---|---|---|---|---|
| | WEED POLLENS *Asterales* | | | |
| *Ambrosia artemisiifolia* (short ragweed) | Amb a 1; antigen E | 38 | C | 8, 20 |
| | Amb a 2; antigen K | 38 | C | 8, 21 |
| | Amb a 3; Ra3 | 11 | C | 22 |
| | Amb a 5; Ra5 | 5 | C | 11, 23 |
| | Amb a 6; Ra6 | 10 | C | 24, 25 |
| | Amb a 7; Ra7 | 12 | P | 26 |
| | Amb a ? | 11 | C | 27 |
| *Ambrosia trifida* (giant ragweed) | Amb t 5; Ra5G | 4.4 | C | 9, 10, 28 |
| *Artemisia vulgaris* (mugwort) | Art v 1 | 27-29 | C | 28A |
| | Art v 2 | 35 | P | 29 |
| *Helianthus annuus* (sunflower) | Hel a 1 | 34 | — | 29a |
| | Hel a 2; profilin | 15.7 | C | Y15210 |
| *Mercurialis annua* | Mer a 1; profilin | 14-15 | C | Y13271 |
| | GRASS POLLENS *Poales* | | | |
| *Cynodon dactylon* (Bermuda grass) | Cyn d 1 | 32 | C | 30, S83343 |
| | Cyn d 7 | | C | 31, X91256 |
| | Cyn d 12; profilin | 14 | C | 31a, Y08390 |
| *Dactylis glomerata* (orchard grass) | Dac g 1; AgDg1 | 32 | P | 32 |
| | Dac g 2 | 11 | C | 33, S45354 |
| | Dac g 3 | | C | 33a, U25343 |
| | Dac g 5 | 31 | P | 34 |
| *Holcus lanatus* (velvet grass) | Hol l 1 | | C | Z27084, Z68893 |
| *Lolium perenne* (rye grass) | Lol p 1; group I | 27 | C | 35, 36 |
| | Lol p 2; group II | 11 | C | 37, 37a, X73363 |
| | Lol p 3; group III | 11 | C | 38 |
| | Lol p 5; Lol p IX, Lol p Ib | 31/35 | | 34, 39 |
| | Lol p 11; trypsin inh. Related | 16 | | 39a |
| *Phalaris aquatica* (canary grass) | Pha a 1 | | C | 40, S80654 |
| *Phleum pratense* (timothy grass) | Phl p 1 | 27 | C | X78813 |
| | Phl p 2 | | C | 41, X75925 |
| | Phl p 4 | | P | 41A |
| | Phl p 5; Ag25 | 32 | C | 42 |
| | Phl p 6 | | C | 43, Z27082 |
| | Phl p 12; profilin | | C | 44, X77583 |
| | Phl p 13; polygalacturonase | 55-60 | C | AJ238848 |
| *Poa pratensis* (Kentucky blue grass) | Poa p 1; group I | 33 | P | 46 |
| | Poa p 5 | 31/34 | C | 34, 47 |
| *Sorghum halepense* (Johnson grass) | Sor h 1 | | C | 48 |
| | TREE POLLENS *Fagales* | | | |
| *Alnus glutinosa* (alder) | Aln g 1 | 17 | C | S50892 |
| *Betula verrucosa* (birch) | Bet v 1 | 17 | C | see list of isoallergens M65179 |
| | Bet v 2; profilin | 15 | C | X79267 |
| | Bet v 3 | 8 | C | X87153/554819 |
| | Bet v 4 | | C | AF135127 |
| | Bet v 5; isoflavone reductase homologue | 33.5 | C | |
| | Bet v 7; cyclophilin | 18 | C | P P81531 |
| *Carpinus betulus* (hornbeam) | Car b 1 | 17 | C | 51 |

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|
| *Castanea sativa* (chestnut) | Cas s 1; Bet v 1 homologue<br>Cas s5; chitinase | 22 | P | 52 |
| *Corylus avelana* (hazel) | Cor a 1 | 17 | C | 53 |
| *Quercus alba* (white oak) | Que a 1 | 17 | P | 54 |
| *Cryptomeria japonica* (sugi) | Cry j 1<br>Cry j 2 | 41-45 | C<br>C | 55, 56<br>57, D29772 |
| *Juniperus ashei* (mountain cedar) | Jun a 1<br>Jun a 3 | 43<br>30 | P<br>P | P81294<br>P81295 |
| *Juniperus oxycedrus* (prickly juniper) | Jun o 2; calmodulin-like | 29 | C | AF031471 |
| *Juniperus sabinoides* (mountain cedar) | Jun s 1 | 50 | P | 58 |
| *Juniperus virginiana* (eastern red cedar) | Jun v 1 | 43 | P | P81825 |
| Oleales | | | | |
| *Fraxinus excelsior* (ash) | Fra e 1 | 20 | P | 58A |
| *Ligustrum vulgare* (privet) | Lig v 1 | 20 | P | 58A |
| *Olea europea* (olive) | Ole e 1;<br>Ole e 2; profilin<br>Ole e 3;<br>Ole e 4;<br>Ole e 5; superoxide dismutase<br>Ole e 6; | 16<br>15-18<br>9.2<br>32<br>16<br>10 | C<br>C<br><br>P<br>P<br>C | 59, 60<br>60A<br>60B<br>P80741<br>P80740<br>U86342 |
| *Syringa vulgaris* (lilac) | Syr v 1 | 20 | P | 58A |
| MITES | | | | |
| *Acarus siro* (mite) | Aca s 13; fatty acid-bind.prot. | 14* | C | AJ006774 |
| *Blomia tropicalis* (mite) | Blo t 5;<br>Blo t 12; Bt1 1a<br>Blo t 13; Bt6 fatty acid-binding prot | | C<br>C<br>C | U59102<br>U27479<br>U58106 |
| *Dermatophagoides pteronyssinus* (mite) | Der p 1; antigen P1<br>Der p 2;<br>Der p 3; trypsin<br>Der p 4; amylase<br>Der p 5;<br>Der p 6; chymotrypsin<br>Der p 7;<br>Der p 8; glutathione transferase<br>Der p 9; collagenolytic serine prot.<br>Der p 10; tropomyosin<br>Der p 14; apolipophorin like p | 25<br>14<br>28/30<br>60<br>14<br>25<br>22-28<br><br><br>36<br> | C<br>C<br>C<br>C<br>P<br>C<br>C<br>P<br>C<br>C<br>C | 61<br>62<br>63<br>64<br>65<br>66<br>67<br>67A<br>67B<br>Y14906<br>Epton p.c. |
| *Dermatophagoides microceras* (mite) | Der m 1; | 25 | P | 68 |
| *Dermatophagoides farinae* (mite) | Der f 1;<br>Der f 2;<br>Der f 3;<br>Der f 10; tropomyosin<br>Der f 11; paramyosin<br>Der f 14; Mag3, apolipophorin | 25<br>14<br>30<br><br>98<br> | C<br>C<br>C<br>C<br>C<br>C | 69<br>70, 71<br>63<br>72<br>72a<br>D17686 |
| *Euroglyphus maynei* (mite) | Eur m 14; apolipophorin | 177 | C | AF149827 |
| *Lepidoglyphus destructor* (storage mite) | Lep d 2.0101;<br>Lep d 2.0102; | 15<br>15 | C<br>C | 73, 74, 75<br>75 |
| ANIMALS | | | | |
| *Bos domesticus* (domestic cattle) (see also foods) | Bos d 2; Ag3,lipocalin<br>Bos d 4; alpha-lactalbumin<br>Bos d 5; beta-lactoglobulin<br>Bos d 6; serum albumin<br>Bos d 7; immunoglobulin<br>Bos d 8; caseins | 20<br>14.2<br>18.3<br>67<br>160<br>20-30 | C<br>C<br>C<br>C<br><br> | 76, L42867<br>M18780<br>X14712<br>M73993<br>77<br>77 |
| *Canis familiaris* (Canis domesticus) (dog) | Can f 1;<br>Can f 2;<br>Can f ?; albumin | 25<br>27<br> | C<br>C<br>C | 78, 79<br>78, 79<br>572946 |
| *Equus caballus* (domestic horse) | Equ c 1; lipocalin<br>Equ c 2; lipocali | 25<br>18.5 | C<br>P | U70823<br>79A, 79B |
| *Felis domesticus* (cat saliva) | Fel d 1; cat-1 | 38 | C | 15 |

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|
| *Mus musculus* (mouse urine) | Mus m 1; MUP | 19 | C | 80, 81 |
| *Rattus norvegius* (rat urine) | Rat n 1 | 17 | C | 82, 83 |
| | FUNGI *Ascomycota* Dothidiales | | | |
| *Alternaria alternata* | Alt a 1; | 28 | C | U82633 |
| | Alt a 2; | 25 | C | U87807, U87808 |
| | Alt a 3; heat shock protein | 70 | C | X78222, |
| | Alt a 6; ribosomal protein | 11 | C | U87806 |
| | Alt a 7; YCP4 protein | 22 | C | X78225 |
| | Alt a 10; aldehyde dehydrogenase | 53 | C | X78227, P42041 |
| | Alt a 11; enolase | 45 | C | U82437 |
| | Alt a 12; acid.ribosomal prot P1 | 11 | C | X84216 |
| *Cladosporium herbarum* | Cla h 1; | 13 | | 83a, 83b |
| | Cla h 2; | 23 | | 83a, 83b |
| | Cla h 3; aldehyde dehydrogenase | 53 | C | X78228 |
| | Cla h 4; ribosomal protein | 11 | C | X78223 |
| | Cla h 5; YCP4 protein | 22 | C | X78224 |
| | Cla h 6; enolase | 46 | C | X78226 |
| | Cla h 12; acid.ribosomal prot P1 | 11 | C | X85180 |
| | Eurotiales | | | |
| | Asp fl 13; alkaline serine proteinase | 34 | | 84 |
| *Aspergillus Fumigatus* | Asp f 1; | 18 | C | 83781, S39330 |
| | Asp f 2; | 37 | C | U56938 |
| | Asp f 3; peroxisomal protein | 19 | C | U20722 |
| | Asp f 4; | 30 | C | AJ001732 |
| | Asp f 5; metalloprotease | 42 | C | Z30424 |
| | Asp f 6; Mn superoxide dismutase | 26.5 | C | U53561 |
| | Asp f 7; | 12 | C | AJ223315 |
| | Asp f 8; ribosomal protein P2 | 11 | C | AJ224333 |
| | Asp f 9; | 34 | C | AJ223327 |
| | Asp f 10; aspartic protease | 34 | | X85092 |
| | Asp f 11; peptidyl-prolyl isom | 24 | | 84a |
| | Asp f 12; heat shock prot. P70 | 65 | C | U92465 |
| | Asp f 13; alkaline serine proteinase | 34 | | 84b |
| | Asp f 15; | 16 | C | AJ002026 |
| | Asp f 16; | 43 | C | g3643813 |
| | Asp f 17; | 34 | C | AJ224865 |
| | Asp f 18; vacuolar serine | 90 | | 84c |
| | Asp f ?; | 55 | P | 85 |
| | Asp f ?; | | P | 86 |
| *Aspergillus niger* | Asp n 14; beta-xylosidase | 105 | C | AF108944 |
| | Asp n 18; vacuolar serine proteinase | 34 | C | 84b |
| | Asp n ?; | 85 | C | Z84377 |
| *Aspergillus oryzae* | Asp o 2; TAKA-amylase A | 53 | C | D00434, M33218 |
| | Asp o 13; alkaline serine proteinase | 34 | C | X17561 |
| *Penicillium brevicompactum* | Pen b 13; alkaline serine Proteinase | 33 | | 86a |
| *Penicillium citrinum* | Pen c 1; heat shock protein P70 | 70 | C | U64207 |
| | Pen c 3; peroxisomal membrane protein | | | 86b |
| | Pen c 13; alkaline serine proteinase | 33 | | 86a |
| *Penicillium notatum* | Pen n 1; N-acetyl glucosaminidase | 68 | | 87 |
| | Pen n 13; alkaline serine proteinase | 34 | | 89 |
| | Pen n 18; vacuolar serine proteinase | 32 | | 89 |
| *Penicillium oxalicum* | Pen o 18; vacuolar serine proteinase | 34 | | 89 |
| | Onygenales | | | |
| *Trichophyton rubrum* | Tri r 2; | | C | 90 |
| | Tri r 4; serine protease | | C | 90 |
| *Trichophyton tonsurans* | Tri t 1; | 30 | P | 91 |
| | Tri t 4; serine protease | 83 | C | 90 |
| | Saccharomycetales | | | |
| *Candida albicans* | Cand a 1 | 40 | C | 88 |
| *Candida boidinii* | Cand b 2 | 20 | C | J04984, J04985 |

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|
| | *Basidiomycota* | | | |
| | Basidiolelastomycetes | | | |
| *Malassezia furfur* | Mal f 1; | | | 91a |
| | Mal f 2; MF1 peroxisomal membrane protein | 21 | C | AB011804 |
| | Mal f 3; MF2 peroxisomal membrane protein | 20 | C | AB011805 |
| | Mal f 4; | 35 | C | Takesako, p.c. |
| | Mal f 5; | 18* | C | AJ011955 |
| | Mal f 6; cyclophilin homologue | 17* | C | AJ011956 |
| | Basidiomycetes | | | |
| *Psilocybe cubensis* | Psi c 1; | 16 | | 91b |
| | Psi c 2; cyclophilin | | | |
| *Coprinus comatus* | Cop c 1; | 11 | C | AJ132235 |
| (shaggy cap) | Cop c 2; | | | |
| | Cop c 3; | | | Brander, p.c. |
| | Cop c 5; | | | Brander, p.c. |
| | Cop c 7; | | | Brander, p.c. |
| | INSECTS | | | |
| *Aedes aegyptii* | Aed a 1; apyrase | 68 | C | L12389 |
| (mosquito) | Aed a 2; | 37 | C | M33157 |
| *Apis mellifera* | Api m 1; phospbolipase A2 | 16 | C | 92 |
| (honey bee) | Api m 2; hyaluronidase | 44 | C | 93 |
| | Api m 4; meliltin | 3 | C | 94 |
| | Api m 6; | 7-8 | P | Kettner, p.c. |
| *Bombus pennsylvanicus* | Bom p 1; phospholipasc | 16 | P | 95 |
| (bumble bee) | Bom p4; protease | | P | 95 |
| *Blallclla germanica* | Bla g 1; BdWk | | C | 96 |
| (German cockroach) | Bla g 2; aspartie protease | 36 | C | |
| | Bla g 4; calycin | 21 | C | 97 |
| | Bla g 5; glutathione transf. | 22 | C | 98 |
| | Bla g 6; troponin C | 27 | C | 98 |
| *Periplaneta americana* | Per a 1; Cr-PII | 72-78 | C | 98A |
| (American cockroach) | Per a 3; Cr-PI | | C | |
| | Per a 7; tropomyosin | 37 | C | Y14854 |
| *Chironomus thummi thummi* (midges) | Chi T 1-9; hemoglobin | 16 | C | 99 |
| | Chi t 1.01; component III | 16 | C | P02229 |
| | Chi t 1.02; component IV | 16 | C | P02230 |
| | Chi t 2.0101; component I | 16 | C | P02221 |
| | Chi t 2.0102; component IA | 16 | C | P02221 |
| | Chi t 3; component II-beta | 16 | C | P02222 |
| | Chi t 4; component IIIA | 16 | C | P02231 |
| | Chi t 5; component VI | 16 | C | P02224 |
| | Chi t 6.01; component VIIA | 16 | C | P02226 |
| | Chi t 6.02; component IX | 16 | C | P02223 |
| | Chi t 7; component VIIB | 16 | C | P02225 |
| | Chi t 8; component VIII | 16 | C | P02227 |
| | Chi t 9; component X | 16 | C | P02228 |
| *Dolichovespula maculata* | Dol m 1: phospholipasc A1 | 35 | C | 100 |
| | Dol m 2; hyaluronidase | 44 | C | 101 |
| (white face hornet) | Dol m 5; antigen 5 | 23 | C | 102, 103 |
| *Dolichovespula arenaria* | Dol a 5; antigen 5 | 23 | C | 104 |
| (yellow hornet) | | | | |
| *Polistes annularies* | Pol a 1; phospholipasc A1 | 35 | P | 105 |
| (wasp) | Pol a 2; hyaluronidase | 44 | P | 105 |
| | Pol a 5; antigen 5 | 23 | C | 104 |
| *Polistes dominulus* | Pol d 1; | 32-34 | C | DR Hoffman |
| (Mediterranean paper | Pol d 4; serine protease | | | DR Hoffman |
| wasp) | Pol d 5; | | | P81656 |
| *Polistes exclamans* | Pol e 1; phospholipasc A1 | 34 | P | 107 |
| (wasp) | Pol e 5; antigen 5 | 23 | C | 104 |
| *Polistes fuscatus* (wasp) | Pol f 5; antigen 5 | 23 | C | 106 |
| *Polistes metricus* (wasp) | Pol m 5; antigen 5 | 23 | P | 106 |
| *Vespa crabo* | Vesp c 1; phospholipase | 54 | P | 107 |
| (European hornet) | Vespc 5.0101; antigen 5 | 23 | C | 106 |
| | Vesp c 5.0102; antigen 5 | 23 | C | 106 |
| *Vespa mandarina* | Vesp m 1.01; | | | DR Hoffman |
| (giant asian hornet) | Vesp m 1.02; | | | DR Hoffman |
| | Vesp m 5; | | | P81657 |

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|
| *Vespula flavopilosa* (yellowjacket) | Ves f 5; antigen 5 | 23 | C | 106 |
| *Vespula germanica* (yellowjacket) | Ves g 5; antigen 5 | 23 | C | 106 |
| *Vespula maculifrons* (yellowjacket) | Ves m 1; phospholipase A1 | 33.5 | C | 108 |
| | Ves m 2; hyaluronidase | 44 | P | 109 |
| | Ves m 5; antigen 5 | 23 | 23 | 104 |
| *Vespula pennsylvanica* (yellowjacket) | Ves p 5; antigen 5 | 23 | C | 106 |
| *Vespula squamosa* (yellowjacket) | Ves s 5; antigen 5 | 23 | C | 106 |
| *Vespula vidua* (wasp) | Ves vi 5; | 23 | C | 106 |
| *Vespula vulgaris* (yellowjacket) | Ves v 1; phopholipase A1 | 35 | C | 105A |
| | Ves v 2; hyaluronidase | 44 | P | 105A |
| | Ves v 5; antigen 5 | 23 | C | 104 |
| *Myrmecia pilosula* (Australian jumper ant) | Myr p 1, | | C | X70256 |
| | Myr p 2; | | C | S81785 |
| *Solenopsis geminata* (tropical fire ant) | Sol g 2; | | | DR Hoffman |
| | Sol g 4 | | | DR Hoffman |
| *Solenopsis invicta* (fire ant) | Sol i 2; | 13 | C | 110, 111 |
| | Sol i 3; | 24 | C | 110 |
| | Sol i 4; | 13 | C | 110 |
| *Solenopsis saevissima* (brazilian fire ant) | Sol s 2; | | | DR Hoffman |

| FOODS | | | | |
|---|---|---|---|---|
| *Gadus callarias* (cod) | Gad c 1; allergen M | 12 | C | 112, 113 |
| *Salmo salar* (Atlantic salmon) | Sal s 1; parvalbumin | 12 | C | X97824, X97825 |
| *Bos domesticus* (domestic cattle) | Bos d 4; alpha-lactalbumin | 14.2 | C | M18780 |
| | Bos d 5; beta-lactoglobulin | 18.3 | C | X14712 |
| | Bos d 6; serum albumin | 67 | C | M73993 |
| | Bos d 7; immunoglobulin | 160 | | 77 |
| | Bos d 8; caseins | 20-30 | | 77 |
| *Gallus domesticus* (chicken) | Gal d 1; ovomucoid | 28 | C | 114, 115 |
| | Gal d 2; ovalbumin | 44 | C | 114, 115 |
| | Gal d 3; conalbumin (Ag22) | 78 | C | 114, 115 |
| | Gal d 4; lysozyme | 14 | C | 114, 115 |
| | Gal d 5; serum albumin | 69 | C | X60688 |
| *Metapenaeus ensis* (shrimp) | Met e 1; tropomyosin | | C | U08008 |
| *Penaeus aztecus* (shrimp) | Pen a 1; tropomyosin | 36 | P | 116 |
| *Penaeus indicus* (shrimp) | Pen i 1; tropomyosin | 34 | C | 117 |
| *Todarodes pacificus* (squid) | Tod p 1; tropomyosin | 38 | P | 117A |
| *Haliotis Midae* (abalone) | Hal m 1 | 49 | — | 117B |
| *Apium graveolens* (celery) | Api g 1; Bet v 1 homologue | 16* | C | Z48967 |
| | Api g 4; profilin | | | AF129423 |
| | Api g 5; | 55/58 | P | P81943 |
| *Brassica juncea* (oriental mustard) | Bra j 1; 2S albumin | 14 | C | 118 |
| *Brassica rapa* (turnip) | Bra r 2; prohevein-like protein | 25 | ? | P81729 |
| *Hordeum vulgare* (barley) | Hor v 1; BMAI-1 | 15 | C | 119 |
| *Zea mays* (maize, corn) | Zea m 14; lipid transfer prot. | 9 | P | P19656 |
| *Corylus avellana* (hazelnut) | Cor a 1.0401; Bet v 1 homologue | 17 | C | AF136945 |
| *Malus domestica* (apple) | Mal d 1; Bet v 1 homologue | | C | X83672 |
| | Mal d 3; lipid transfer protein | 9 | C | Pastorello |
| *Pyrus communis* (pear) | Pyr c 1; Bet v 1 homologue | 18 | C | AF05730 |
| | Pyr c 4; profilin | 14 | C | AF129424 |
| | Pyr c 5; isoflavone reductase homologue | 33.5 | C | AF071477 |
| *Oryza sativa* (rice) | Ory s 1; | | C | U31771 |
| *Persea americana* (avocado) | Pers a 1; endochitinase | 32 | C | Z78202 |

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|
| *Prunus armeniaca* (apricot) | Pm ar 1; Bet v 1 homologue | | C | U93165 |
| | Pm ar 3; lipid transfer protein | 9 | P | |
| *Prunus avium* (sweet cherry) | Pm av 1; Bet v 1 homologue | | C | U66076 |
| | Pm av 2; thaumatin homologue | | C | U32440 |
| | Pru av 4; profilin | 15 | C | AF129425 |
| *Prunus persica* (peach) | Pm p 3; lipid transfer protein | 10 | P | P81402 |
| *Sinapis alba* (yellow mustard) | Sin a 1; 2S albumin | 14 | C | 120 |
| *Glycine max* (soybean) | Glym 1.0101; HPS | 7.5 | P | 121 |
| | Gly m 1.0102; HPS | 7 | P | 121 |
| | Gly m 2 | 8 | P | A57106 |
| | Gly m 3; profilin | 14 | C | AJ223982 |
| *Arachis hypogaea* (peanut) | Ara h 1; vicilin | 63.5 | C | L34402 |
| | Ara h 2; conglutin | 17 | C | L77197 |
| | Ara h 3; glycinin | 14 | C | AF093541 |
| | Ara h 4; glycinin | 37 | C | AF086821 |
| | Ara h 5; profilin | 15 | C | AF059616 |
| | Ara h 6; conglutin homolog | 15 | C | AF092846 |
| | Ara h 7; conglutin homolog | 15 | C | AF091737 |
| *Actinidia chinensis* (kiwi) | Act c 1; cysteine protease | 30 | P | P00785 |
| *Solanum tuberosum* (potato) | Sol t 1; patatin | 43 | P | P15476 |
| *Bertholletia excelsa* (Brazil nut) | Ber e 1; 2S albumin | 9 | C | P04403, M17146 |
| *Juglans regia* (English walnut) | Jug r 1; 2S albumin | 44 | C | U66866 |
| | Jug r 2; vicilin | | C | AF066055 |
| *Ricinus communis* (Castor bean) | Ric c 1; 2S albumin | | C | P01089 |
| OTHERS | | | | |
| *Anisakis simplex* (nematode) | Ani s 1 | 24 | P | A59069 |
| | Ani s 2; paramyosin | 97 | C | AF173004 |
| *Ascaris suum* (worm) | Asc s 1; | 10 | P | 122 |
| *Aedes aegyptii* (mosquito) | Aed a 1; apyrase | 68 | C | L12389 |
| | Aed a 2; | 37 | C | M33157 |
| *Hevea brasiliensis* (rubber) | Hev b 1; elongation factor | 58 | P | 123, 124 |
| | Hev b 2; (1,3-glucanase | 58 | P | 123, 124 |
| | Hev b 2; (1,3-glucanase | 34/36 | C | 125 |
| | Hev b 3 | 24 | P | 126, 127 |
| | Hev b 4; component of microhelix protein complex | 100/110/115 | P | 128 |
| | Hev b 5 | 16 | C | U42640 |
| | Hev b 6.01 hevein precursor | 20 | C | M36986/p02877 |
| | Hev b 6.02 hevein | 5 | C | M36986/p02877 |
| | Hev b 6.03 C-terminal fragment | 14 | C | M36986/p02877059 U80598 |
| | Hev b 7; patatin homologue | 46 | C | Y15042 |
| | Hev b 8; profilin | 14 | C | AJ132580/AJ1 |
| | Hev b 9; enolase | 51 | C | 32581 |
| | Hev b 10; Mn-superoxide dismut | 26 | C | AJ249148 |
| *Ctenocephalides felis felis* (cat flea) | Cte f 1; | — | — | — |
| | Cte f 2; M1b | 27 | C | AF231352 |
| *Homo sapiens* (human autoallergens) | Hom s 1; | 73* | C | Y14314 |
| | Hom s 2; | 10.3* | C | X80909 |
| | Hom s 3; | 20.1* | C | X89985 |
| | Homs 4; | 36* | C | Y17711 |
| | Homs 5; | 42.6* | C | P02538 |

1. Marsh, D.G., and L.R. Freidhoff. 1992. ALBE, an allergen database. IUIS, Baltimore, MD, Edition 1.0.
2. Marsh, D. G., L. Goodfriend, T. P. King, H. Lowenstein, and T. A. E. Platts-Mills. 1986. Allergen nomenclature. Bull WHO 64:767-770.
3. King, T.P., P.S. Norman, and J.T. Cornell. 1964. Isolation and characterization of allergen from ragweed pollen. II. Biochemistry 3:458-468.
4. Lowenstein, H. 1980. Timothy pollen allergens. Allergy 35:188-191.
5. Aukrust, L. 1980. Purification of allergens in Cladosporium herbarum. Allergy 35:206-207.
6. Demerec, M., E. A. Adelberg, A. J. Clark, and P. E. Hartman. 1966. A proposal for a uniform nomenclature in bacterial genetics. Genetics 54:61-75.
7. Bodmer, J. G., E. D. Albert, W. F. Bodmer, B. Dupont, H. A. Erlich, B. Mach, S. G. E. Marsh, W. R. Mayr, P. Parham, T. Sasuki, G. M. Th. Schreuder, J. L. Strominger, A. Svejgaard, and P. I. Terasaki. 1991. Nomenclature for factors of the HLA system, 1990. Immunogenetics 33:301-309.
8. Griffith, I.J., J. Pollock, D.G. Klapper, B.L. Rogers, and A.K. Nault. 1991. Sequence polymorphism of Amb a I and Amb a II, the major allergens in *Ambrosia artemisiifolia* (short ragweed). Int. Arch. Allergy Appl. Immunol. 96:296-304.
9. Roebber, M., D. G. Klapper, L. Goodfriend, W. B. Bias, S. H. Hsu, and D. G. Marsh. 1985. Immunochemical and genetic studies of Amb t V (RaSG), an Ra5 homologue from giant ragweed pollen. J. Immunol. 134:3062-3069.

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|

10. Metzler, W. J., K. Valentine, M. Roebber, M. Friedrichs, D. G. Marsh, and L. Mueller. 1992. Solution structures of ragweed allergen Amb t V. Biochemistry 31:5117-5127.
11. Metzler, W. J., K. Valentine, M. Roebber, D. G. Marsh, and L. Mueller. 1992. Proton resonance assignments and three-dimensional solution structure of the ragweed allergen Amb a V by nuclear magnetic resonance spectroscopy. Biochemistry 31:8697-8705.
12. Goodfriend, L., A.M. Choudhury, J. Del Carpio, and T.P. King. 1979. Cytochromes C: New ragweed pollen allergens. Fed. Proc. 38:1415.
13. Ekramoddoullah, A. K. M., F. T. Kisil, and A. H. Sehon. 1982. Allergenic cross reactivity of cytochrome c from Kentucky bluegrass and perennial ryegrass pollens. Mol. Immunol. 19:1527-1534.
14. Ansari, A. A., E. A. Killoran, and D. G. Marsh. 1987. An investigation of human response to perennial ryegrass (*Lolium perenne*) pollen cytochrome c (Lol p X). J. Allergy Clin. Immunol. 80:229-235.
15. Morgenstern, J.P., I.J. Griffith, A.W. Brauer, B.L. Rogers, J.F. Bond, M.D. Chapman, and M. Kuo. 1991. Amino acid sequence of Fel d I, the major allergen of the domestic cat: protein sequence analysis and cDNA cloning. Proc. Natl. Acad. Sci. USA 88:9690-9694.
16. Griffith, I.J., S. Craig, J. Pollock, X. Yu, J.P. Morgenstern, and B.L. Rogers. 1992. Expression and genomic structure of the genes encoding FdI, the major allergen from the domestic cat. Gene 113:263-268.
17. Weber, A., L. Marz, and F. Altmann. 1986. Characteristics of the asparagine-linked oligosaccharide from honey-bee venom phospholipase A2. Comp. Biochem. Physiol. 83B:321-324.
18. Weber, A., H. Schroder, K. Thalberg, and L. Marz. 1987. Specific interaction of IgE antibodies with a carbohydrate epitope of honey bee venom phospholipase A2. Allergy 42:464-470.
19. Stanworth, D. R., K. J. Dorrington, T. E. Hugh, K. Reid, and M. W. Turner. 1990. Nomenclature for synthetic peptides representative of immunoglobulin chain sequences. Bulletin WHO 68:109-111.
20. Rafnar, T., I. J. Griffith, M. C. Kuo, J. F. Bond, B. L. Rogers, and D.G. Klapper. 1991. Cloning of Amb a I (Antigen E), the major allergen family of short ragweed pollen. J. Biol. Chem. 266: 1229-1236.
21. Rogers, B.L., J.P. Morgenstern, I.J. Griffith, X.B. Yu, C.M. Counsell, A.W. Brauer, T.P. King, R.D. Garman, and M.C. Kuo. 1991. Complete sequence of the allergen Amb a II: recombinant expression and reactivity with T cells from ragweed allergic patients. J. Immunol. 147:2547-2552.
22. Klapper, D.G., L. Goodfriend, and J.D. Capra. 1980. Amino acid sequence of ragweed allergen Ra3. Biochemistry 19:5729-5734.
23. Ghosh, B., M.P. Perry, T. Rafnar, and D.G. Marsh. 1993. Cloning and expression of immunologically active recombinant Amb a V allergen of short ragweed (*Ambrosia artemisiifolia*) pollen. J. Immunol. 150:5391-5399.
24. Roebber, M., R. Hussain, D. G. Klapper, and D. G. Marsh. 1983. Isolation and properties of a new short ragweed pollen allergen, Ra6. J. Immunol. 131:706-711.
25. Lubahn, B., and D.G. Klapper. 1993. Cloning and characterization of ragweed allergen Amb a VI (abst). J. Allergy Clin. Immunol. 91:338.
26. Roebber, M., and D.G. Marsh. 1991. Isolation and characterization of allergen Amb a VII from short ragweed pollen. J. Allergy Clin. Immunol. 87:324.
27. Rogers, B.L., J. Pollock, D.G. Klapper, and I.J. Griffith. 1993. Cloning, complete sequence, and recombinant expression of a novel allergen from short ragweed pollen (abst). J. Allergy Clin. Immunol. 91:339.
28. Goodfriend, L., A.M. Choudhury, D.G. Klapper, K.M. Coulter, G. Dorval, J. DelCarpio, and C.K. Osterland. 1985. RaSG, a homologue of Ra5 in giant ragweed pollen: isolation, HLA-DR-associated activity and amino acid sequence. Mol. Immunol. 22:899-906.
28A. Breitenbach M, pers. comm.
29. Nilsen, B. M., K. Sletten, M. O'Neill, B. Smestead Paulsen, and H. van Halbeek. 1991. Structural analysis of the glycoprotein allergen Art v II from pollen of mugwort (*Artemesia vulgaris*). J. Biol. Chem. 266:2660-2668.
29A Jimenez A, Moreno C, Martinez J, Martinez A, Bartolome B, Guerra F, Palacios R 1994. Sensitization to sunflower pollen: only an occupational allergy? Int Arch Allergy Immunol 105:297-307.
30. Smith, P.M., Suphioglu, C., Griffith, I.J., Theriault, K., Knox, R.B. and Singh, M.B. 1996. Cloning and expression in yeast *Pichia pastoris* of a biologically active form of Cyn d 1, the major allergen of Bermuda grass pollen. J. Allergy Clin. Immuno 1. 98:331-343.
31. Suphioglu, C., Ferreira, F. and Knox, R.B. 1997. Molecular cloning and immunological characterisation of Cyn d 7, a novel calcium-binding allergen from Bermuda grass pollen. FEBS Lett. 402:167-172.
31a. Asturias JA, Arilla MC, Gomez-Bayon N, Martinez J, Martinez A, and Palacios R. 1997. Cloning and high level expression of *Cynodon dactylon* (Bermuda grass) pollen profilin (Cyn d 12) in *Escherichia coli*: purification and characterization of the allergen. Clin Exp Allergy 27:1307-1313.
32. Mecheri, S., G. Peltre, and B. David. 1985. Purification and characterization of a major allergen from *Dactylis glomerata* pollen: The Ag Dg 1. Int. Arch. Allergy Appl. Immunol. 78:283-289.
33. Roberts, A.M., L.J. Bevan, P.S. Flora, I. Jepson, and M.R. Walker. 1993. Nucleotide sequence of cDNA encoding the Group II allergen of Cocksfoot/Orchard grass (*Dactylis glomerata*), Dac g II. Allergy 48:615-623.
33a. Guerin-Marchand, C., Senechal, H., Bouin, A.P., Leduc-Brodard, V., Taudou, G., Weyer, A., Peltre, G. and David, B. 1996. Cloning, sequencing and immunological characterization of Dac g 3, a major allergen from *Dactylis glomerata* pollen. Mol. Immunol. 33:797-806.
34. Klysner, S., K. Welinder, H. Lowenstein, and F. Matthiesen. 1992. Group V allergens in grass pollen IV. Similarities in amino acid compositions and amino terminal sequences of the group V allergens from *Lolium perenne*, *Poa pratensis* and *Dactylis glomerata*. Clin. Exp. Allergy 22: 491-497.
35. Perez, M., G. Y. Ishioka, L. E. Walker, and R. W. Chesnut. 1990. cDNA cloning and immunological characterization of the rye grass allergen Lol p I. J. Biol. Chem. 265:16210-16215.
36. Griffith, I. J., P. M. Smith, J. Pollock, P. Theerakulpisut, A. Avjioglu, S. Davies, T. Hough, M. B. Singh, R. J. Simpson, L. D. Ward, and R. B. Knox. 1991. Cloning and sequencing of Lol p I, the major allergenic protein of rye-grass pollen. FEBS Letters 279:210-215.
37. Ansari, A. A., P. Shenbagamurthi, and D.G. Marsh. 1989. Complete amino acid sequence of a *Lolium perenne* (perennial rye grass) pollen allergen, Lol p II. J. Biol. Chem. 264:11181-11185.
37a. Sidoli, A., Tamborini, E., Giuntini, I., Levi, S., Volonte, G., Paini, C., De Lalla, C., Siccardi, A.G., Baralle, F.E., Galliani, S. and Arosio, P. 1993. Cloning, expression, and immunological characterization of recombinant *Lolium perenne* allergen Lol p II. J. Biol. Chem. 268:21819-21825.
38. Ansari, A. A., P. Shenbagamurthi, and D. G. Marsh. 1989. Complete primary structure of a *Lolium perenne* (perennial rye grass) pollen allergen, Lol p III: Comparison with known Lol p I and II sequences. Biochemistry 28:8665-8670.
39. Singh, M. B., T. Hough, P. Theerakulpisut, A. Avjioglu, S. Davies, P. M. Smith, P. Taylor, R. J. Simpson, L. D. Ward, J. McCluskey, R. Puy, and R.B. Knox. 1991. Isolation of cDNA encoding a newly identified major allergenic protein of rye-grass pollen: Intracellular targeting to the amyloplost. Proc. Natl. Acad. Sci. 88:1384-1388.
39a. van Ree R, Hoffman DR, van Dijk W, Brodard V, Mahieu K, Koeleman CA, Grande M, van Leeuwen WA, Aalberse RC. 1995. Lol p XI, a new major grass pollen allergen, is a member of a family of soybean trypsin inhibitor-related proteins. J Allergy Clin Immunol 95:970-978.
40. Suphioglu, C. and Singh, M.B. 1995. Cloning, sequencing and expression in *Escherichia coli* of Pha a 1 and four isoforms of Pha a 5, the major allergens of canary grass pollen. Clin. Exp. Allergy 25:853-865.
41. Dolecek, C., Vrtala, S., Laffer, S., Steinberger, P., Kraft, D., Scheiner, O. and Valenta, R. 1993. Molecular characterization of Phl p II, a major timothy grass (*Phleum pratense*) pollen allergen. FEBS Lett. 335:299-304.
41A. Fischer S, Grote M, Fahlbusch B, Muller WD, Kraft D, Valenta R. 1996. Characterization of Phl p 4, a major timothy grass (*Phleum pratense*) pollen allergen. J Allergy Clin Immunol 98:189-198.
42. Matthiesen, F., and H. Lowenstein. 1991. Group V allergens in grass pollens. I. Purification and characterization of the group V allergen from *Phleum pratense* pollen, Phl p V. Clin. Exp. Allergy 21:297-307.
43. Petersen, A., Bufe, A., Schramm, G., Schlaak, M. and Becker, W.M. 1995. Characterization of the allergen group VI in timothy grass pollen (Phl p 6). II. cDNA cloning of Phl p 6 and structural comparison to grass group V. Int. Arch. Allergy Immunol. 108:55-59.
44. Valenta, R., Ball, T., Vrtala, S., Duchene, M., Kraft, D. and Scheiner, O. 1994. cDNA cloning and expression of timothy grass (*Phleum pratense*) pollen profilin in *Escherichia coli*: comparison with birch pollen profilin. Biochem. Biophys. Res. Commun. 199:106-118.
46. Esch, R. E., and D. G. Klapper. 1989. Isolation and characterization of a major cross-reactive grass group I allergenic determinant. Mol. Immunol. 26:557-561.
47. Olsen, E., L. Zhang, R. D. Hill, F. T. Kisil, A. H. Sehon, and S. Mohapatra. 1991. Identification and characterization of the Poa p IX group of basic allergens of Kentucky bluegrass pollen. J. Immunol. 147:205-211.

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|

48. Avjioglu, A., M. Singh, and R.B. Knox. 1993. Sequence analysis of Sor h I, the group I allergen of Johnson grass pollen and it comparison to rye-grass Lol p I (abst). J. Allergy Clin. Immunol. 91:340.
51. Larsen, J.N., P. Strºman, and H. Ipsen. 1992. PCR based cloning and sequencing of isogenes encoding the tree pollen major allergen Car b I from *Carpinus betulus*, hornbeam. Mol. Immunol. 29:703-711.
52. Kos T, Hoffmann-Sommergruber K, Ferreira F, Hirschwehr R, Ahorn H, Horak F, Jager S, Sperr W, Kraft D, Scheiner 0. 1993. Purification, characterization and N-terminal amino acid sequence of a new major allergen from European chestnut pollen--Cas s 1. Biochem Biophys Res Commun 196:1086-92.
53. Breiteneder, H., F. Ferreira, K. Hoffman-Sommergruber, C. Ebner, M. Breitenbach, H. Rumpold, D. Kraft, and 0. Scheiner. 1993. Four recombinant isoforms of Cor a I, the major allergen of hazel pollen. Europ. J. Biochem. 212:355-362.
54. Ipsen, H., and B.C. Hansen. 1991. The NH2-terminal amino acid sequence of the immunochemically partial identical major allergens of alder (*Alnus glutinosa*) Aln g I, birch (*Betula verrucosa*) Bet v I, hornbeam (*Carpinus betulus*) Car b I and oak (*Quercus alba*) Que a I pollens. Mol. Immunol. 28:1279-1288.
55. Taniai, M., S. Ando, M. Usui, M. Kurimoto, M. Sakaguchi, S. Inouye, and T. Matuhasi. 1988. N-terminal amino acid sequence of a major allergen of Japanese cedar pollen (Cry j I). FEBS Lett. 239:329-332.
56. Griffith, I.J., A. Lussier, R. Garman, R. Koury, H. Yeung, and J. Pollock. 1993. The cDNA cloning of Cry j I, the major allergen of *Cryptomeria japonica* (Japanese cedar) (abst). J. Allergy Clin. Immunol. 91:339.
57. Sakaguchi, M., S. Inouye, M. Taniai, S. Ando, M. Usui, and T. Matuhasi. 1990. Identification of the second major allergen of Japanese cedar pollen. Allergy 45:309-312.
58 Gross GN, Zimburean JM, Capra JD 1978. Isolation and partial characterization of the allergen in mountain cedar pollen. Scand J Immunol 8:437-41
58A Obispo TM, Melero JA, Carpizo JA, Carreira J, Lombardero M 1993. The main allergen of Olea europaea (Ole e I) is also present in other species of the oleaceae family. Clin Exp Allergy 23:311-316.
59. Cardaba, B., D. Hernandez, E. Martin, B. de Andres, V. del Pozo, S. Gallardo, J.C. Fernandez, R. Rodriguez, M. Villalba, P. Palomino, A. Basomba, and C. Lahoz. 1993. Antibody response to olive pollen antigens: association between HLA class II genes and IgE response to Ole e I (abst). J. Allergy Clin. Immunol. 91:338.
60. Villalba, M., E. Batanero, C. Lopez-Otin, L.M. Sanchez, R.I. Monsalve, M.A. Gonzalez de la Pena, C. Lahoz, and R. Rodriguez. 1993. Amino acid sequence of Ole e I, the major allergen from olive tree pollen (*Olea europaea*). Europ.J. Biochem. 216:863-869.
60A. Asturias JA, Arilla MC, Gomez-Bayon N, Martinez J, Martinez A, Palacios R 1997. Cloning and expression of the panallergen profilin and the major allergen (Ole e 1) from olive tree pollen. J Allergy Clin Immunol 100:365-372.
60B. Batanero E, Villalba M, Ledesma A Puente XS, Rodriguez R. 1996. Ole e 3, an olive-tree allergen, belongs to a widespread family of pollen proteins. Eur J Biochem 241: 772-778.
61. Chua, K. Y., G. A. Stewart, and W. R. Thomas. 1988. Sequence analysis of cDNA encoding for a major house dust mite allergen, Der p I. J. Exp. Med. 167:175-182.
62. Chua, K. Y., C. R. Doyle, R. J. Simpson, K. J. Turner, G. A. Stewart, and W. R. Thomas. 1990. Isolation of cDNA coding for the major mite allergen Der p II by IgE plaque immunoassay. Int. Arch. Allergy Appl. Immunol. 91:118-123.
63. Smith WA, Thomas WR. 1996. Comparative analysis of the genes encoding group 3 allergens from *Dermatophagoides pteronyssinus* and *Dermatophagoides farinae*. Int Arch Allergy Immunol 109: 133-40.
64. Lake, F.R., L.D. Ward, R.J. Simpson, P.J. Thompson, and G.A. Stewart. 1991. House dust mite-derived amylase: Allergenicity and physicochemical characterisation. J. Allergy Clin. Immunol. 87:1035-1042.
65. Tovey, E. R., M. C. Johnson, A. L. Roche, G. S. Cobon, and B. A. Baldo. 1989. Cloning and sequencing of a cDNA expressing a recombinant house dust mite protein that binds human IgE and corresponds to an important low molecular weight allergen. J. Exp. Med. 170:1457-1462.
66. Yasueda, H., T. Shida, T. Ando, S. Sugiyama, and H. Yamakawa. 1991. Allergenic and proteolytic properties of fourth allergens from Dermatophagoides mites. In: "Dust Mite Allergens and Asthma. Report of the 2nd international workshop" A. Todt, Ed., UCB Institute of Allergy, Brussels, Belgium, pp. 63-64.
67. Shen, H.-D., K.-Y. Chua, K.-L. Lin, K.-H. Hsieh, and W.R. Thomas. 1993. Molecular cloning of a house dust mite allergen with common antibody binding specificities with multiple components in mite extracts. Clin. Exp. Allergy 23:934-40.
67A. O'Neil GM, Donovan GR, Baldo BA. 1994. Cloning and charaterisation of a major allergen of the house dust mite *Dermatophagoides pteronyssinus*, homologous with glutathione 5-transferase. Biochim Biophys Acta,1219:521-528.
67B. King C, Simpson RJ, Moritz RL, Reed GE, Thompson PJ, Stewart GA. 1996. The isolation and characterization of a novel collagenolytic serine protease allergen (Der p 9) from the dust mite *Dermatophagoides pteronyssinus*. J Allergy Clin Immunol 98:739-47.
68. Lind P, Hansen OC, Horn N. 1988. The binding of mouse hybridoma and human IgE antibodies to the major fecal allergen, Der p I of D. pteronyssinus. J. Immunol. 140:4256-4262.
69. Dilworth, R. J., K. Y. Chua, and W. R. Thomas. 1991. Sequence analysis of cDNA coding for a mojor house dust allergn Der f I. Clin. Exp. Allergy 21:25-32.
70. Nishiyama, C., T. Yunki, T. Takai, Y. Okumura, and H. Okudaira. 1993. Determination of three disulfide bonds in a major house dust mite allergen, Der f II. Int. Arch. Allergy Immunol. 101:159-166.
71. Trudinger, M., K. Y. Chua, and W. R. Thomas. 1991. cDNA encoding the major dust mite allergen Der f II. Clin. Exp. Allergy 21:33-38.
72. Aki T, Kodama T, Fujikawa A, Miura K, Shigeta S, Wada T, Jyo T, Murooka Y, Oka S, Ono K. 1995. Immunochemical characteristion of recombinant and native tropomyosins as a new allergen from the house dust mite *Dermatophagoides farinae*. J Allergy Clin Immunol 96:74-83.
73. van Hage-Hamsten, M., T. Bergman, E Johansson, B. Persson, H. Jornvall, B. Harfast, and S.G.O. Johansson. 1993. N-terminal amino acid sequence of major allergen of the mite lepidoglyphus destructor (abst). J. Allergy Clin. Immunol. 91:353.
74. Varela J, Ventas P, Carreira J, Barbas JA, Gimenez-Gallego G, Polo F. Primary structure of Lep d I, the main *Lepidoglyphus destructor* allergen. Eur J Biochem 225:93-98, 1994.
75. Schmidt M, van der Ploeg I, Olsson S, van Hage Hamsten M. The complete cDNA encoding the *Lepidoglyphus destructor* major allergen Lep d 1. FEBS Lett 370:11-14, 1995.
76. Rautiainen J, Rytkonen M, Pelkonen J, Pentikainen J, Perola O, Virtanen T, Zeiler T, Mantyjarvi R. BDA20, a major bovine dander allergen characterized at the sequence level is Bos d 2. Submitted.
77. Gjesing B, Lowenstein H. Immunochemistry of food antigens. Ann Allergy 53:602, 1984.
78. de Groot, H., K.G.H. Goei, P. van Swieten, and R.C. Aalberse. 1991 Affinity purification of a major and a minor allergen from dog extract: Serologic activity of affiity-purified Can f I and Can f I-depleted extract. J. Allergy Clin. Immunol. 87:1056-1065.
79. Konieczny, A. Personal communication; Immunologic Pharmaceutical Corp.
79A. Bulone, V. 1998. Separation of horse dander allergen proteins by two-dimensional electrophoresis. Molecular characterisation and identification of Equ c 2.0101 and Equ c 2.0102 as lipocalin proteins. Eur J Biochem 253:202-211.
79B. Swiss-Prot acc. P81216, P81217.
80. McDonald, B., M. C. Kuo, J. L. Ohman, and L. J. Rosenwasser. 1988. A 29 amino acid peptide derived from rat alpha 2 euglobulin triggers murine allergen specific human T cells (abst). J. Allergy Clin. Immunol. 83:251.
81. Clarke, A. J., P. M. Cissold, R. A. Shawi, P. Beattie, and J. Bishop. 1984. Structure of mouse urinary protein genes: differential splicing configurations in the 3'-non-coding region. EMBO J 3:1045-1052.
82. Longbottom, J. L. 1983. Chracterization of allergens from the urines of experimental animals. McMillan Press, London, pp. 525-529.
83. Laperche, Y., K. R. Lynch, K. P. Dolans, and P. Feigelsen. 1983. Tissue-specific control of alpha 2u globulin gene expression: constitutive synthesis in submaxillary gland. Cell 32:453-460.
83A. Aukrust L, Borch SM. 1979. Partial purification and characterization of two *Cladosporium herbarum* allergens. Int Arch Allergy Appl Immunol 60:68-79.
83B. Sward-Nordmo M, Paulsen BS, Wold JK. 1988. The glycoprotein allergen Ag-54 (Cla h II) from *Cladosporium herbarum*. Structural studies of the carbohydrate moiety. Int Arch Allergy Appl Immunol 85:288-294.
84. Shen, et al. J. Allergy Clin. Immunol. 103:S157, 1999.
84A. Crameri R. Epidemiology and molecular basis of the involvement of *Aspergillus fumigatus* in allergic diseases. Contrib. Microbiol. Vol. 2, Karger, Basel (in press).
84B. Shen, et al. (manuscript submitted), 1999
84C. Shen HD, Ling WL, Tan MF, Wang SR, Chou H, Han SIH. Vacuolar serine proteinase: A major allergen of *Aspergillus fumigatus*. 10th International Congress of Immunology, Abstract, 1998.
85. Kumar, A., L.V. Reddy, A. Sochanik, and V.P. Kurup. 1993. Isolation and characterization of a recombinant heat shock protein of *Aspergillus fumigatus*. J. Allergy Clin. Immunol. 91:1024-1030.

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|

86. Teshima, R., H. Ikebuchi, J. Sawada, S. Miyachi, S. Kitani, M. Iwama, M. Irie, M. Ichinoe, and T. Terao. 1993. Isolation and characterization of a major allergenic component (gp55) of *Aspergillus fumigatus*. J. Allergy Clin. Immunol. 92:698-706.

86A. Shen HD, Lin WL, Tsai JJ, Liaw SF, Han SH. 1996. Allergenic components in three different species of *Penicillium*: crossreactivity among major allergens. Clin Exp Allergy 26:444-451.

86B. Shen, et al. Abstract; The XVIII Congress of the European Academy of Allergology and Clinical Immunology, Brussels, Belgium, Jul. 3-7, 1999.

87. Shen HD, Liaw SF, Lin WL, Ro LH, Yang HL, Han SH. 1995. Molecular cloning of cDNA coding for the 68 kDa allergen of *Penicillium notatum* using MoAbs. Clin Exp Allergy 25:350-356.

88. Shen, H.D., K.B. Choo, H.H. Lee, J.C. Hsieh, and S.H. Han. 1991. The 40 kd allergen of *Candida albicans* is an alcohol dehydrogenase: molecular cloning and immunological analysis using monoclonal antibodies. Clin. Exp. Allergy 21:675-681.

89. Shen, et al. Clin. Exp. Allergy (in press), 1999.

90. Woodfolk JA, Wheatley LM, Piyasena RV, Benjamin DC, Platts-Mills TA.1998. Trichophyton antigens associated with IgE antibodies and delayed type hypersensitivity. Sequence homology to two families of serine proteinases. J Biol Chem 273:29489-96.

91. Deuell, B., L.K. Arruda, M.L. Hayden, M.D. Chapman and T.A.E. Platts-Mills. 1991. *Trichophyton tonsurans* Allergen I. J. Immunol. 147:96-101.

91A. Schmidt M, Zargari A, Holt P, Lindbom L, Hellman U, Whitley P, van der Ploeg I, Harfast B, Scheynius A. 1997. The complete cDNA sequence and expression of the first major allergenic protein of *Malassezia furfur*, Mal f 1. Eur J Biochem 246:181-185.

91B. Homer WE, Reese G, Lehrer SB. 1995. Identification of the allergen Psi c 2 from the basidiomycete *Psilocybe cubensis* as a fungal cyclophilin. Int Arch Allergy Immunol 107:298-300.

92. Kuchler, K., M. Gmachl, M. J. Sippl, and G. Kreil. 1989. Analysis of the cDNA for phospholipase A2 from honey bee venom glands: The deduced amino acid sequence reveals homology to the corresponding vertebrate enzymes. Eur. J. Biochem. 184:249-254.

93. Gmachl, M., and G. Kreil. 1993. Bee venom hyaluronidase is homologous to a membrane protein of mammalian sperm. Proc. Natl. Acad. Sci. USA 90:3569-3573.

94. Habermann, E. 1972. Bee and wasp venoms. Science 177:314-322.

95. Jacobson, R.S., and D.R. Hoffman. 1993. Characterization of bumblebee venom allergens (abst). J. Allergy Clin. Immunol. 91:187.

96. Arruda LK, Vailes LD, Mann BJ, Shannon J, Fox JW, Vedvick TS, Hayden ML, Chapman MD. Molecular cloning of a major cockroach (*Blattella germanica*) allergen, Bla g 2. Sequence homology to the aspartic proteases. J Biol Chem 270:19563-19568, 1995.

97. Arruda LK, Vailes LD, Hayden ML, Benjamin DC, Chapman MD. Cloning of cockroach allergen, Bla g 4, identifies ligand binding proteins (or calycins) as a cause of IgE antibody responses. J Biol Chem 270:31196-31201, 1995.

98. Arruda LK, Vailes LD, Benjamin DC, Chapman MD. Molecular cloning of German Cockroach (*Blattella germanica*) allergens. Int Arch Allergy Immunol 107:295-297, 1995.

98A. Wu CH, Lee MF, Liao SC. 1995. Isolation and preliminary characterization of cDNA encoding American cockroach allergens. J Allergy Clin Immunol 96: 352-9.

99. Mazur, G., X. Baur, and V. Liebers. 1990. Hypersensitivity to hemoglobins of the Diptera family Chironomidae: Structural and functional studies of their immunogenic/allergenic sites. Monog. Allergy 28:121-137.

100. Soldatova, L., L. Kochoumian, and T.P. King. 1993. Sequence similarity of a hornet (*D. maculata*) venom allergen phospholipase A1 with mammalian lipases. FEBS Letters 320:145-149.

101. Lu, G., L. Kochoumian and T.P. King. Whiteface hornet venom allergen hyaluronidase: cloning and its sequence similarity with other proteins (abst.). 1994. J. Allergy Clin. Immunol. 93:224.

102. Fang, K. S. F., M. Vitale, P. Fehlner, and T. P. King. 1988. cDNA cloning and primary structure of a white-faced hornet venom allergen, antigen 5. Proc. Natl. Acad. Sci., USA 85:895-899.

103. King, T. P., D. C. Moran, D. F. Wang, L. Kochoumian, and B.T. Chait. 1990. Structural studies of a hornet venom allergen antigen 5, Dol m V and its sequence similarity with other proteins. Prot. Seq. Data Anal. 3:263-266.

104. Lu, G., M. Villalba, M.R. Coscia, D.R. Hoffman, and T.P. King. 1993. Sequence analysis and antigen cross reactivity of a venom allergen antigen 5 from hornets, wasps and yellowjackets. J. Immunol. 150: 2823-2830.

105. King, T. P. and Lu, G. 1997. Unpublished data.

105A. King TP, Lu G, Gonzalez M, Qian N and Soldatova L. 1996. Yellow jacket venom allergens, hyaluronidase and phospholipase: sequence similarity and antigenic cross-reactivity with their hornet and wasp homologs and possible implications for clinical allergy. J. Allergy Clin. Immunol. 98:588-600.

106. Hoffman, D.R. 1993. Allergens in hymenoptera venom XXV: The amino acid sequences of antigen 5 molecules and the structural basis of antigenic cross-reactivity. J. Allergy Clin. Immunol. 92:707-716.

107. Hoffman, D.R. 1992. Unpublished data.

108. Hoffman, D. R. 1993. The complete amino acid sequence of a yellowjacket venom phospholipase (abst). J. Allergy Clin. Immunol. 91:187.

109. Jacobson, R.S., D.R. Hoffman, and D.M. Kemeny. 1992. The cross-reactivity between bee and vespid hyaluronidases has a structural basis (abst). J. Allergy Clin. Immunol. 89:292.

110. Hoffman, D.R. 1993. Allergens in Hymenoptera venom XXIV: The amino acid sequences of imported fire ant venom allergens Sol i II, Sol i III, and Sol i IV. J. Allergy Clin. Immunol. 91:71-78.

111. Schmidt, M., R.B. Walker, D.R. Hoffman, and T.J. McConnell. 1993. Nucleotide sequence of cDNA encoding the fire ant venom protein Sol i II. FEBS Letters 319:138-140.

112. Elsayed S, Bennich H. The primary structure of Allergen M from cod. Scand J Immunol 3:683-686, 1974.

113. Elsayed S, Aas K, Sletten K, Johansson SGO. Tryptic cleavage of a homogeneous cod fish allergen and isolation of two active polypeptide fragments. Immunochemistry 9:647-661, 1972.

114. Hoffman, D. R. 1983. Immunochemical identification of the allergens in egg white. J. Allergy Clin. Immunol. 71:481-486.

115. Langeland, T. 1983. A clinical and immunological study of allergy to hen's egg white. IV. specific IgE antibodies to individual allergens in hen's egg white related to clinical and immunolgical parameters in egg-allergic patients. Allergy 38:493-500.

116. Daul, C.B., M. Slattery, J.E. Morgan, and S.B. Lehrer. 1993. Common crustacea allergens: identification of B cell epitopes with the shrimp specific monoclonal antibodies. In: "Molecular Biology and Immunology of Allergens" (D. Kraft and A. Sehon, eds.). CRC Press, Boca Raton. pp. 291-293.

117. K.N. Shanti, B.M. Martin, S. Nagpal, D.D. Metcalfe, P.V. Subba Rao. 1993. Identification of tropomyosin as the major shrimp allergen and characterization of its IgE-binding epitopes. J. Immunol. 151:5354-5363.

117A. M. Miyazawa, H. Fukamachi, Y. Inagaki, G. Reese, C.B. Daul, S.B. Lehrer, S. Inouye, M. Sakaguchi. 1996. Identification of the first major allergen of a squid (*Todarodes pacificus*). J. Allergy Clin. Immunol. 98:948-953.

117B A. Lopata et al. 1997. Characteristics of hypersensitivity reactions and identification of a uniques 49 kDa IgE binding protein (Hal-m-1) in Abalone (*Haliotis midae*). J.Allergy Clin. Immunol. Submitted 118. Monsalve, RI., M.A. Gonzalez de la Pena, L. Menendez-Arias, C. Lopez-Otin, M. Villalba, and R. Rodriguez. 1993. Characterization of a new mustard allergen, Bra j IE. Detection of an allergenic epitope. Biochem. J. 293:625-632.

119. Mena, M., R. Sanchez-Monge, L. Gomez, G. Salcedo, and P. Carbonero. 1992. A major barley allergen associated with baker's asthma disease is a glycosylated monomeric inhibitor of insect alpha-amylase: cDNA cloning and chromosomal location of the gene. Plant Molec. Biol. 20:451-458.

120. Menendez-Arias, L., I. Moneo, J. Dominguez, and R. Rodriguez. 1988. Primary structure of the major allergen of yellow mustard (*Sinapis alba* L.) seed, Sin a I. Eur. J. Biochem. 177:159-166.

121. Gonzalez R, Varela J, Carreira J, Polo F. Soybean hydrophobic protein and soybean hull allergy. Lancet 346:48-49, 1995.

122. Christie, J. F., B. Dunbar, I. Davidson, and M. W. Kennedy. 1990. N-terminal amino acid sequence identity between a major allergen of *Ascaris lumbricoides* and *Ascaris suum* and MHC-restricted IgE responses to it. Immunology 69:596-602.

123. Czuppon AB, Chen Z, Rennert S, Engelke T, Meyer HE, Heber M, Baur X. The rubber elongation factor of rubber trees (*Hevea brasiliensis*) is the major allergen in latex. J Allergy Clin Immunol 92:690-697, 1993.

124. Attanayaka DPSTG, Kekwick RGO, Franklin FCH. 1991. Molecular cloning and nucleotide sequencing of the rubber elongation factor gene from hevea brasiliensis. Plant Mol Biol 16:1079-1081.

125. Chye ML, Cheung KY. 1995. ( 1,3-glucanase is highly expressed in Laticifers of *Hevea brasiliensis*. Plant Mol Biol 26:397-402.

126. Alenius H, Palosuo T, Kelly K, Kurup V, Reunala T, Makinen-Kiljunen S, Turjanmaa K Fink J. 1993. IgE reactivity to 14-kD and 27-kD natural rubber proteins in Latex-allergic children with *Spina bifida* and other congenital anomalies. Int Arch Allergy Immunol 102:61-66.

APPENDIX A-continued

| ALLERGEN SOURCE | SYSTEMATIC AND ORIGINAL NAMES | MW KDA | SEQ | ACCESSION NO. OR REFERENCES |
|---|---|---|---|---|

127. Yeang HY, Cheong KF, Sunderasan E, Hamzah S, Chew NP, Hamid S, Hamilton RG, Cardosa MJ. 1996. The 14.6 kD (REF, Hey b 1) and 24 kD (Hey b 3) rubber particle proteins are recognized by IgE from Spina Bifida patients with Latex allergy. J Allerg Clin Immunol in press.
128. Sunderasan E, Hamzah S, Hamid S, Ward MA, Yeang HY, Cardosa MJ. 1995. Latex B-serum (−1,3-glucanase (Hey b 2) and a component of the microhelix (Hey b 4) are major Latex allergens. J nat Rubb Res 10:82-99.

We claim:

1. A composition comprising:
   (a) dead *E. coli* cells that have expressed and encapsulated therein a non-secreted, recombinant version of an allergen protein; and
   (b) a pharmaceutically acceptable carrier appropriate for mucosal delivery,
   the composition being formulated for mucosal delivery.

2. The composition of claim 1, wherein mucosal delivery is selected from the group consisting of rectal, vaginal, nasal, oral, and buccal administration.

* * * * *

SEQUENCE LISTING

<160> NUMBER OF SEQ ID NOS: 81

<210> SEQ ID NO 1
<211> LENGTH: 2032
<212> TYPE: DNA
<213> ORGANISM: Arachis hypogaea

<400> SEQUENCE: 1

```
aataatcata tatattcatc aatcatctat ataagtagta gcaggagcaa tgagagggag      60
ggtttctcca ctgatgctgt tgctagggat ccttgtcctg gcttcagttt ctgcaacgca     120
tgccaagtca tcaccttacc agaagaaaac agagaacccc tgcgcccaga ggtgcctcca     180
gagttgtcaa caggaaccgg atgacttgaa gcaaaaggca tgcgagtctc gctgcaccaa     240
gctcgagtat gatcctcgtt gtgtctatga tcctcgagga cacactgca ccaccaacca      300 acgttcccct ccaggggagc ggacacgtgg ccgccaaccc ggagactacg atgatgaccg     360
ccgtcaaccc cgaagagagg aaggaggccg atgggacca gctggaccga gggagcgtga     420
aagagaagaa gactggagac aaccaagaga agattggagg cgaccaagtc atcagcagcc     480
acggaaaata aggcccgaag gaagagaagg agaacaagag tggggaacac caggtagcca     540
tgtgagggaa gaaacatctc ggaacaaccc tttctacttc ccgtcaaggc ggtttagcac     600
ccgctacggg aaccaaaacg gtaggatccg ggtcctgcag aggtttgacc aaaggtcaag     660
gcagtttcag aatctccaga atcaccgtat tgtgcagatc gaggccaaac ctaacactct     720
tgttcttccc aagcacgctg atgctgataa catccttgtt atccagcaag ggcaagccac     780
cgtgaccgta gcaaatggca ataacagaaa gagctttaat cttgacgagg ccatgcact     840 cagaatccca tccggtttca tttcctacat cttgaaccgc catgacaacc agaacctcag     900
agtagctaaa atctccatgc ccgttaacac acccggccag tttgaggatt tcttcccggc     960
gagcagccga gaccaatcat cctacttgca gggcttcagc aggaatacgt tggaggccgc    1020
cttcaatgcg gaattcaatg agatacggag ggtgctgtta gaagagaatg caggaggtga    1080
gcaagaggag agagggcaga ggcgatggag tactcggagt agtgagaaca atgaaggagt    1140
gatagtcaaa gtgtcaaagg agcacgttga agaacttact aagcacgcta aatccgtctc    1200
aaagaaaggc tccgaagaag agggagatat caccaaccca atcaacttga gagaaggcga    1260
gcccgatctt tctaacaact tgggaagtt atttgaggtg aagccagaca agaagaaccc    1320
ccagcttcag gacctggaca tgatgctcac ctgtgtagag atcaaagaag gagctttgat    1380
gctcccacac ttcaactcaa aggccatggt tatcgtcgtc gtcaacaaag gaactggaaa    1440
ccttgaactc gtggctgtaa gaaaagagca acaacagagg ggacggcggg aagaagagga    1500
ggacgaagac gaagaagagg agggaagtaa cagagaggtg cgtaggtaca cagcgaggtt    1560
gaaggaaggc gatgtgttca tcatgccagc agctcatcca gtagccatca acgcttcctc    1620
cgaactccat ctgcttggct tcggtatcaa cgctgaaaac aaccacagaa tcttccttgc    1680
aggtgataag gacaatgtga tagaccagat agagaagcaa gcgaaggatt tagcattccc    1740
```

```
tgggtcgggt gaacaagttg agaagctcat caaaaaccag aaggaatctc actttgtgag    1800
tgctcgtcct caatctcaat ctcaatctcc gtcgtctcct gagaaagagt ctcctgagaa    1860
agaggatcaa gaggaggaaa accaaggagg gaagggtcca ctcctttcaa ttttgaaggc    1920
ttttaactga gaatggaggc aacttgttat gtatcgataa taagatcacg cttttgtact    1980
ctactatcca aaacttatc aataaataaa acgtttgtg cgttgtttct cc              2032
```

<210> SEQ ID NO 2
<211> LENGTH: 626
<212> TYPE: PRT
<213> ORGANISM: Arachis hypogaea

<400> SEQUENCE: 2

```
Met Arg Gly Arg Val Ser Pro Leu Met Leu Leu Gly Ile Leu Val
1               5                   10                  15

Leu Ala Ser Val Ser Ala Thr His Ala Lys Ser Pro Tyr Gln Lys
                20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
290                 295                 300

Ser Ser Arg Asp Gln Ser Ser Tyr Leu Gln Gly Phe Ser Arg Asn Thr
305                 310                 315                 320
```

-continued

| | | | | | | | | | | | |
|---|---|---|---|---|---|---|---|---|---|---|---|
|Leu|Glu|Ala|Ala|Phe|Asn|Ala|Glu|Phe|Asn|Glu|Ile|Arg|Arg|Val|Leu|
| | | | |325| | | |330| | | |335| | | |

Leu Glu Glu Asn Ala Gly Gly Glu Gln Glu Glu Arg Gly Gln Arg Arg
                340                        345                        350

Trp Ser Thr Arg Ser Ser Glu Asn Asn Glu Gly Val Ile Val Lys Val
                355                        360                        365

Ser Lys Glu His Val Glu Leu Thr Lys His Ala Lys Ser Val Ser
    370                        375                    380

Lys Lys Gly Ser Glu Glu Gly Asp Ile Thr Asn Pro Ile Asn Leu
385                        390                        395                    400

Arg Glu Gly Glu Pro Asp Leu Ser Asn Asn Phe Gly Lys Leu Phe Glu
                405                        410                        415

Val Lys Pro Asp Lys Lys Asn Pro Gln Leu Gln Asp Leu Asp Met Met
                420                        425                        430

Leu Thr Cys Val Glu Ile Lys Glu Gly Ala Leu Met Leu Pro His Phe
                435                        440                        445

Asn Ser Lys Ala Met Val Ile Val Val Asn Lys Gly Thr Gly Asn
    450                        455                    460

Leu Glu Leu Val Ala Val Arg Lys Glu Gln Gln Gln Arg Gly Arg Arg
465                        470                        475                    480

Glu Glu Glu Glu Asp Glu Asp Glu Glu Glu Gly Ser Asn Arg Glu
                    485                        490                        495

Val Arg Arg Tyr Thr Ala Arg Leu Lys Glu Gly Asp Val Phe Ile Met
                500                        505                        510

Pro Ala Ala His Pro Val Ala Ile Asn Ala Ser Ser Glu Leu His Leu
                515                        520                        525

Leu Gly Phe Gly Ile Asn Ala Glu Asn Asn His Arg Ile Phe Leu Ala
                530                        535                        540

Gly Asp Lys Asp Asn Val Ile Asp Gln Ile Glu Lys Gln Ala Lys Asp
545                        550                        555                    560

Leu Ala Phe Pro Gly Ser Gly Glu Gln Val Glu Lys Leu Ile Lys Asn
                565                        570                        575

Gln Lys Glu Ser His Phe Val Ser Ala Arg Pro Gln Ser Gln Ser Gln
                580                        585                        590

Ser Pro Ser Ser Pro Glu Lys Glu Ser Pro Glu Lys Glu Asp Gln Glu
                595                        600                        605

Glu Glu Asn Gln Gly Gly Lys Gly Pro Leu Leu Ser Ile Leu Lys Ala
                610                        615                        620

Phe Asn
625

<210> SEQ ID NO 3
<211> LENGTH: 474
<212> TYPE: DNA
<213> ORGANISM: Arachis hypogaea

<400> SEQUENCE: 3

```
ctcaccatac tagtagccct cgccctttc  ctcctcgctg cccacgcatc tgcgaggcag      60
cagtgggaac tccaaggaga cagaagatgc cagagccagc tcgagagggc gaacctgagg     120
ccctgcgagc aacatctcat gcagaagatc aacgtgacg  aggattcata tgaacgggac     180
ccgtacagcc ctagtcagga tccgtacagc cctagtccat atgatcggag aggcgctgga     240
tcctctcagc accaagagag gtgttgcaat gagctgaacg agtttgagaa caaccaaagg     300
tgcatgtgcg aggcattgca acagatcatg gagaaccaga gcgataggtt gcaggggagg     360
```

```
caacaggagc aacagttcaa gagggagctc aggaacttgc ctcaacagtg cggccttagg    420
gcaccacagc gttgcgactt ggacgtcgaa agtggcggca gagacagata ctaa          474
```

<210> SEQ ID NO 4
<211> LENGTH: 157
<212> TYPE: PRT
<213> ORGANISM: Arachis hypogaea

<400> SEQUENCE: 4

```
Leu Thr Ile Leu Val Ala Leu Ala Leu Phe Leu Leu Ala Ala His Ala
1               5                   10                  15

Ser Ala Arg Gln Gln Trp Glu Leu Gln Gly Asp Arg Arg Cys Gln Ser
            20                  25                  30

Gln Leu Glu Arg Ala Asn Leu Arg Pro Cys Glu Gln His Leu Met Gln
        35                  40                  45

Lys Ile Gln Arg Asp Glu Asp Ser Tyr Glu Arg Asp Pro Tyr Ser Pro
    50                  55                  60

Ser Gln Asp Pro Tyr Ser Pro Ser Pro Tyr Asp Arg Arg Gly Ala Gly
65                  70                  75                  80

Ser Ser Gln His Gln Glu Arg Cys Cys Asn Glu Leu Asn Glu Phe Glu
                85                  90                  95

Asn Asn Gln Arg Cys Met Cys Glu Ala Leu Gln Gln Ile Met Glu Asn
            100                 105                 110

Gln Ser Asp Arg Leu Gln Gly Arg Gln Gln Glu Gln Gln Phe Lys Arg
        115                 120                 125

Glu Leu Arg Asn Leu Pro Gln Gln Cys Gly Leu Arg Ala Pro Gln Arg
    130                 135                 140

Cys Asp Leu Asp Val Glu Ser Gly Gly Arg Asp Arg Tyr
145                 150                 155
```

<210> SEQ ID NO 5
<211> LENGTH: 1524
<212> TYPE: DNA
<213> ORGANISM: Arachis hypogaea

<400> SEQUENCE: 5

```
cggcagcaac cggaggagaa cgcgtgccag ttccagcgcc tcaatgcgca gagacctgac    60
aatcgcattg aatcagaggg cggttacatt gagacttgga accccaacaa ccaggagttc   120
gaatgcgccg cgtcgccct ctctcgctta gtcctccgcc gcaacgccct tcgtaggcct    180
ttctactcca atgctcccca ggagatcttc atccagcaag aaggggata ctttgggttg    240 atattccctg ttgtcctag acactatgaa gagcctcaca caaggtcg tcgatctcag     300 tcccaaagac caccaagacg tctccaagga aagaccaaa gccaacagca acgagatagt   360
caccagaagg tgcaccgttt cgatgagggt gatctcattg cagttcccac cggtgttgct   420
ttctggctct acaacgacca cgacactgat gttgttgctg tttctcttac tgacaccaac   480
aacaacgaca ccagcttga tcagttcccc aggagattca atttggctgg gaacacggag   540
caagagttct taaggtacca gcaacaaagc agacaaagca gacgaagaag cttaccatat   600
agcccataca gcccgcaaag tcagcctaga caagaagagc gtgaatttag ccctcgagga   660
cagcacagcc gcagaacg agcaggacaa gaagaagaaa cgaaggtgg aaacatcttc     720 agcggcttca cgccggagtt cctgaacaa gccttccagg ttgacgacag acagatagtg   780
caaaacctaa gaggcgagac cgagagtgaa gaagagggag ccattgtgac agtgagggga   840
```

```
ggcctcagaa tcttgagccc agatagaaag agacgtgccg acgaagaaga ggaatacgat    900
gaagatgaat atgaatacga tgaagaggat agaaggcgtg gcaggggaag cagaggcagg    960
gggaatggta ttgaagagac gatctgcacc gcaagtgcta aaaagaacat tggtagaaac   1020
agatccctg acatctacaa ccctcaagct ggttcactca aaactgccaa cgatctcaac   1080
cttctaatac ttaggtggct tggacctagt gctgaatatg gaaatctcta caggaatgca   1140
ttgtttgtcg ctcactacaa caccaacgca cacagcatca tatatcgatt gaggggacgg   1200
gctcacgtgc aagtcgtgga cagcaacggc aacagagtgt acgacgagga gcttcaagag   1260
ggtcacgtgc ttgtggtgcc acagaacttc gccgtcgctg aaagtccca gagcgagaac   1320
ttcgaatacg tggcattcaa gacagactca aggcccagca tagccaacct cgccggtgaa   1380
aactccgtca tagataacct gccggaggag gtggttgcaa attcatatgg cctccaaagg   1440
gagcaggcaa ggcagcttaa gaacaacaac cccttcaagt tcttcgttcc accgtctcag   1500
cagtctccga gggctgtggc ttaa                                         1524
```

<210> SEQ ID NO 6
<211> LENGTH: 510
<212> TYPE: PRT
<213> ORGANISM: Arachis hypogaea

<400> SEQUENCE: 6

```
Ile Ser Phe Arg Gln Gln Pro Glu Glu Asn Ala Cys Gln Phe Gln Arg
  1               5                  10                  15

Leu Asn Ala Gln Arg Pro Asp Asn Arg Ile Glu Ser Glu Gly Gly Tyr
             20                  25                  30

Ile Glu Thr Trp Asn Pro Asn Asn Gln Glu Phe Glu Cys Ala Gly Val
         35                  40                  45

Ala Leu Ser Arg Leu Val Leu Arg Arg Asn Ala Leu Arg Arg Pro Phe
     50                  55                  60

Tyr Ser Asn Ala Pro Gln Glu Ile Phe Ile Gln Gln Gly Arg Gly Tyr
 65                  70                  75                  80

Phe Gly Leu Ile Phe Pro Gly Cys Pro Arg His Tyr Glu Glu Pro His
                 85                  90                  95

Thr Gln Gly Arg Arg Ser Gln Ser Gln Arg Pro Arg Arg Leu Gln
            100                 105                 110

Gly Glu Asp Gln Ser Gln Gln Arg Asp Ser His Gln Lys Val His
        115                 120                 125

Arg Phe Asp Glu Gly Asp Leu Ile Ala Val Pro Thr Gly Val Ala Phe
    130                 135                 140

Trp Leu Tyr Asn Asp His Asp Thr Asp Val Val Ala Val Ser Leu Thr
145                 150                 155                 160

Asp Thr Asn Asn Asn Asp Asn Gln Leu Asp Gln Phe Pro Arg Arg Phe
                165                 170                 175

Asn Leu Ala Gly Asn Thr Glu Gln Glu Phe Leu Arg Tyr Gln Gln Gln
            180                 185                 190

Ser Arg Gln Ser Arg Arg Arg Ser Leu Pro Tyr Ser Pro Tyr Ser Pro
        195                 200                 205

Gln Ser Gln Pro Arg Gln Glu Glu Arg Glu Phe Ser Pro Arg Gly Gln
    210                 215                 220

His Ser Arg Arg Glu Arg Ala Gly Gln Glu Glu Asn Glu Gly Gly
225                 230                 235                 240

Asn Ile Phe Ser Gly Phe Thr Pro Glu Phe Leu Glu Gln Ala Phe Gln
                245                 250                 255
```

Val Asp Asp Arg Gln Ile Val Gln Asn Leu Arg Gly Glu Thr Glu Ser
            260                 265                 270

Glu Glu Glu Gly Ala Ile Val Thr Val Arg Gly Gly Leu Arg Ile Leu
        275                 280                 285

Ser Pro Asp Arg Lys Arg Ala Asp Glu Glu Glu Tyr Asp Glu
        290                 295                 300

Asp Glu Tyr Glu Tyr Asp Glu Asp Arg Arg Gly Arg Gly Ser
305                 310                 315                 320

Arg Gly Arg Gly Asn Gly Ile Glu Glu Thr Ile Cys Thr Ala Ser Ala
                325                 330                 335

Lys Lys Asn Ile Gly Arg Asn Arg Ser Pro Asp Ile Tyr Asn Pro Gln
                340                 345                 350

Ala Gly Ser Leu Lys Thr Ala Asn Asp Leu Asn Leu Leu Ile Leu Arg
            355                 360                 365

Trp Leu Gly Pro Ser Ala Glu Tyr Gly Asn Leu Tyr Arg Asn Ala Leu
370                 375                 380

Phe Val Ala His Tyr Asn Thr Asn Ala His Ser Ile Ile Tyr Arg Leu
385                 390                 395                 400

Arg Gly Arg Ala His Val Gln Val Val Asp Ser Asn Gly Asn Arg Val
                405                 410                 415

Tyr Asp Glu Glu Leu Gln Glu Gly His Val Leu Val Val Pro Gln Asn
                420                 425                 430

Phe Ala Val Ala Gly Lys Ser Gln Ser Glu Asn Phe Glu Tyr Val Ala
            435                 440                 445

Phe Lys Thr Asp Ser Arg Pro Ser Ile Ala Asn Leu Ala Gly Glu Asn
        450                 455                 460

Ser Val Ile Asp Asn Leu Pro Glu Glu Val Val Ala Asn Ser Tyr Gly
465                 470                 475                 480

Leu Gln Arg Glu Gln Ala Arg Gln Leu Lys Asn Asn Asn Pro Phe Lys
                485                 490                 495

Phe Phe Val Pro Pro Ser Gln Gln Ser Pro Arg Ala Val Ala
                500                 505                 510

<210> SEQ ID NO 7
<211> LENGTH: 10
<212> TYPE: PRT
<213> ORGANISM: Arachis hypogaea

<400> SEQUENCE: 7

Ala Lys Ser Ser Pro Tyr Gln Lys Lys Thr
1               5                   10

<210> SEQ ID NO 8
<211> LENGTH: 10
<212> TYPE: PRT
<213> ORGANISM: Arachis hypogaea

<400> SEQUENCE: 8

Gln Glu Pro Asp Asp Leu Lys Gln Lys Ala
1               5                   10

<210> SEQ ID NO 9
<211> LENGTH: 10
<212> TYPE: PRT
<213> ORGANISM: Arachis hypogaea

<400> SEQUENCE: 9

```
Leu Glu Tyr Asp Pro Arg Leu Val Tyr Asp
1               5                   10

<210> SEQ ID NO 10
<211> LENGTH: 10
<212> TYPE: PRT
<213> ORGANISM: Arachis hypogaea

<400> SEQUENCE: 10

Gly Glu Arg Thr Arg Gly Arg Gln Pro Gly
1               5                   10

<210> SEQ ID NO 11
<211> LENGTH: 10
<212> TYPE: PRT
<213> ORGANISM: Arachis hypogaea

<400> SEQUENCE: 11

Pro Gly Asp Tyr Asp Asp Arg Arg Gln
1               5                   10

<210> SEQ ID NO 12
<211> LENGTH: 10
<212> TYPE: PRT
<213> ORGANISM: Arachis hypogaea

<400> SEQUENCE: 12

Pro Arg Arg Glu Glu Gly Gly Arg Trp Gly
1               5                   10

<210> SEQ ID NO 13
<211> LENGTH: 10
<212> TYPE: PRT
<213> ORGANISM: Arachis hypogaea

<400> SEQUENCE: 13

Arg Glu Arg Glu Glu Asp Trp Arg Gln Pro
1               5                   10

<210> SEQ ID NO 14
<211> LENGTH: 10
<212> TYPE: PRT
<213> ORGANISM: Arachis hypogaea

<400> SEQUENCE: 14

Glu Asp Trp Arg Arg Pro Ser His Gln Gln
1               5                   10

<210> SEQ ID NO 15
<211> LENGTH: 10
<212> TYPE: PRT
<213> ORGANISM: Arachis hypogaea

<400> SEQUENCE: 15

Gln Pro Arg Lys Ile Arg Pro Glu Gly Arg
1               5                   10

<210> SEQ ID NO 16
<211> LENGTH: 10
<212> TYPE: PRT
<213> ORGANISM: Arachis hypogaea

<400> SEQUENCE: 16

Thr Pro Gly Gln Phe Glu Asp Phe Phe Pro
1               5                   10
```

```
<210> SEQ ID NO 17
<211> LENGTH: 10
<212> TYPE: PRT
<213> ORGANISM: Arachis hypogaea

<400> SEQUENCE: 17

Ser Tyr Leu Gln Glu Phe Ser Arg Asn Thr
1               5                   10

<210> SEQ ID NO 18
<211> LENGTH: 10
<212> TYPE: PRT
<213> ORGANISM: Arachis hypogaea

<400> SEQUENCE: 18

Phe Asn Ala Glu Phe Asn Glu Ile Arg Arg
1               5                   10

<210> SEQ ID NO 19
<211> LENGTH: 10
<212> TYPE: PRT
<213> ORGANISM: Arachis hypogaea

<400> SEQUENCE: 19

Glu Gln Glu Glu Arg Gly Gln Arg Arg Trp
1               5                   10

<210> SEQ ID NO 20
<211> LENGTH: 10
<212> TYPE: PRT
<213> ORGANISM: Arachis hypogaea

<400> SEQUENCE: 20

Asp Ile Thr Asn Pro Ile Asn Leu Arg Glu
1               5                   10

<210> SEQ ID NO 21
<211> LENGTH: 10
<212> TYPE: PRT
<213> ORGANISM: Arachis hypogaea

<400> SEQUENCE: 21

Asn Asn Phe Gly Lys Leu Phe Glu Val Lys
1               5                   10

<210> SEQ ID NO 22
<211> LENGTH: 10
<212> TYPE: PRT
<213> ORGANISM: Arachis hypogaea

<400> SEQUENCE: 22

Gly Thr Gly Asn Leu Glu Leu Val Ala Val
1               5                   10

<210> SEQ ID NO 23
<211> LENGTH: 10
<212> TYPE: PRT
<213> ORGANISM: Arachis hypogaea

<400> SEQUENCE: 23

Arg Arg Tyr Thr Ala Arg Leu Lys Glu Gly
1               5                   10
```

```
<210> SEQ ID NO 24
<211> LENGTH: 10
<212> TYPE: PRT
<213> ORGANISM: Arachis hypogaea

<400> SEQUENCE: 24

Glu Leu His Leu Leu Gly Phe Gly Ile Asn
1               5                   10

<210> SEQ ID NO 25
<211> LENGTH: 10
<212> TYPE: PRT
<213> ORGANISM: Arachis hypogaea

<400> SEQUENCE: 25

His Arg Ile Phe Leu Ala Gly Asp Lys Asp
1               5                   10

<210> SEQ ID NO 26
<211> LENGTH: 10
<212> TYPE: PRT
<213> ORGANISM: Arachis hypogaea

<400> SEQUENCE: 26

Ile Asp Gln Ile Glu Lys Gln Ala Lys Asp
1               5                   10

<210> SEQ ID NO 27
<211> LENGTH: 10
<212> TYPE: PRT
<213> ORGANISM: Arachis hypogaea

<400> SEQUENCE: 27

Lys Asp Leu Ala Phe Pro Gly Ser Gly Glu
1               5                   10

<210> SEQ ID NO 28
<211> LENGTH: 10
<212> TYPE: PRT
<213> ORGANISM: Arachis hypogaea

<400> SEQUENCE: 28

Lys Glu Ser His Phe Val Ser Ala Arg Pro
1               5                   10

<210> SEQ ID NO 29
<211> LENGTH: 10
<212> TYPE: PRT
<213> ORGANISM: Arachis hypogaea

<400> SEQUENCE: 29

Pro Glu Lys Glu Ser Pro Glu Lys Glu Asp
1               5                   10

<210> SEQ ID NO 30
<211> LENGTH: 10
<212> TYPE: PRT
<213> ORGANISM: Arachis hypogaea

<400> SEQUENCE: 30

His Ala Ser Ala Arg Gln Gln Trp Glu Leu
1               5                   10

<210> SEQ ID NO 31
<211> LENGTH: 10
```

<212> TYPE: PRT
<213> ORGANISM: Arachis hypogaea

<400> SEQUENCE: 31

Gln Trp Glu Leu Gln Gly Asp Arg Arg Cys
1               5                   10

<210> SEQ ID NO 32
<211> LENGTH: 10
<212> TYPE: PRT
<213> ORGANISM: Arachis hypogaea

<400> SEQUENCE: 32

Asp Arg Arg Cys Gln Ser Gln Leu Glu Arg
1               5                   10

<210> SEQ ID NO 33
<211> LENGTH: 10
<212> TYPE: PRT
<213> ORGANISM: Arachis hypogaea

<400> SEQUENCE: 33

Leu Arg Pro Cys Glu Gln His Leu Met Gln
1               5                   10

<210> SEQ ID NO 34
<211> LENGTH: 10
<212> TYPE: PRT
<213> ORGANISM: Arachis hypogaea

<400> SEQUENCE: 34

Lys Ile Gln Arg Asp Glu Asp Ser Tyr Glu
1               5                   10

<210> SEQ ID NO 35
<211> LENGTH: 10
<212> TYPE: PRT
<213> ORGANISM: Arachis hypogaea

<400> SEQUENCE: 35

Tyr Glu Arg Asp Pro Tyr Ser Pro Ser Gln
1               5                   10

<210> SEQ ID NO 36
<211> LENGTH: 10
<212> TYPE: PRT
<213> ORGANISM: Arachis hypogaea

<400> SEQUENCE: 36

Ser Gln Asp Pro Tyr Ser Pro Ser Pro Tyr
1               5                   10

<210> SEQ ID NO 37
<211> LENGTH: 10
<212> TYPE: PRT
<213> ORGANISM: Arachis hypogaea

<400> SEQUENCE: 37

Asp Arg Leu Gln Gly Arg Gln Gln Glu Gln
1               5                   10

<210> SEQ ID NO 38
<211> LENGTH: 10
<212> TYPE: PRT
<213> ORGANISM: Arachis hypogaea

```
<400> SEQUENCE: 38

Lys Arg Glu Leu Arg Asn Leu Pro Gln Gln
1               5                   10

<210> SEQ ID NO 39
<211> LENGTH: 10
<212> TYPE: PRT
<213> ORGANISM: Arachis hypogaea

<400> SEQUENCE: 39

Gln Arg Cys Asp Leu Asp Val Glu Ser Gly
1               5                   10

<210> SEQ ID NO 40
<211> LENGTH: 15
<212> TYPE: PRT
<213> ORGANISM: Arachis hypogaea

<400> SEQUENCE: 40

Ile Glu Thr Trp Asn Pro Asn Asn Gln Glu Phe Glu Cys Ala Gly
1               5                   10                  15

<210> SEQ ID NO 41
<211> LENGTH: 15
<212> TYPE: PRT
<213> ORGANISM: Arachis hypogaea

<400> SEQUENCE: 41

Gly Asn Ile Phe Ser Gly Phe Thr Pro Glu Phe Leu Glu Gln Ala
1               5                   10                  15

<210> SEQ ID NO 42
<211> LENGTH: 15
<212> TYPE: PRT
<213> ORGANISM: Arachis hypogaea

<400> SEQUENCE: 42

Val Thr Val Arg Gly Gly Leu Arg Ile Leu Ser Pro Asp Arg Lys
1               5                   10                  15

<210> SEQ ID NO 43
<211> LENGTH: 15
<212> TYPE: PRT
<213> ORGANISM: Arachis hypogaea

<400> SEQUENCE: 43

Asp Glu Asp Glu Tyr Glu Tyr Asp Glu Glu Asp Arg Arg Arg Gly
1               5                   10                  15

<210> SEQ ID NO 44
<211> LENGTH: 52
<212> TYPE: PRT
<213> ORGANISM: Arachis hypogaea

<400> SEQUENCE: 44

Thr Asn Gln Arg Ser Pro Pro Gly Glu Arg Thr Arg Gly Arg Gln Pro
1               5                   10                  15

Gly Asp Tyr Asp Asp Arg Arg Gln Pro Arg Arg Glu Glu Gly Gly
            20                  25                  30

Arg Trp Gly Pro Ala Gly Pro Arg Glu Arg Glu Arg Glu Asp Trp
        35                  40                  45

Arg Gln Pro Arg
```

-continued

```
<210> SEQ ID NO 45
<211> LENGTH: 10
<212> TYPE: PRT
<213> ORGANISM: Arachis hypogaea

<400> SEQUENCE: 45

Thr Asn Gln Arg Ser Pro Pro Gly Glu Arg
1               5                   10

<210> SEQ ID NO 46
<211> LENGTH: 10
<212> TYPE: PRT
<213> ORGANISM: Arachis hypogaea

<400> SEQUENCE: 46

Gln Arg Ser Pro Pro Gly Glu Arg Thr Arg
1               5                   10

<210> SEQ ID NO 47
<211> LENGTH: 10
<212> TYPE: PRT
<213> ORGANISM: Arachis hypogaea

<400> SEQUENCE: 47

Ser Pro Pro Gly Glu Arg Thr Arg Gly Arg
1               5                   10

<210> SEQ ID NO 48
<211> LENGTH: 10
<212> TYPE: PRT
<213> ORGANISM: Arachis hypogaea

<400> SEQUENCE: 48

Pro Gly Glu Arg Thr Arg Gly Arg Gln Pro
1               5                   10

<210> SEQ ID NO 49
<211> LENGTH: 10
<212> TYPE: PRT
<213> ORGANISM: Arachis hypogaea

<400> SEQUENCE: 49

Glu Arg Thr Arg Gly Arg Gln Pro Gly Asp
1               5                   10

<210> SEQ ID NO 50
<211> LENGTH: 10
<212> TYPE: PRT
<213> ORGANISM: Arachis hypogaea

<400> SEQUENCE: 50

Thr Arg Gly Arg Gln Pro Gly Asp Tyr Asp
1               5                   10

<210> SEQ ID NO 51
<211> LENGTH: 10
<212> TYPE: PRT
<213> ORGANISM: Arachis hypogaea

<400> SEQUENCE: 51

Gly Arg Gln Pro Gly Asp Tyr Asp Asp Asp
1               5                   10
```

<210> SEQ ID NO 52
<211> LENGTH: 10
<212> TYPE: PRT
<213> ORGANISM: Arachis hypogaea

<400> SEQUENCE: 52

Gln Pro Gly Asp Tyr Asp Asp Arg Arg
1               5               10

<210> SEQ ID NO 53
<211> LENGTH: 10
<212> TYPE: PRT
<213> ORGANISM: Arachis hypogaea

<400> SEQUENCE: 53

Gly Asp Tyr Asp Asp Arg Arg Gln Pro
1               5               10

<210> SEQ ID NO 54
<211> LENGTH: 10
<212> TYPE: PRT
<213> ORGANISM: Arachis hypogaea

<400> SEQUENCE: 54

Tyr Asp Asp Asp Arg Arg Gln Pro Arg Arg
1               5               10

<210> SEQ ID NO 55
<211> LENGTH: 10
<212> TYPE: PRT
<213> ORGANISM: Arachis hypogaea

<400> SEQUENCE: 55

Asp Asp Arg Arg Gln Pro Arg Arg Glu Glu
1               5               10

<210> SEQ ID NO 56
<211> LENGTH: 10
<212> TYPE: PRT
<213> ORGANISM: Arachis hypogaea

<400> SEQUENCE: 56

Arg Arg Gln Pro Arg Arg Glu Glu Gly Gly
1               5               10

<210> SEQ ID NO 57
<211> LENGTH: 10
<212> TYPE: PRT
<213> ORGANISM: Arachis hypogaea

<400> SEQUENCE: 57

Gln Pro Arg Arg Glu Glu Gly Gly Arg Trp
1               5               10

<210> SEQ ID NO 58
<211> LENGTH: 10
<212> TYPE: PRT
<213> ORGANISM: Arachis hypogaea

<400> SEQUENCE: 58

Arg Arg Glu Glu Gly Gly Arg Trp Gly Pro
1               5               10

<210> SEQ ID NO 59

```
<211> LENGTH: 10
<212> TYPE: PRT
<213> ORGANISM: Arachis hypogaea

<400> SEQUENCE: 59

Glu Glu Gly Gly Arg Trp Gly Pro Ala Gly
1               5                   10

<210> SEQ ID NO 60
<211> LENGTH: 10
<212> TYPE: PRT
<213> ORGANISM: Arachis hypogaea

<400> SEQUENCE: 60

Gly Gly Arg Trp Gly Pro Ala Gly Pro Arg
1               5                   10

<210> SEQ ID NO 61
<211> LENGTH: 10
<212> TYPE: PRT
<213> ORGANISM: Arachis hypogaea

<400> SEQUENCE: 61

Arg Trp Gly Pro Ala Gly Pro Arg Glu Arg
1               5                   10

<210> SEQ ID NO 62
<211> LENGTH: 10
<212> TYPE: PRT
<213> ORGANISM: Arachis hypogaea

<400> SEQUENCE: 62

Gly Pro Ala Gly Pro Arg Glu Arg Glu Arg
1               5                   10

<210> SEQ ID NO 63
<211> LENGTH: 10
<212> TYPE: PRT
<213> ORGANISM: Arachis hypogaea

<400> SEQUENCE: 63

Ala Gly Pro Arg Glu Arg Glu Arg Glu Glu
1               5                   10

<210> SEQ ID NO 64
<211> LENGTH: 10
<212> TYPE: PRT
<213> ORGANISM: Arachis hypogaea

<400> SEQUENCE: 64

Pro Arg Glu Arg Glu Arg Glu Glu Asp Trp
1               5                   10

<210> SEQ ID NO 65
<211> LENGTH: 10
<212> TYPE: PRT
<213> ORGANISM: Arachis hypogaea

<400> SEQUENCE: 65

Glu Arg Glu Arg Glu Glu Asp Trp Arg Gln
1               5                   10

<210> SEQ ID NO 66
<211> LENGTH: 10
<212> TYPE: PRT
```

<213> ORGANISM: Arachis hypogaea

<400> SEQUENCE: 66

Glu Arg Glu Glu Asp Trp Arg Gln Pro Arg
1               5                   10

<210> SEQ ID NO 67
<211> LENGTH: 22
<212> TYPE: PRT
<213> ORGANISM: Arachis hypogaea

<400> SEQUENCE: 67

Asp Ser Tyr Glu Arg Asp Pro Tyr Ser Pro Ser Gln Asp Pro Tyr Ser
1               5                   10                  15

Pro Ser Pro Tyr Asp Arg
            20

<210> SEQ ID NO 68
<211> LENGTH: 10
<212> TYPE: PRT
<213> ORGANISM: Arachis hypogaea

<400> SEQUENCE: 68

Asp Ser Tyr Glu Arg Asp Pro Tyr Ser Pro
1               5                   10

<210> SEQ ID NO 69
<211> LENGTH: 10
<212> TYPE: PRT
<213> ORGANISM: Arachis hypogaea

<400> SEQUENCE: 69

Tyr Glu Arg Asp Pro Tyr Ser Pro Ser Gln
1               5                   10

<210> SEQ ID NO 70
<211> LENGTH: 10
<212> TYPE: PRT
<213> ORGANISM: Arachis hypogaea

<400> SEQUENCE: 70

Arg Asp Pro Tyr Ser Pro Ser Gln Asp Pro
1               5                   10

<210> SEQ ID NO 71
<211> LENGTH: 10
<212> TYPE: PRT
<213> ORGANISM: Arachis hypogaea

<400> SEQUENCE: 71

Pro Tyr Ser Pro Ser Gln Asp Pro Tyr Ser
1               5                   10

<210> SEQ ID NO 72
<211> LENGTH: 10
<212> TYPE: PRT
<213> ORGANISM: Arachis hypogaea

<400> SEQUENCE: 72

Ser Pro Ser Gln Asp Pro Tyr Ser Pro Ser
1               5                   10

<210> SEQ ID NO 73
<211> LENGTH: 10

```
<212> TYPE: PRT
<213> ORGANISM: Arachis hypogaea

<400> SEQUENCE: 73

Ser Gln Asp Pro Tyr Ser Pro Ser Pro Tyr
1               5                   10

<210> SEQ ID NO 74
<211> LENGTH: 10
<212> TYPE: PRT
<213> ORGANISM: Arachis hypogaea

<400> SEQUENCE: 74

Asp Pro Tyr Ser Pro Ser Pro Tyr Asp Arg
1               5                   10

<210> SEQ ID NO 75
<211> LENGTH: 23
<212> TYPE: PRT
<213> ORGANISM: Arachis hypogaea

<400> SEQUENCE: 75

Glu Glu Glu Tyr Asp Glu Asp Glu Tyr Glu Tyr Asp Glu Glu Asp Arg
1               5                   10                  15

Arg Arg Gly Arg Gly Ser Arg
            20

<210> SEQ ID NO 76
<211> LENGTH: 15
<212> TYPE: PRT
<213> ORGANISM: Arachis hypogaea

<400> SEQUENCE: 76

Glu Glu Glu Tyr Asp Glu Asp Glu Tyr Glu Tyr Asp Glu Glu Asp
1               5                   10                  15

<210> SEQ ID NO 77
<211> LENGTH: 15
<212> TYPE: PRT
<213> ORGANISM: Arachis hypogaea

<400> SEQUENCE: 77

Glu Tyr Asp Glu Asp Glu Tyr Glu Tyr Asp Glu Glu Asp Arg Arg
1               5                   10                  15

<210> SEQ ID NO 78
<211> LENGTH: 15
<212> TYPE: PRT
<213> ORGANISM: Arachis hypogaea

<400> SEQUENCE: 78

Asp Glu Asp Glu Tyr Glu Tyr Asp Glu Glu Asp Arg Arg Arg Gly
1               5                   10                  15

<210> SEQ ID NO 79
<211> LENGTH: 15
<212> TYPE: PRT
<213> ORGANISM: Arachis hypogaea

<400> SEQUENCE: 79

Asp Glu Tyr Glu Tyr Asp Glu Glu Asp Arg Arg Arg Gly Arg Gly
1               5                   10                  15

<210> SEQ ID NO 80
```

```
<211> LENGTH: 15
<212> TYPE: PRT
<213> ORGANISM: Arachis hypogaea

<400> SEQUENCE: 80

Tyr Glu Tyr Asp Glu Glu Asp Arg Arg Arg Gly Arg Gly Ser Arg
1               5                   10                  15

<210> SEQ ID NO 81
<211> LENGTH: 15
<212> TYPE: PRT
<213> ORGANISM: Arachis hypogaea

<400> SEQUENCE: 81

Tyr Asp Glu Glu Asp Arg Arg Arg Gly Arg Gly Ser Arg Gly Arg
1               5                   10                  15
```